US009095291B2

(12) United States Patent
Soller et al.

(10) Patent No.: US 9,095,291 B2
(45) Date of Patent: Aug. 4, 2015

(54) SPECTROSCOPIC SENSORS

(75) Inventors: Babs R. Soller, Northboro, MA (US); John Coates, Newton, CT (US); Ye Yang, Scarborough, ME (US); Chunguang Jin, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 525 days.

(21) Appl. No.: 13/057,617

(22) PCT Filed: Aug. 7, 2009

(86) PCT No.: PCT/US2009/053183
§ 371 (c)(1),
(2), (4) Date: May 3, 2011

(87) PCT Pub. No.: WO2010/053617
PCT Pub. Date: May 14, 2010

(65) Prior Publication Data
US 2011/0205535 A1 Aug. 25, 2011

Related U.S. Application Data

(60) Provisional application No. 61/087,084, filed on Aug. 7, 2008.

(51) Int. Cl.
*A61B 5/1455* (2006.01)
*A61B 5/145* (2006.01)
*A61B 5/00* (2006.01)

(52) U.S. Cl.
CPC .............. *A61B 5/1455* (2013.01); *A61B 5/145* (2013.01); *A61B 5/14552* (2013.01);
(Continued)

(58) Field of Classification Search
USPC .......................... 600/407, 473, 475, 476, 477
See application file for complete search history.

(56) References Cited

U.S. PATENT DOCUMENTS 5,020,112 A * 5/1991 Chou ............................ 382/226
5,363,843 A * 11/1994 Daneshvar .................... 128/897
(Continued)

FOREIGN PATENT DOCUMENTS

JP 06-319723 11/1994
JP 11-128184 5/1999
(Continued)

OTHER PUBLICATIONS

Becker et al., "The PULSE initiative: scientific priorities and strategic planning for resuscitation research and life saving therapies," *Circulation* 105: 2562-2570 (2002).
(Continued)

*Primary Examiner* — Long V Le
*Assistant Examiner* — Michael Kellogg
(74) *Attorney, Agent, or Firm* — Fish & Richardson P.C.

(57) ABSTRACT

Disclosed herein are sensors that include: (a) a circuit board that includes an electronic processor; (b) a plurality of radiation sources, each source being attached to the circuit board; and (c) a spectral detector attached to the circuit board, the spectral detector being configured to analyze radiation derived from one or more of the plurality of radiation sources. During use, the sensors are configured to be worn on a portion of a body of a subject. The electronic processor is configured to cause two or more of the plurality of radiation sources to direct incident radiation to the subject, to cause the spectral detector to analyze radiation from the subject, and to determine one or more properties of the subject based on the radiation from the subject. Methods of making and using these sensors are also disclosed.

20 Claims, 19 Drawing Sheets

(52) U.S. Cl.
CPC .......... *A61B 5/0082* (2013.01); *A61B 5/14539* (2013.01); *A61B 5/412* (2013.01); *A61B 5/6801* (2013.01); *A61B 2562/0233* (2013.01); *A61B 2562/0238* (2013.01); *A61B 2562/0242* (2013.01); *A61B 2562/04* (2013.01); *A61B 2562/046* (2013.01)

(56) References Cited

U.S. PATENT DOCUMENTS

| | | | |
|---|---|---|---|
| 5,477,853 | A | 12/1995 | Farkas et al. |
| 5,497,769 | A * | 3/1996 | Gratton et al. ............... 600/323 |
| 5,582,170 | A | 12/1996 | Soller |
| 5,813,403 | A | 9/1998 | Soller et al. |
| 6,006,119 | A | 12/1999 | Soller et al. |
| 6,045,511 | A * | 4/2000 | Ott et al. ...................... 600/504 |
| 6,304,767 | B1 | 10/2001 | Soller et al. |
| 6,564,088 | B1 | 5/2003 | Soller et al. |
| 6,766,188 | B2 | 7/2004 | Soller et al. |
| 7,245,373 | B2 | 7/2007 | Soller et al. |
| 7,532,919 | B2 | 5/2009 | Soyemi et al. |
| 7,616,303 | B2 | 11/2009 | Yang et al. |
| 7,881,892 | B2 | 2/2011 | Soyemi et al. |
| 2002/0016536 | A1 | 2/2002 | Benni |
| 2003/0032064 | A1 | 2/2003 | Soller et al. |
| 2004/0005717 | A1 | 1/2004 | Soller |
| 2007/0038041 | A1 * | 2/2007 | Yang et al. .................... 600/310 |
| 2007/0084990 | A1 * | 4/2007 | Coates ........................ 250/226 |
| 2007/0112258 | A1 | 5/2007 | Soyemi et al. |
| 2007/0123756 | A1 | 5/2007 | Kitajima et al. |
| 2008/0015424 | A1 * | 1/2008 | Bernreuter ................... 600/323 |
| 2008/0081970 | A1 | 4/2008 | Boyce et al. |
| 2008/0097173 | A1 * | 4/2008 | Soyemi et al. ................ 600/310 |
| 2008/0132793 | A1 * | 6/2008 | Kollias et al. ................. 600/476 |
| 2009/0024013 | A1 | 1/2009 | Soller et al. |
| 2011/0184683 | A1 | 7/2011 | Soller et al. |

FOREIGN PATENT DOCUMENTS

| | | |
|---|---|---|
| JP | 2007-196001 | 8/2007 |
| WO | 96/35940 | 11/1996 |
| WO | 2008/030250 | 3/2008 |
| WO | WO 2010/053617 | 5/2010 |

OTHER PUBLICATIONS

Coates, J.P., "Think Small: Low-Coast Optical Spectral Measurements for Chemical Sensing," *Spectroscopy* 21: 20-25 (2006).

Cooke et al., "Heart rate variability and spontaneous baroreflex sequences: implications for autonomic monitoring during hemorrhage," *J. Trauma* 58: 798-805 (2005).

Soller et al., "Application of fiberoptic sensors for the study of hepatic dysoxia in swine hemorrhagic shock," *Crit. Care Med.* 29: 1438-1444 (2001).

Soller et al., "Investigation of Muscle pH as an Indicator of Liver pH and Injury from Hemorrhagic Shock," *J. Surgical Research* 114: 195-201 (2003).

Soller et al., "Noninvasive, NIRS-measured muscle pH and PO2 indicate tissue perfusion for cardiac surgical patients on cardiopulmonary bypass," *Crit. Care Med.* 31: 2324-2331 (2003).

Soller et al., "Noninvasively determined muscle oxygen saturation is an early indicator of central hypovolemia in humans," *J. Appl. Physiol.* 104: 475-481 (2008).

Soller et al., "Oxygen saturation determined from deep muscle, not thenar tissue, is an early indicator of central hypovolemia in humans," *Crit. Care Med.* 36: 176-182 (2008).

Yang et al., "Effect of skin and fat layers on the spatial sensitivity profile of continuous wave diffuse reflectance near-infrared spectra," *Proc. SPIE* 6007: 108-116 (2005).

Yang et al., "Noninvasive in vivo Measurement of Venous Blood pH during Exercise using NIR Reflectance Spectroscopy," *Appl. Spectroscopy* 61: 223-229 (2007).

Soller et al., "Noninvasive determination of exercise-induced hydrogen ion threshold through direct optical measurement," *Journal of Applied Physiology*, 104: 837-844 (2008).

Soyemi et al., "Standardization method for correcting spectral differences across multiple units of a portable near infrared-based medical monitor," *Proc. SPIE*, 5702: 135-142 (2005).

Yang et al., "Quantitative measurement of muscle oxygen saturation without influence from skin and fat using continuous-wave near infrared spectroscopy," *Optics Express*, 15: 13715-13730 (2007).

Yang et al., "Removal of analyte-irrelevant variation in near infrared tissue spectra," *Applied Spectroscopy*, 60: 1070-1077 (2006).

Yang et al., "Simultaneous correction of skin color and fat thickness for tissue spectroscopy using a two-distance fiber optic probe and orthogonalization techniques," *Optics Letters*, 30: 2269-2271 (2005).

Zhang et al., "Partial least-squares modeling of near-infrared reflectance data for noninvasive in vivo determination of deep-tissue pH," *Applied Spectroscopy*, 52: 400-406 (1998).

International Search Report and Written Opinion issued in PCT/US2009/053183 on May 13, 2010.

International Preliminary Report on Patentability and Written Opinion issued in PCT/US2009/053183 on Feb. 8, 2011.

Office Action (English translation) in JP Patent Application 2011-522286, dated Nov. 20, 2013, 11 pages.

Office Action in EP Patent Application 09825161 4, dated Feb. 26, 2014, 3 pages.

Office Action in EP Patent Application 09825161 4, dated Mar. 4, 2014, 5 pages.

Office Action (English translation) in CN Patent Application No. 2009801395424, dated Oct. 8, 2012, 5 pages.

Office Action (English translation) in CN Patent Application No. 2009801395424, dated Jul. 1, 2013, 25 pages.

Office Action (English translation) in CN Patent Application No. 2009801395424, dated Mar. 25, 2014, 13 pages.

Beilman et al., "Near-infrared spectroscopy measurement of regional tissue oxyhemoglobin saturation during hemorrhagic shock," *Shock* 12: 196-200 (1999).

Bellamy, R.F., "The causes of death in conventional land warfare: implications for combat casualty care research," *Military Medicine* 149: 55-62 (1984).

Coates, J.P., "New Microspectrometers: Building on the Principle that Simple is Beautiful," *Spectroscopy* 15: 21-27 (2000).

Morelli, Dennis W. Interference Filter Handbook, A Guide for Specifying Optimum Filter Performance, JDSU. Jan. 1991, First Edition.

Sauaia et al., "Epidemiology of trauma deaths: a reassessment," *J. Trauma* 38: 185-193 (1995).

Soller et al., "Feasibility of non-invasive measurement of tissue pH using near-infrared reflectance spectrosopy," *J. Clin. Monit.* 12: 387-395 (1996).

Soller et al., "Simultaneous measurement of hepatic tissue pH, venous oxygen saturation and hemoglobin by near infrared spectroscopy," *Shock* 15: 106-111 (2001).

Zhang et al., "Investigation of noninvasive in vivo blood hematocrit measurement using NIR reflectance spectroscopy and partial least-squares regression," *Appl. Spectroscopy* 54: 294-299 (2000).

* cited by examiner

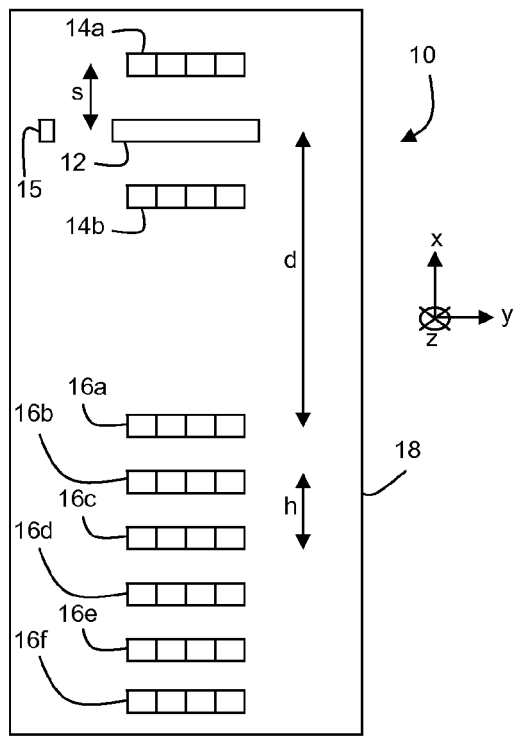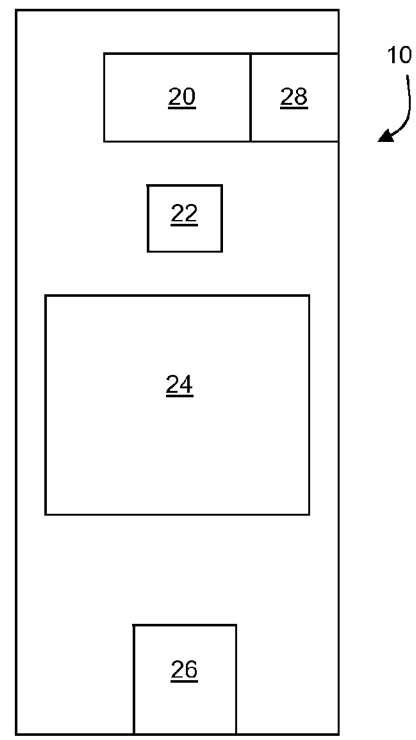
FIG. 1A  FIG. 1B
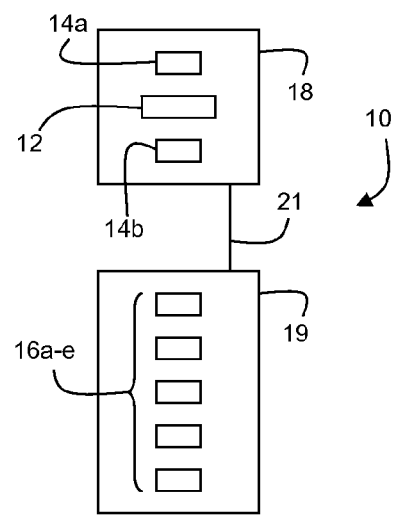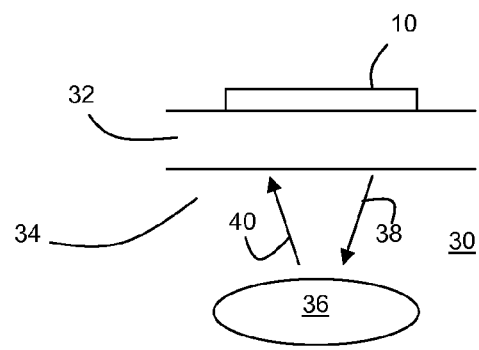
FIG. 1C  FIG. 2

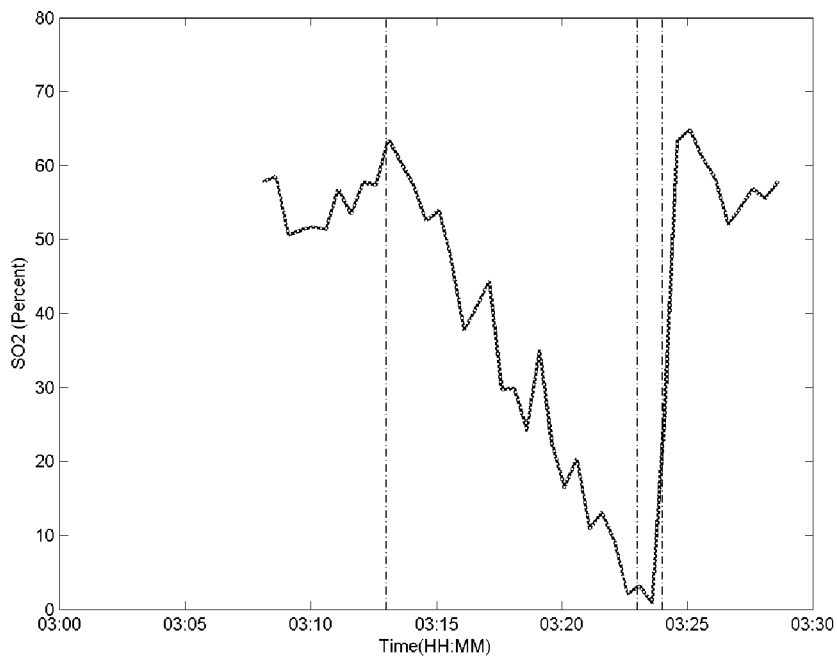
FIG. 23
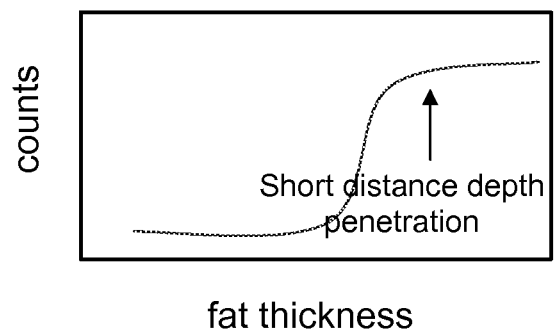
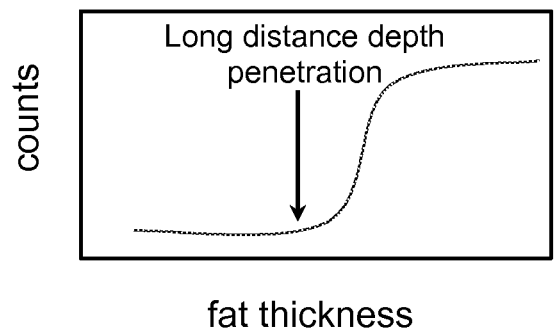
FIG. 24

SPECTROSCOPIC SENSORS

STATEMENT AS TO FEDERALLY SPONSORED RESEARCH

This invention was made with Government support under National Space Biomedical Research Institute Grant No. SMS00004, and under U.S. Army Medical Research and Materiel Command Contract No. W81XWH-06-1-0545. The Government has certain rights in this invention.

CROSS-REFERENCE TO RELATED APPLICATIONS

This application is the U.S. national stage application under 35 USC §371 of International Application Number PCT/US2009/053183, filed on Aug. 7, 2009, which claims priority to U.S. Provisional Patent Application Ser. No. 61/087,084, filed on Aug. 7, 2008. The entire contents of each of the foregoing applications are incorporated herein by reference.

TECHNICAL FIELD

This disclosure relates to sensors, and in particular, to spectroscopic sensors for measuring sample properties.

BACKGROUND

Near-infrared radiation can generally pass through layers of skin and fat to illuminate blood vessels in muscle tissues. The radiation can be absorbed by hemoglobin in red blood cells, myoglobin in muscle fibers, water, and other proteins in blood plasma. Radiation is scattered by both muscle fibers and blood cells, and the scattered radiation can be detected and analyzed to determine the wavelength dependence of the scattered radiation. The absorbance spectrum of the various absorbing components in muscle tissues can be determined by comparing the spectra of incident radiation delivered to the tissues and the scattered radiation from the tissues. For certain samples, particular spectral features in the absorbance spectrum can be assigned to particular components in the muscle tissues (e.g., certain spectral signatures can be assigned to absorption by hemoglobin and/or myoglobin).

SUMMARY

Disclosed herein are devices, e.g., sensors, and methods for measuring near-infrared spectra of samples, including tissues of humans and animals, and for determining one or more properties of the samples based on the spectra. In particular, the apparatus disclosed herein includes circuit board-based sensors that include multiple radiation sources, a spectral detector, and an electronic processor that controls the sources and detector, processes spectral information from the detector to calculate absorbance spectra of samples, and determines properties of the samples based on the absorbance spectra.

The sensors can include radiation sources at different source-detector distances. In particular, the sensors can include multiple long-distance sources, each of which can illuminate a sample, and following which illumination scattered radiation from the sample can be measured. Scattered radiation spectra derived from long-distance source illumination of the sample typically include spectral contributions from both muscle tissues within the sample, and from layers of skin and/or fat positioned between the sensor and the muscle tissues. Absorbance spectra can be generated from the scattered radiation spectra by comparing the scattered radiation spectra to incident radiation spectra from the long-distance sources.

In the following discussion, reference is made to absorbance spectra of samples. However, the apparatus and methods disclosed herein can also be used to derive reflectance spectra from measured scattered radiation spectra. In general, reflectance and absorbance are related by a simple mathematical transformation, and the apparatus and methods disclosed herein can be used interchangeably with reflectance and/or absorbance information derived from samples. Methods for converting spectral scattered radiation information into reflectance and/or absorbance spectra for a sample are disclosed, for example, in U.S. Patent Application Publication No. US 2008/0097173, the entire contents of which are incorporated herein by reference.

The sensors also typically include one or more short-distance sources, that can illuminate the sample, and following which illumination scattered radiation from the sample can be measured. Typically, scattered radiation spectra derived from short-distance source illumination of the sample include spectral contributions substantially only from the layers of skin and/or fat positioned between the sensor and the muscle tissues. As above, absorbance spectra can be generated from the scattered radiation spectra by comparing the scattered radiation spectra to incident radiation spectra from the short-distance sources. Furthermore, by combining the absorbance spectra derived from both long-distance and short-distance illumination sources, the absorbance spectra can be corrected to reduce spectral contributions due to the intervening skin and/or fat layers.

In sensors that include multiple long-distance sources, the electronic processor can be configured to choose a particular long-distance source for illumination of the sample. Typically, the electronic processor is configured to measure multiple absorbance spectra (either corrected or uncorrected for overlying skin and/or fat layers) of the sample, where each one of the absorbance spectra is measured following illumination of the sample by one of the long-distance sources. The processor fits each of the absorbance spectra to a Taylor series model for the primary chromophores in the sample (e.g., oxygenated and de-oxygenated hemoglobin and water). The processor then determines a root mean-square error for each fit, and selects the long-distance source that yields sample spectra with the smallest measured error, provided the sample spectra satisfy at least a minimum suitability criterion for further sample measurements. One or more absorbance spectra of the sample can then be obtained by illuminating the sample with radiation from the selected long-distance source and determining absorbance spectra based on scattered radiation from the sample.

Alternatively or in addition, to select an appropriate long-distance source, the processor can, in some embodiments, identify (e.g., measure or retrieve from a storage or memory unit) an expected spectrum of the sample and/or an expected spectral shape of particular features in the spectrum of the sample, and analyze each of the measured absorbance spectra to determine a correspondence between expected and measured spectra (or between certain portions of the expected and measured spectra). Typically, the processor then selects as the illumination source the long-distance source that produces a measured absorbance spectrum or spectral feature shape that corresponds most closely with the expected spectrum or spectral feature shape of the sample. As above, one or more absorbance spectra of the sample can then be obtained by illuminating the sample with radiation from the selected long-distance source and determining absorbance spectra based on scattered radiation from the sample.

In general, in a first aspect, the invention features sensors that include: (a) a circuit board that includes an electronic processor; (b) a plurality of radiation sources, each source being attached to the circuit board; and (c) a spectral detector attached to the circuit board, the spectral detector being configured to analyze radiation derived from one or more of the plurality of radiation sources. During use the sensor is configured to be worn on a portion of a body of a subject. Further, the electronic processor is configured to cause two or more of the plurality of radiation sources to direct incident radiation to the subject, to cause the spectral detector to analyze radiation from the subject, and to determine one or more properties of the subject based on the radiation from the subject.

In a further aspect, the invention features sensors that include: (a) a flexible mounting member that includes an adhesive surface configured to attach directly to a sample and to assume a shape corresponding to at least a portion of the sample when it attaches to the sample; and (b) a plurality of radiation sources, a spectral detector, and an electronic processor attached to the mounting member. The electronic processor can be configured to cause at least two of the radiation sources to direct incident radiation to a sample, to cause the spectral detector to analyze radiation from the sample, and to determine one or more properties of the sample based on the radiation from the sample.

In another aspect, the invention features sensors that include: (a) a plurality of radiation sources, each of the radiation sources being positioned to illuminate a sample with incident radiation; (b) a spectral detector configured to analyze radiation scattered from the sample in response to incident radiation; and (c) at least one electronic processor configured to select one of the plurality of radiation sources and to measure an absorbance spectrum of the sample based on incident radiation from the selected radiation source. Selecting one of the plurality of radiation sources can include measuring a plurality of sample absorbance spectra, each absorbance spectrum corresponding to illumination of the sample by one of the plurality of radiation sources, and determining a correlation between an expected shape and a measured shape of a spectral feature in each of the plurality of absorbance spectra.

In a further aspect, the invention features sensors that include: (a) a circuit board including at least one electronic processor; (b) a radiation source attached to the circuit board; (c) and a plurality of spectral detectors attached to the circuit board, each spectral detector being configured to analyze radiation derived from the radiation source. The electronic processor(s) can be configured to cause the radiation source to direct incident radiation to a sample, to cause two or more of the plurality of spectral detectors to analyze radiation scattered from the sample, and to determine one or more properties of the sample based on the scattered radiation.

In another aspect, the invention features sensors that include a disposable mounting member configured to attach directly to a sample and to assume a shape corresponding to at least a portion of the sample, and a plurality of radiation sources, a spectral detector, and at least one electronic processor attached to the mounting member. The electronic processor(s) can be configured to cause two or more of the plurality of radiation sources to direct incident radiation to a sample, to cause the spectral detector to analyze radiation scattered from the sample, and to determine one or more properties of the sample based on the scattered radiation.

In a further aspect, the invention features apparatus that include a wearable assembly including an integrated circuit board and, attached to the circuit board, a plurality of radiation sources, a spectral detector, and at least one electronic processor. During operation, the assembly is worn on a portion of a body of a human being. The electronic processor is configured to cause at least some of the plurality of radiation sources to direct radiation to be incident on the portion of the body, to direct the detector to analyze scattered radiation from the portion of the body, and to determine one or more properties of the portion of the body based on the scattered radiation.

Embodiments of the sensors and/or apparatus can include one or more of the following features.

The electronic processor can be configured to selectively adjust at least one of the radiation sources to produce the incident radiation. The electronic processor can be configured to selectively adjust at least one of (i) a duty cycle of, and (ii) an electrical drive current supplied to, each of the radiation sources to produce incident radiation having a selected spectral shape. The electronic processor can be configured to adjust the radiation sources to compensate for absorption of incident radiation by the subject, where the compensation includes adjusting the radiation sources based on an absorbance spectrum of the subject. The electronic processor can be configured to adjust the radiation sources to (i) correct for different emission intensities among the radiation sources, or (ii) to correct for variations in spectral detection efficiency by the detector. The electronic processor can be configured to adjust each of the radiation sources so that each of the radiation sources has a selected spectral profile.

The radiation sources can include a short-distance source positioned at a distance of 9 mm or less from the detector, and at least two long-distance sources each positioned at a distance of 10 mm or more from the detector. The radiation sources can include at least two short-distance sources and at least three long-distance sources.

The electronic processor can be configured to select one of the long-distance sources to produce at least a portion of the incident radiation by illuminating the subject with incident radiation produced by each of the long-distance sources, measuring an absorbance spectrum of the subject corresponding to illumination by each of the long-distance sources, and comparing the measured absorbance spectra to select one of the long-distance sources. The comparing can include: (a) for each of the long-distance sources, fitting the absorbance spectrum corresponding to the long-distance source to a Taylor series model for the subject's absorbance spectrum, and determining an average error between the absorbance spectrum and the model; and (b) selecting the long-distance source corresponding to a smallest average error between the absorbance spectrum and the model. The comparing can include, prior to fitting the absorbance spectra corresponding to the long-distance sources, normalizing the absorbance spectra. The comparing can include, prior to fitting the absorbance spectra corresponding to the long-distance sources, correcting each of the absorbance spectra corresponding to the long-distance sources to reduce spectral effects due to layers of skin and fat in the subject using information derived from an absorbance spectrum obtained by exposing the subject to radiation from the short-distance source.

Selecting the long-distance source can include determining whether the selected long-distance source satisfies a minimum suitability criterion. Determining whether the selected long-distance source satisfies a minimum suitability criterion can include determining an average value ($\mu$) and a standard deviation ($\sigma$) of model fitting errors, where the electronic processor can be configured to select the long-distance source if an average error between the model and an absorbance spectrum corresponding to the selected long-distance source is within an interval $(\mu-3\sigma, \mu+3\sigma)$.

The sensors can include radiation sources that include two or more short-distance sources, and the electronic processor can be configured to select a combination of a short-distance source and a long-distance source to produce at least a portion of the incident radiation by: (a) illuminating the subject with incident radiation produced by each of the short-distance sources; (b) measuring absorbance spectra corresponding to each of the short-distance sources; (c) correcting each of the spectra corresponding to the long-distance sources with each of the spectra corresponding to the short-distance sources; (d) fitting the corrected spectra to a Taylor series model for the subject's absorbance spectrum and determining a fitting error between each of the corrected spectra and the model; and (e) identifying a combination that includes a short-distance source and a long-distance source that corresponds to a smallest fitting error among the corrected spectra.

The electronic processor can be configured to measure a corrected absorbance spectrum of the subject by measuring a first absorbance spectrum of the subject based on radiation from the sample derived from illumination of the subject by one of the long-distance sources, measuring a second absorbance spectrum of the subject based on radiation from the sample derived from illumination of the subject by one or more of the short-distance sources, and correcting the first absorbance spectrum based on the second absorbance spectrum.

The sensors can include a non-disposable portion and a disposable portion, wherein the disposable portion contacts the non-disposable portion and comprises a flexible layer having an adhesive surface configured to attach directly to the sample. The sensors can include a short-distance radiation source positioned on the non-disposable portion of the sensor, and two or more long-distance radiation sources positioned on the disposable portion of the sensor.

The sensors can include a display unit, where the display unit is positioned on a surface of the sensor opposite to a surface through which the incident radiation is emitted by the plurality of radiation sources. The display unit can be configured to display values of at least some of the one or more properties of the subject. The display can be further configured to display previously measured values of the one or more properties of the subject.

The sensors can include a communication interface that includes a wireless transmitter and receiver configured to transmit data to and from the sensor, where the sensor is configured to transmit the data over a network.

The one or more properties can include at least one of oxygen saturation, oxygen tension, pH, hematocrit, hemoglobin concentration, anaerobic threshold, water content, and oxygen consumption of the subject.

The electronic processor can be configured to maintain a non-zero measured detector signal intensity within a predetermined range of signal intensities during analysis of the radiation from the subject. Maintaining the detector signal intensity within a predetermined range can include adjusting at least one of an electronic gain of the detector and a signal acquisition time to control the signal intensity. Maintaining the detector signal intensity within a predetermined range can include selecting a different one of the plurality of radiation sources to direct incident radiation to the subject. Selecting a different one of the plurality of radiation sources can include selecting a different radiation source from among the radiation sources positioned at a distance of 10 mm or more from the detector. Selecting a different one of the plurality of radiation sources can include selecting a different radiation source from among the radiation sources positioned at a distance of 9 mm or less from the detector.

The electronic processor can be configured to provide information about the one or more properties of the subject to a therapeutic device to control the therapeutic device.

The mounting member can include a first disposable portion that contacts the sample, and a second non-disposable portion to which the plurality of radiation sources, the detector, and the electronic processor are attached, where the disposable portion is at least partially transmissive to near-infrared radiation and forms a window through which incident radiation produced by the radiation sources passes to reach the sample.

In some embodiments, the plurality of radiation sources can be directly attached to the circuit board. In certain embodiments, the plurality of radiation sources can be fixedly attached to the circuit board. In some embodiments, the plurality of radiation sources can be attached to the circuit board so that during use, the plurality of radiation sources directly contact the subject, or directly contact a layer of material (e.g., an adhesive layer) positioned between the sensor and the subject. The radiation sources can be directly electrically contacted to the circuit board.

In certain embodiments, the sensors can include a plurality of spectral detectors and one or more radiation sources.

The sensors can include a power source attached to the circuit board. The power source can include a battery. The battery can be one of a rechargeable battery and a disposable battery. For example, the battery can be a rechargeable battery, and the sensor can include an apparatus configured to support the sensor during charging of the battery.

The sensors can be configured to be attached directly to the sample. At least a portion of the sensor can be flexible, and the sensor can be configured to adapt to a shape of the sample.

The detector can include a charge coupled device. Alternatively, or in addition, the detector can include a complementary metal oxide semiconductor-based device. The detector can include a linear variable filter.

A maximum dimension of the sensor can be less than 15 cm (e.g., less than 8 cm). A full width at half maximum (FWHM) spectral resolution of the detector can be 10.0 nm or less (e.g., 2.0 nm or less, 0.5 nm or less).

At least some of the plurality of radiation sources can include light emitting diodes. For example, each one of the plurality of radiation sources can include one or more light emitting diodes. At least some of the plurality of radiation sources can include multiple light emitting diodes. Alternatively, or in addition, at least some of the plurality of radiation sources can include incandescent sources.

Radiation emitted by the light emitting diodes can include near-infrared radiation. The near-infrared radiation can include radiation that includes wavelengths between 600 nm and 1100 nm. The multiple light emitting diodes can be configured to produce incident radiation having a full width at half maximum (FWHM) spectral bandwidth of 25 nm or more (e.g., 100 nm or more, 500 nm or more).

The electronic processor(s) can be configured to selectively adjust at least some of the light emitting diodes to produce the incident radiation. Selectively adjusting at least some of the light emitting diodes can include adjusting an intensity of radiation emitted by the light emitting diodes. The light emitting diodes can be adjusted by adjusting a duty cycle of the light emitting diodes. The light emitting diodes can be adjusted by adjusting a drive current supplied to the light emitting diodes. The light emitting diodes can be adjusted to increase or decrease a total output radiation intensity from the plurality of radiation sources.

The light emitting diodes can be adjusted to compensate for absorbance of incident radiation by the sample. The compensation for absorbance can include adjusting at least some of the light emitting diodes based on selected absorbance bands within a radiation absorbance spectrum of the sample. The electronic processor(s) can be configured to adjust an output intensity of at least some of the multiple light emitting diodes to produce incident radiation having a selected spectral shape. The spectral shape of the incident radiation can be selected to at least partially correct for absorption of the incident radiation by the sample. The spectral shape of the incident radiation can be selected to at least partially correct for differing emission intensities among the multiple light emitting diodes. The spectral shape of the incident radiation can be selected to at least partially correct for variations in spectral detection efficiency by the detector.

At least some of the radiation sources can include short-distance sources positioned at a distance of 9 mm or less from the detector (e.g., 8 mm or less, 7 mm or less, 6 mm or less, 5 mm or less, 4 mm or less, 3 mm or less, 2.5 mm or less from the detector). The sensor can include one or more short-distance sources (e.g., two or more short-distance sources, three or more short-distance sources, five or more short-distance sources, seven or more short-distance sources, more than seven short-distance sources).

At least some of the radiation sources can include long-distance sources positioned at a distance of 10 mm or more from the detector (e.g., 20 mm or more from the detector, 50 mm or more from the detector). Each of the long-distance sources can be positioned at a different distance from the detector relative to the other long-distance sources.

At least some of the plurality of radiation sources can include packages that include multiple radiation emitting elements. The at least some of the plurality of radiation sources each can include two or more packages. At least some of the packages can include two or more radiation emitting elements.

The electronic processor(s) can be configured to select one of two or more long-distance sources to produce incident radiation. The electronic processor(s) can be configured to select the long-distance source based on a spectral feature in an absorbance spectrum of the sample, or to select the long-distance source based on a correlation between an expected shape and a measured shape of an absorption band in a spectrum of the sample. The measured shape of the absorption band can be determined by directing incident radiation from the long-distance source to the sample and measuring radiation scattered from the sample.

In additional embodiments, the electronic processor(s) can be configured to select the long-distance source by illuminating the sample with incident radiation produced by each of the long-distance sources, measuring an absorbance spectrum of the sample based on the incident radiation from each of the long-distance sources, and comparing the absorbance spectra to select one of the long-distance sources. The comparing can include: (i) for each of the long-distance sources, fitting the absorbance spectrum corresponding to the long-distance source to a model (e.g., a Taylor series model, or another type of model) for the absorbance spectrum, and determining errors between the absorbance spectrum and the model; and (ii) selecting the long-distance source corresponding to the smallest average error between the absorbance spectrum and model. The comparing can also include, prior to the fitting, correcting each of the spectra corresponding to the long-distance sources based on absorbance information measured by illuminating the sample with incident radiation produced by one or more of the short-distance sources. In other embodiments, the comparing can also include selecting a long-distance source for which an error between the corresponding spectrum and the model satisfies a minimum suitability criterion. The minimum suitability criterion can include the spectrum having an error relative to the model that is within $3\sigma$ of a mean value of the errors.

In yet other embodiments, the electronic processor(s) can be configured to measure a corrected absorbance spectrum of the sample by measuring a first absorbance spectrum of the sample based on scattered illumination radiation derived from one of the long-distance sources, measuring a second absorbance spectrum of the sample based on scattered illumination radiation derived from one or more of the short-distance sources, and correcting the first absorbance spectrum based on the second absorbance spectrum. The first absorbance spectrum can be corrected to reduce the spectral effects of skin pigmentation in the sample. Alternatively, or in addition, the first absorbance spectrum can be corrected to reduce the spectral effects of fat in the sample.

The electronic processor(s) can also be configured to measure at least three corrected absorbance spectra of the sample based on scattered illumination radiation from at least three of the long-distance sources.

In certain embodiments, the sensors can include an adhesive element positioned to attach the sensor to the sample. The adhesive element can be disposable. In other embodiments, the sensors can be disposable or non-disposable. Alternatively, the sensors can include a non-disposable portion and a disposable portion connected to the non-disposable portion.

The plurality of radiation sources can include one or more short-distance radiation sources and one or more long-distance radiation sources relative to the position of the detector, and each of the short-distance sources can be positioned on the non-disposable portion and each of the long-distance sources can be positioned on the disposable portion. The sensors can include a power source including a disposable battery, where the disposable battery is positioned on the disposable portion. Alternatively, the sensors can include a power source including a disposable battery, where the disposable battery is positioned on the non-disposable portion.

In various embodiments, the sensors can include a sleeve configured to attach to the sample, the sleeve including a pocket configured to accommodate the sensor. The sleeve can be at least partially transmissive of near-infrared radiation.

The sensors can include a display unit. The display unit can be positioned on a surface of the sensor opposite to a surface through which the incident radiation is emitted by the plurality of radiation sources.

In certain embodiments, the sensors can include, or also include, a communication interface. The communication interface can include a wireless transmitter and receiver configured to transmit data from, and receive data sent to, the sensor. The communication interface can include a port configured to transmit data from, and receive data sent to, the sensor. The sensors can be configured to transmit data to an external device through the communication interface. The sensors can be configured to transmit data to a network through the communication interface. The network can be the internet. The network can be a mobile telephone network. The support apparatus can include a communication interface, and the sensors can be configured to transmit data to the support apparatus during charging of the battery.

The one or more properties can include at least one of oxygen saturation, oxygen tension, pH, hematocrit, hemoglobin concentration, anaerobic threshold, water content, and oxygen consumption of the sample. The sample can include muscle tissue. The sample can include a portion of a human or an animal. The sample can include skin and fat layers positioned between the sensor and the muscle tissue.

The sensors can include a housing that encloses the circuit board, the plurality of radiation sources, and the detector, where the housing is configured to attach to a subject that includes the sample.

The sensors can be configured to transmit to an external system values of at least one of oxygen saturation, oxygen tension, pH, water content, and hematocrit, and the external system can be configured to control the at least one of oxygen saturation, oxygen tension, pH, water content, and hematocrit in a subject that includes the sample.

In various embodiments, selecting one of the plurality of radiation sources can include illuminating the sample with incident radiation produced by each of the plurality of sources, measuring an absorbance spectrum of the sample based on the incident radiation from each of the sources, and comparing the absorbance spectra to select one of the sources.

Selecting one of the plurality of radiation sources can include selecting a radiation source that corresponds to a closest correlation between the expected shape and the measured shape of the spectral feature. The spectral feature can be an absorption band.

Embodiments of the sensors and/or apparatus can also include any of the other features disclosed herein, as appropriate.

In another aspect, the invention features methods for measuring one or more sample properties, the methods including selecting one of a plurality of radiation sources and directing radiation from the selected source to be incident on the sample, detecting radiation from the sample, and determining the one or more sample properties based on the detected radiation. The selecting includes: (a) for each one of the plurality of radiation sources, measuring an absorbance spectrum of the sample by exposing the sample to radiation from the radiation source; (b) fitting the absorbance spectra to a model for absorbance of the sample, and determining an average fitting error for each spectrum relative to the model; and (c) selecting the source that corresponds to the spectrum with the smallest average fit error.

Embodiments of the methods can include one or more of the following features.

The model can be a Taylor series model. The selecting can include normalizing each of the absorbance spectra prior to determining the average fitting errors. The selecting can include correcting each of the absorbance spectra to reduce spectral effects due to skin and fat layers in the sample prior to determining the average fitting errors. The selecting can include determining an average value $\mu$ and a standard deviation value $\sigma$ related to the fitting errors, and selecting a source for which the average fitting error determined from the absorbance spectrum corresponding to the source is within an interval $(\mu-3\sigma, \mu+3\sigma)$.

The methods can include, during the detection of radiation from the sample, maintaining an intensity of a detected radiation signal greater than zero and within a predetermined range of signal intensities. Maintaining the signal intensity within a predetermined range can include adjusting at least one of an electronic gain of the detector and a signal acquisition time during which the radiation is detected to control the signal intensity. Maintaining the signal intensity within a predetermined range can include selecting a different one of the plurality of radiation sources to direct radiation to the sample.

The methods can include transmitting to an external system values of at least one of oxygen saturation, oxygen tension, pH, water content, and hematocrit, where the external system is configured to control the at least one of oxygen saturation, oxygen tension, pH, water content, and hematocrit in a subject that includes the sample.

Embodiments of the methods can also include any of the other steps and/or features disclosed herein, as appropriate.

The various embodiments of the disclosure can include one or more of the following advantages.

In some embodiments, the sensors disclosed herein do not use optical fibers to couple incident radiation from illumination sources to the sample and/or to couple scattered radiation from the sample to the detector. Typically, optical fibers can be fragile and are subject to breakage during use. Manufacturing optical fibers to exacting tolerances can be difficult, time-consuming, and expensive. Further, sensors that include optical fiber coupling of radiation between sources, the sample, and the detector, may benefit from periodic recalibration to account for degradation of the optical fibers over time. The sensors disclosed herein couple radiation from sources to the sample and from the sample to the detector through the sample, through air, and through various bulk optical elements. These radiation propagating media are not subject to the same manufacturing limitations, costs, and degradation that can be typical of optical fibers.

In certain embodiments, the sensors disclosed herein include all solid-state components, including both electronic and optical components. As a result, the components can typically be manufactured reliably and/or cheaply, in large production runs if necessary. Mass production of the components can yield sensors which are inexpensive enough to be partially or completely disposable following use. In some embodiments, for example, the sensors are attached to a body part using an adhesive pad that is disposable. In certain embodiments, the entire sensor is formed as a sealed one-piece unit, and is disposable after use. In some embodiments, a portion of the sensor (e.g., a portion that includes the long-distance illumination sources only) is disposable, while the remainder of the sensor is reusable.

In some embodiments, some or all of the sensor's radiation sources include multiple light emitting diodes (LEDs), and the sensor's electronic processor can adjust the integrated output intensity of some or all of the LEDs to generate incident radiation having selected spectral properties. For example, the intensities of some or all of the LEDs can be adjusted to compensate for: stronger absorption of incident radiation at certain wavelengths than others by the sample; variable wavelength-dependent detection efficiency in the detector; and variable wavelength- and diode-dependent emission intensities. As a result, the spectral properties of the incident radiation can be adjusted to provide enhanced sensitivity in portions of the electromagnetic spectrum in which the sample strongly absorbs incident radiation.

Typically, the sensors include multiple LEDs that are configured to collectively emit incident radiation having a relatively broad bandwidth. Accordingly, the spectral detector can be configured to sample scattered radiation at a relatively large number of wavelengths, and can therefore provide relatively high spectral resolution. In addition, because absorbance spectra of the sample can be determined at a relatively large number of wavelengths, the absorbance spectra can be corrected to reduce and/or remove spectral contributions that arise from skin and fat layers in the sample.

In certain embodiments, the sensors include a spectral detector that includes a linear variable filter (LVF) or a variable Fabry Perot etalon (FPE), which have relatively high temperature stability. For example, due to the construction of the LVF, the temperature stability of the LVF is typically higher than the temperature stability of certain other types of spectral detectors such as grating-based systems. As a result, the sensors disclosed herein can typically be used over a wide range of temperatures without having to re-calibrate the detector.

The sensors disclosed herein can be portable and even wearable, and can include a circuit board upon which are mounted sensor components including multiple radiation sources, a spectral detector, an electronic processor, a communication interface, and a power source. As a result, the sensors can be worn under clothing or as part of clothing, and can be used in environments such as during athletic training, in patient monitoring, in rehabilitation and field medicine, and during patient transport, with relatively little disruption or burden imposed upon the wearer. The sensors can also be worn by animals, with comparatively little discomfort relative to more conventional monitoring devices.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

FIGS. 1A and 1B are bottom and top schematic diagrams, respectively, of an embodiment of a sensor.

FIG. 1C is a bottom schematic diagram of another embodiment of a sensor.

FIG. 2 is a schematic diagram showing a sensor attached to a surface of a sample.

FIG. 23 is a plot of oxygen saturation as a function of time derived from the reflectance spectra of FIG. 22 during the blood occlusion test protocol.

FIG. 24 is a graph showing predicted reflected radiation intensity as a function of fat thickness for a series of tissue phantoms.

Like reference symbols in the various drawings indicate like elements.

DETAILED DESCRIPTION

Figure 3A:
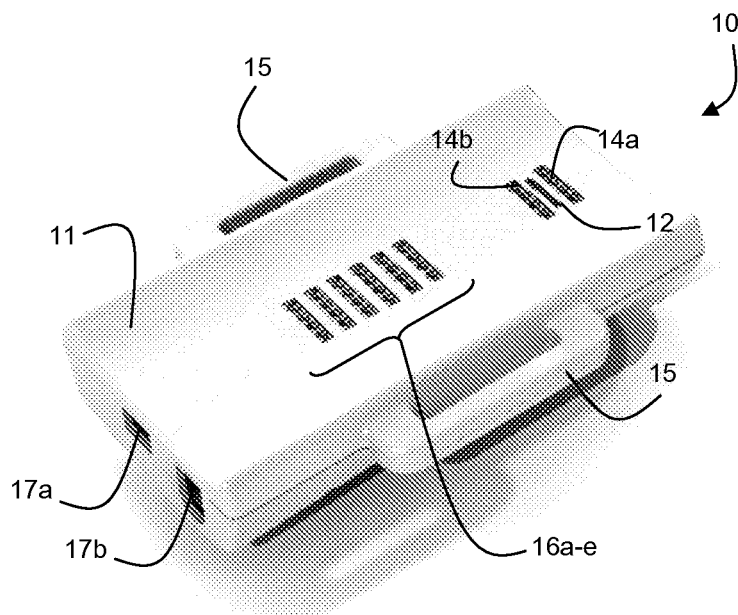
FIGS. 3A and 3B are views of a sensor showing the sensor housing.

Disclosed herein are sensors and associated methods for determining properties of samples including, in particular, human subjects. The sensors are typically, but not exclusively, configured to measure near-infrared absorbance or reflectance spectra from the samples, and to calculate one or more sample parameters based on the absorbance or reflectance spectra. The sensors are relatively small, and can include a circuit board upon which are mounted all sensor components. As a result, the sensors are particularly amenable to prolonged wear by a human subject, even during periods of relatively high physical stress.

FIGS. 1A and 1B are schematic diagrams showing bottom and top surfaces, respectively, of a sensor 10. Sensor 10 includes a spectral detector 12, two short-distance radiation sources 14a and 14b, and six long-distance radiation sources 16a, 16b, 16c, 16d, 16e, and 16f. Detector 12 and radiation sources 14a-b and 16a-f are mounted to circuit board 18. Each of short-distance radiation sources 14a and 14b can include one or more packages, and each package can include one or more elements that produce illumination radiation. Similarly, each of long-distance radiation sources 16a-f can include one or more packages, and each package can include one or more elements that produce illumination radiation.

While FIGS. 1A and 1B show an embodiment of sensor 10 that includes two short-distance sources 14a and 14b and six long-distance sources 16a-f, more generally, sensor 10 can include any number of short-distance radiation sources and any number of long-distance radiation sources. For example, in some embodiments, sensor 10 can include one or more short-distance radiation sources (e.g., two or more short-distance radiation sources, three or more short-distance radiation sources, four or more short-distance radiation sources, five or more short-distance radiation sources, six or more short-distance radiation sources, eight or more short-distance radiation sources, or even more short-distance radiation sources). In certain embodiments, sensor 10 can include one or more long-distance radiation sources (e.g., two or more long-distance radiation sources, three or more long-distance radiation sources, four or more long-distance radiation sources, five or more long-distance radiation sources, six or more long-distance radiation sources, eight or more long-distance radiation sources, or even more long-distance radiation sources).

The short- and long-distance sources in sensor 10 can be directly attached to circuit board 18. That is, the sources can be mounted directly to circuit board 18, rather than being connected to circuit board 18 via electrical wires or cables, or optical fibers. In some embodiments, the short- and long-distance sources can be soldered directly to circuit board 18 (e.g., with no spacer or other element separating the sources and circuit board 18). In certain embodiments, the short- and long-distance sources can also be fixedly attached to circuit board (e.g., mounted on circuit board 18 such that a fixed spatial relationship exists between the sources and circuit board 18). By virtue of the fixed attachment, the sources do not move independently of circuit board 18, as would occur if the sources were attached with a cable or fiber. Instead, the sources are rigidly attached to circuit board 18 so that the position of the sources with respect to circuit board 18 does not change.

In general, each of the short-distance and long-distance radiation sources can include one or more packages (e.g., two or more packages, three or more packages, four or more packages, five or more packages, six or more packages, or even more packages). Each of the packages can include one or more elements that produce illumination radiation (e.g., two or more elements, three or more elements, four or more elements, or even more elements). Further, elements that emit radiation at different wavelengths can be positioned at different spatial locations, depending upon the sample the detector. For example, if detector 12 is configured to resolve different wavelengths at different spatial positions, the elements and/or packages in some or all of the short- and long-distance sources can be positioned to correspond directly or opposingly to the configuration of detector 12.

In some embodiments, the number of packages in some of the short- and/or long-distance radiation sources can vary. For example, sources that are positioned further from detector 12 can include larger numbers of packages, to ensure that sufficient scattered radiation intensity is measured by detector 12. In general, any of the short- and/or long-distance sources can include any number of packages, the number of packages being selected to ensure that the sample is sufficiently illuminated with a desired distribution of incident radiation, and to ensure that detector 12 obtains suitable measurements of scattered radiation from the sample. As an example, in some embodiments, a long-distance source that is positioned furthest from detector 12 can include 1.5 times as many packages (e.g., 2.0 times as many packages, 2.5 times as many packages, 3.0 times as many packages, 3.5 times as many packages, 4.0 times as many packages as a long-distance source that is positioned nearest to detector 12.

The elements within the packages of each short- and long-distance radiation source are typically selected so that, when the elements are activated (e.g., emitting light), the spectrum of the light produced collectively by the elements corresponds to a desired spectral distribution of illumination radiation. The spectral distribution can be altered by positioning particular elements within the short- and/or long-distance sources, so that the sample can be illuminated according to specific spectral distributions. In some embodiments, for example, the illumination spectrum for one or more short- and/or long-distance sources can be selected so that measurement sensitivity of sensor 10 in particular regions of the spectrum is enhanced, as discussed previously.

As shown in FIG. 1A, the emission windows of radiation sources 14a-b and 16a-f, and the radiation entry surface of detector 12, are exposed on the bottom surface of sensor 10.

Sensor 10 also includes an electronic processor 20, an optional applications processor 22, an optional display unit 24, a power source 26, and a communication interface 28. Processors 20 and 22, display 24, power source 26, and interface 28 are mounted to the upper surface of circuit board 18, as shown in FIG. 1B. In some embodiments, processor 22 is not included in sensor 10; instead, processor 22 is part of an external computing device (e.g., a personal computer) that communicates with sensor 10 via communication interface 28, and performs some or all of the functions of processor 22 (or processor 20) disclosed herein.

In some embodiments, some (or all) of the long-distance radiation sources can be mounted on a separate circuit board that interfaces to circuit board 18 via a suitable connector. FIG. 1C shows a schematic diagram of the bottom of a sensor 10 that includes a first circuit board 18 and a second circuit board 19. First circuit board 18 includes detector 12 and two short-distance sources 14a-b. Second circuit board 19 includes five long-distance sources 16a-e. A connector 21 connects the first and second circuit boards, and permits communication (e.g., exchange of data and control signals) between the circuit boards. Typically, for example, processor 20 (and, optionally, processor 22) are located on first circuit board 18, and communicate with long-distance sources 16a-e via connector 21.

In certain embodiments, power source 26 is mounted on first circuit board 18, and can also communicate with sources 16a-e via connector 21. Power source 26 can include, for example, a rechargeable battery. In some embodiments, power source 26 can include a disposable battery. In the embodiment shown in FIG. 1C for example, the disposable battery can be positioned on or connected to first circuit board 18. Alternatively, the disposable battery can be positioned on or connected to second circuit board 19. If second circuit board 19 is a disposable circuit board, the battery can be disposed of at the same time as second circuit board 19.

FIG. 2 shows a schematic diagram of sensor 10 mounted on a sample 30. Sample 30 includes one or more layers of skin 32, a subcutaneous layer of fat 34, and underlying muscle tissue 36. Sensor 10 is configured to interrogate muscle tissue 36 by directing radiation 38, generated by at least one (e.g., all) of radiation sources 14a-b and at least one of the radiation sources 16a-f, to be incident on muscle tissue 36. Scattered radiation 40 is received and analyzed by detector 12 (not shown) to determine a spectrum of the scattered radiation. The scattered radiation spectrum is then processed by electronic processor 20 and/or processor 22 (not shown) to determine an absorbance spectrum of muscle tissue 36. Based on the absorbance spectrum, electronic processor 20 and/or 22 can determine one or more properties of sample 30 (and in particular, of muscle tissue 36 within sample 30).

In general, the scattered radiation spectrum measured by detector 12, which typically includes wavelength-dependent information about scattered radiation from sample 30, can be converted by an electronic processor to an absorbance spectrum of muscle tissue 36 using well-known methods. As noted previously, in the following discussion, reference is made to absorbance spectra of samples such as sample 30. However, the apparatus and methods disclosed herein can also be used to derive reflectance spectra from measured scattered radiation; reflectance and absorbance are related by a simple mathematical transformation. Methods for converting spectral scattered radiation information into reflectance and absorbance spectra for a sample are disclosed, for example, in U.S. Patent Application Publication No. US 2008/0097173.

In addition to converting scattered radiation information into absorbance and/or reflectance spectra, processor 20 and/or 22 can be configured (e.g., using calibration equations and/or data stored in memory units, magnetic storage units, and/or optical storage units) to analyze absorbance spectra to obtain measurements of physiologically important parameters for sample 30. In general, processor 20 and/or 22 can be configured to perform any of the analysis steps that are discussed herein.

In some embodiments, one or more absorbance spectra for sample 30 can be analyzed to determine pH (e.g., muscle tissue pH) in the sample. Systems and methods for determining tissue pH are disclosed, for example, in U.S. Pat. No. 5,813,403 entitled "Optical Measurement of Tissue pH," the entire contents of which are incorporated herein by reference.

In certain embodiments, one or more absorbance spectra for sample 30 can be analyzed to determine blood hematocrit in the sample. Systems and methods for determining blood hematocrit are disclosed, for example, in U.S. Pat. No. 6,006,119 entitled "Noninvasive Optical Measurement of Blood Hematocrit," the entire contents of which are incorporated herein by reference.

In some embodiments, one or more absorbance spectra for sample 30 can be analyzed to determine quantities such as hemoglobin concentration, and/or water content, and/or oxygen tension and/or tissue oxygen saturation. Systems and methods for determining these quantities are disclosed, for example, in U.S. Patent Application Publication No. US 2008/0097173, and in U.S. Pat. No. 6,766,188, the entire contents of each of which are incorporated herein by reference.

In certain embodiments, one or more absorbance spectra for sample 30 can be analyzed to determine quantities such as anaerobic threshold and/or metabolic rate (e.g., oxygen consumption rate) in the sample. Systems and methods for determining these quantities are disclosed, for example, in U.S. patent application Ser. No. 12/172,942, entitled "Physical Performance Monitoring and Monitors," filed on Jul. 14, 2008, the entire contents of which are incorporated herein by reference.

In some embodiments, one or more absorbance spectra for sample 30 can be analyzed to determine additional quantities such as a temperature of a tissue of interest within sample 30. In addition, processor 20 and/or 22 can include a hardware-based temperature monitor that effectively monitors a temperature of the sample surface to which sensor 10 is attached, for example.

Figure 3B:
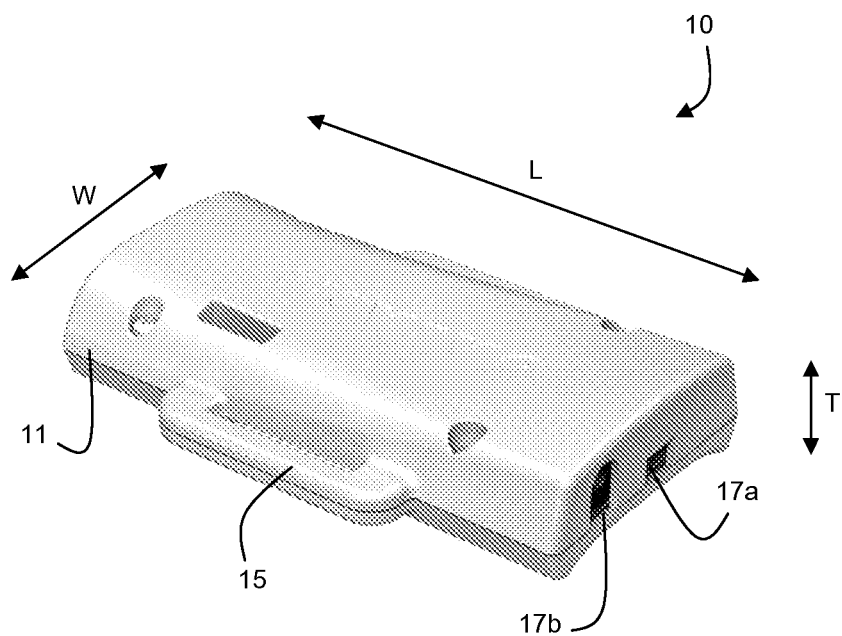

Typically, sensor 10 includes a housing that encloses components such as circuit board 18, and which also includes apertures that permit radiation generated by the short- and long-distance sources to emerge from the housing, and permit scattered radiation from the sample to be incident on detector 12. FIGS. 3A and 3B show bottom and top views, respectively, of a sensor 10 that includes a housing 11. Apertures formed in the bottom surface of housing 11 expose long-distance sources 16a-e, short-distance sources 14a-b, and detector 12, as shown in FIG. 3A. Apertures 17a and 17b, formed in a side surface of housing 11, permit connection to communication interface 28 and power source 26, respectively. Loops 15 admit a fastener such as a strap (e.g., a Velcro™ strap or another type of strap) to secure housing 11 to a sample (e.g., an arm or leg of a subject).

Typically, the dimensions of sensor 10 are smaller than corresponding dimensions of conventional spectral devices. With reference to FIG. 3B, the housing of sensor 10 includes a bottom surface that has a maximum dimension L, a maximum width W measured in a direction perpendicular to the maximum dimension L, and a thickness T measured in a direction perpendicular to both the maximum dimension L and the maximum width W.

The dimensions L, W, and T of sensor 10 can vary according to the various components included in sensor 10 (e.g., numbers and spatial positions of radiation sources, processors, display unit, power source). In the embodiment shown in FIGS. 3A and 3B, the dimensions L, W, and T are approximately 110 mm, 55 mm, and 20 mm, respectively.

In general, however, the dimensions L, W, and T of sensor 10 can differ in various embodiments. In some embodiments, the maximum dimension L can be 15 mm or more (e.g., 20 mm or more, 30 mm or more, 40 mm or more, 50 mm or more, 60 mm or more, 70 mm or more, 80 mm or more) and/or 150 mm or less (e.g., 140 mm or less, 130 mm or less, 120 mm or less, 110 mm or less, 100 mm or less, 90 mm or less). In certain embodiments, the maximum width W can be 10 mm or more (e.g., 15 mm or more, 20 mm or more, 25 mm or more, 30 mm or more, 35 mm or more, 40 mm or more) and/or 75 mm or less (e.g., 70 mm or less, 65 mm or less, 60 mm or less, 55 mm or less, 50 mm or less, 45 mm or less).

In some embodiments, the thickness T can be 5 mm or more (e.g., 10 mm or more, 15 mm or more, 20 mm or more) and/or 30 mm or less (25 mm or less). Typically, sensor 10 is sufficiently thin (e.g., thickness T is sufficiently small) so that sensor 10 can be comfortably worn by a human or animal subject without causing undue discomfort. For human subjects, such sensors can comfortably be worn underneath clothing, for example.

Figure 4:
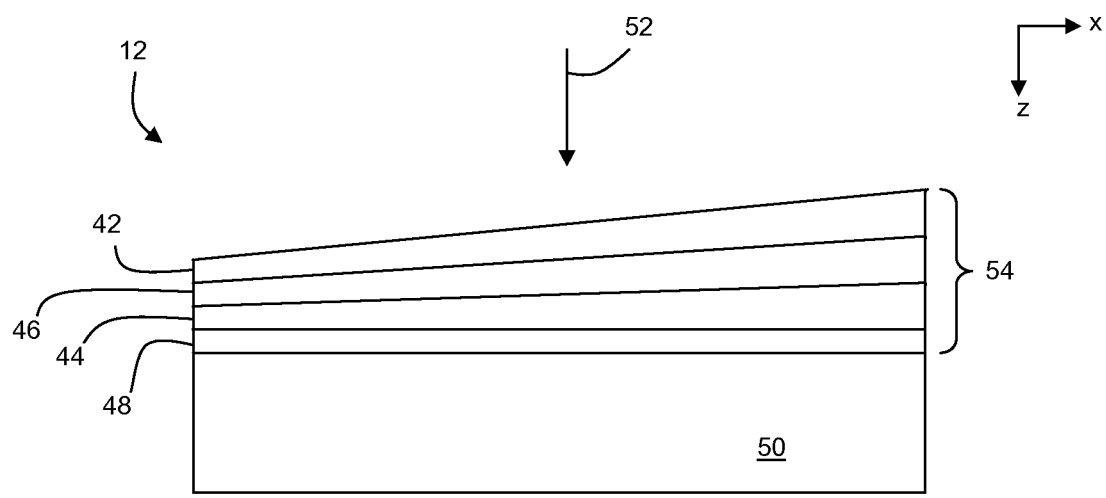
FIG. 4 is a schematic diagram showing an embodiment of a detector.

Detector 12 is a spectral detector configured to analyze input radiation as a function of wavelength. In certain embodiments, for example, detector 12 can include a linear variable filter or a variable Fabry Perot etalon (FPE) coupled to a radiation detector such as a linear photodiode array, a charge coupled device (CCD) or a complementary metal oxide semiconductor (CMOS) device. FIG. 4 is a schematic diagram of a detector 12 that includes a linear variable filter (LVF) 54 coupled to a linear array CCD detector 50. LVF 54 is essentially a wedged bandpass filter, and includes mirror layers 42 and 44, a spacer layer 46, and a substrate 48, which collectively function as an etalon or interference bandpass filter. Radiation 52 (e.g., collimated radiation) is incident on detector 12 along the z-direction shown in FIG. 4. The design, operation and function of bandpass interference filters and variable bandpass filters, such as LVFs, are disclosed, for example, in the "Interference Filter Handbook," published by JDS Uniphase (Second Edition), the entire contents of which are incorporated herein by reference.

In some embodiments, detector 12 has a length, measured in the direction of the width W of sensor 10, of 2 mm or more (e.g., 4 mm or more, 6 mm or more, 8 mm or more, 10 mm or more, 12 mm or more) and/or 20 mm or less (e.g., 18 mm or less, 16 mm or less, 14 mm or less). In certain embodiments, detector 12 has a thickness, measured in the direction of the thickness T of sensor 10, of 0.1 mm or more (e.g., 0.2 mm or more, 0.3 mm or more, 0.5 mm or more, 1.0 mm or more, 2.0 mm or more) and/or 5.0 mm or less (e.g., 4.0 mm or less, 3.0 mm or less, 2.5 mm or less).

In some embodiments, detector 12 has a width, measured in the direction of the length L of sensor 10, of 1.0 mm or more (e.g., 1.5 mm or more, 2.0 mm or more, 2.5 mm or more) and/or 4.0 mm or less (e.g., 3.5 mm or less, 3.0 mm or less).

Devices such as LVFs, FPEs, and CCD detectors are generally robust and do not appreciably degrade over time. As a result, the spectral properties of these devices typically remain relatively constant, obviating the need to perform re-calibration of detector 12 over time. In addition, LVFs, FPEs, and CCD detectors are relatively stable under the influence of temperature fluctuations. Typically, the layers of LVF 54 are formed of various amorphous or crystalline materials, which do not appreciably expand or contract with modest changes in temperature. As a result, the spectral filtering properties of LVF 54 remain relatively unchanged for modest temperature changes, and detector 12 does not typically have to be calibrated for variable temperature operation.

In general, detector 12 can include various types of spectral detectors. For example, detector 12 can include detectors that include a radiation sensitive element (e.g., photodiode array and/or CCD and/or CMOS device) coupled to a wavelength-dispersive element such as one or more diffraction gratings and/or prisms. In addition, detector 12 can include other types of dispersive and/or filtering elements (e.g., diffractive optical elements, liquid crystal-based filters, bandpass filters, tunable etalons) that are used to provide wavelength-sensitive detection and/or analysis of incoming radiation.

In certain embodiments, a full width at half maximum (FWHM) spectral resolution of detector 12 is 10.0 nm or less (e.g., 8.0 nm or less, 6.0 nm or less, 5.0 nm or less, 4.0 nm or less, 3.0 nm or less, 2.0 nm or less, 1.0 nm or less, 0.5 nm or less, 0.25 nm or less). In general, the FWHM spectral resolution depends upon the number of active detector elements (e.g., pixels on a CCD detector) and the wavelength-dispersing ability of the optical elements in the detector.

Figure 5:
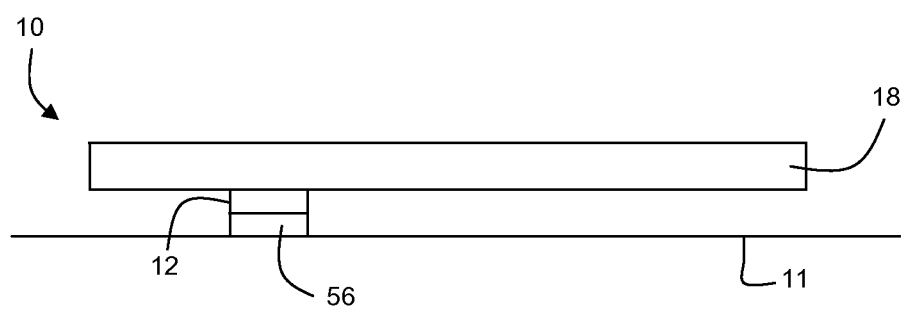
FIG. 5 is a schematic diagram showing a side view of a detector that includes a collimating element.

In some embodiments, sensor 10 can include one or more optical elements that are configured to effectively control the range of angles at which scattered radiation is incident on detector 12 from sample 30. For example, FIG. 5 shows a sensor 10 that includes a collimating element 56 attached to a surface of detector 12 (e.g., the surface of detector 12 that receives scattered radiation from sample 30). Detector 12 can include, for example, a LVF, and collimating element 56 can be attached directly to the LVF. Detector 12 can also include, for example, a CCD detector coupled to the opposite surface of the LVF. The entire assembly—collimating element 56, the LVF, and the CCD detector—can be mounted on circuit board 18, as shown in FIG. 5. Collimating element 56 functions to collimate scattered radiation 40 from sample 30 to control the range of angles at which the scattered radiation is incident on detector 12. The spectral bandpass properties of LVF 54, such as a FWHM spectral width and/or shape of a spectral passband of LVF 54, depend upon the angle of incidence of incoming radiation. In particular, variations in the angle of incidence of the scattered radiation on LVF 54 can result in blue-shifting of the passband wavelength at one or more positions along CCD detector 50, and/or loss of spectral resolution (e.g., increase of passband width) in LVF 54. By controlling the range of angles of incidence via collimating element 56, the spectral properties of detector 12 can be reproducible over relatively long periods of use.

In general, a variety of different collimating elements 56 can be used in sensor 10. Exemplary collimating elements include fiber faceplates (e.g., fiber optic windows), collimating hole devices, gradient index (GRIN) lenses, fiber bundles, lens arrays, optical windows (including shaped optical windows), and other similar devices.

Sensor 10 typically includes a plurality of radiation sources. In some embodiments, some or all of the radiation sources include light emitting diodes (LEDs). Some (or all) of the radiation sources of sensor 10 can provide relatively broad bandwidth incident radiation for illuminating sample 30. To provide such radiation, the radiation sources can include one or more LEDs. For example, in certain embodiments, some radiation sources can include a single broadband LED. In some embodiments, certain radiation sources can include multiple LEDs. The multiple LEDs can each emit radiation having different central wavelengths and/or spectral bandwidths. In some embodiments, some of the multiple LEDs can emit radiation having the same central wavelength and/or bandwidth.

In the embodiment shown in FIG. 1A, for example, each of sources 14a-b and 16a-f includes six LEDs having central emission wavelengths of 735 nm, 780 nm, 810 nm, 850 nm, 890 nm, and 940, respectively. The six LEDs together can be powered to deliver up to approximately 500 mW of total radiation power, depending upon the method used to drive/power the LEDs. In the embodiment shown in FIG. 1A, the LEDs are custom packaged as surface-mount technology devices with a width of about 2 mm. Each package can be configured to hold up to three LED dies (the radiation-emitting elements). The six LEDs are distributed among two LED packages; one package includes three LED dies, and the other includes two LED dies. The LEDs are typically powered by a regulated supply of between 3.5V and 5V from power source 26. In some embodiments, power source 26 can be a transformer block, for example, that delivers 6 V or more.

In some embodiments, any one or more of radiation sources 14*a*-*b* and 16*a*-*f* can include other types of radiation emitting elements. For example, the radiation sources can include incandescent (e.g., tungsten filament) lamps. Suitable lamps include, for example, Gilway models T-1 and T-1¼, available from International Light Technologies (Peabody, Mass.). These lamps have relatively low operating voltage (5 V), operating current (0.06 A), and can provide up to 200,000 hours of operation. In addition, the lamps can be operated at 3.5 V with relatively minor reductions in near-infrared radiation output, and with relatively large increases in stability and lifetime. Similar lamp models are also available, for example, from companies such as Welch Allyn (Skaneateles Falls, N.Y.).

In general, some or all of the radiation sources of sensor 10 can include any number of radiation emitting elements (e.g., LEDs, tungsten lamps). In some embodiments, for example, radiation sources can include one or more radiation emitting elements (e.g., two or more radiation emitting elements, three or more radiation emitting elements, five or more radiation emitting elements, seven or more radiation emitting elements, nine or more radiation emitting elements).

In some embodiments, the number of radiation emitting elements in some of the short- and/or long-distance radiation sources (and/or some of the packages within the short- and/or long-distance radiation sources) can vary. For example, sources that are positioned further from detector 12 can include packages with larger numbers of radiation emitting elements, to ensure that sufficient scattered radiation intensity is measured by detector 12. In general, any of the packages of the short- and/or long-distance sources can include any number of radiation emitting elements, the number of elements being selected to ensure that the sample is sufficiently illuminated with a desired distribution of incident radiation, and to ensure that detector 12 obtains suitable measurements of scattered radiation from the sample.

When some or all of the radiation sources of sensor 10 include multiple radiation emitting elements, electronic processor 20 can be configured to adjust the radiation emitting elements to control the properties of the output radiation produced by the multiple elements. In particular, for example, when certain radiation sources of sensor 10 include multiple LEDs, processor 20 can control the emitted radiation intensity from each of the individual LEDs to control the overall distribution of radiation produced by the sources. Control of the emitted radiation intensity can be achieved, for example, through a digital-to-analog converter (DAC) which converts a digital control signal from processor 20 and/or 22 into an analog control voltage applied to a given radiation source element. With a DAC of suitable resolution (e.g., 14-bit), relatively fine control over emission intensities of individual LEDs can be achieved, and continuous-wave emission can be implemented.

Alternatively, in some embodiments, direct digital control of individual LEDs can be achieved via pulse width modulation (PWM) of the LEDs by processor 20 and/or 22. Pulse width modulation provides a modulated (e.g., pulsed) LED output. Under PWM control, the integrated intensity of LED output over a selected temporal window is controlled, from a maximum value (always on) to zero (always off), as defined by the duty cycle of the modulated signal. Emission intensities between these limits are realized by high frequency pulsing of the LEDs by processor 20 and/or 22. By controlling the rate at which pulses are emitted by the LEDs, the duty cycle of the LEDs can be adjusted. For example, to reduce the emission intensity of a particular LED from its maximum value to a half-maximum value, the duty cycle of the LED is reduced to 50%.

In certain embodiments, the emission intensities of individual LEDs are fixed. That is, suitable emission intensities for each of the LEDs are determined based on a particular measurement application, and the current supplied to each of the LEDs to achieve the desired intensity output for each is determined (as discussed further in Example 3). After suitable driving currents for each LED have been determined, resistors can be introduced into the driving circuit for each of the LEDs to maintain an appropriate drive current for each LED. The determination of suitable drive currents (and resistors) for a particular selection of LEDs can be made once using a calibration sensor, and subsequent sensors built using the same combination of LEDs can include the set of pre-determined resistors; separate calibration of each sensor is not required.

Processor 20 and/or 22 can be configured to control the emitted radiation intensity from multiple radiation emitting elements for a variety of reasons. For example, in certain embodiments, the intensities of some of the radiation emitting elements may be higher than the intensities of others. By controlling (e.g., reducing) the intensities of certain radiation emitting elements, the spectral profile of illumination radiation directed to a sample can be made more uniform, for example, or can be modified so that the spectral profile more generally assumes a desired (and known) shape. By using illumination radiation with a known shape, it can be easier to identify spectral features of interest, for example, in measured scattered radiation from the sample.

As another example, in some embodiments, the sensitivity of detector 12 to incident radiation can vary as a function of the wavelength of the radiation. Accordingly, the spectral profile of the illumination radiation can be selected to reduce or remove spectral features in measured scattered radiation spectra that arise from such variations in detector sensitivity. As above, selecting the spectral profile of the illumination radiation can include increasing and/or decreasing emitted radiation intensity from certain radiation emitters relative to other radiation emitters under the control of processor 20 and/or 22.

As a further example, in some embodiments, the sample (e.g., sample 30) can include moieties that absorb incident radiation at one or more well-known wavelengths. To enhance a signal-to-noise ratio in measured scattered radiation (and even, to enable measurement of scattered radiation at the wavelengths of absorption), the emission intensities of certain radiation emitters can be increased and/or decreased relative to other radiation emitters. In particular, emission intensities of radiation emitters that emit radiation that falls within absorption bands can be increased relative to emission intensities of other emitters (or the intensities of the other emitters can be decreased relative to the emission intensities of the emitters that emit within the absorption bands).

Typically, for example, each radiation source of sensor 10 emits radiation that includes multiple radiation wavelengths. In some embodiments, a FWHM spectral bandwidth of the emitted radiation from each source is 10 nm or more (e.g., 15 nm or more, 20 nm or more, 50 nm or more, 100 nm or more, 200 nm or more, 300 nm or more, 400 nm or more, 500 nm or more, 700 nm or more). The usable range of the radiation emitted by each source can be determined by a transmission range of detector 12. In certain embodiments, for example, detector 12 includes a LVF with a transmission range of from 600 nm to 1100 nm. The usable range of the emitted radiation can also depend, in some embodiments, on the spectral response of a detector coupled to the wavelength dispersive element in detector 12. For example, photodiode arrays, CCD arrays, and CMOS arrays that are formed of silicon typically have a usable spectral response that reaches an upper limit at about 1100 nm. Detectors formed of other materials can be used to measure sample responses at even longer wavelengths.

In general, each radiation source of sensor 10 emits radiation having a central wavelength. The central wavelength of emitted radiation from each source can be between 600 nm and 1100 nm (e.g., between 650 nm and 1050 nm, between 700 nm and 1000 nm, between 750 nm and 1000 nm, between 800 nm and 1000 nm, between 800 nm and 1100 nm).

Each radiation source (e.g., sources 14*a-b* and 16*a-f*) includes one or more radiation emitters such as LEDs and/or tungsten filaments. The radiation emitters can all emit at the same central emission wavelength, or some of the emitters can emit at different wavelengths. Alternatively, or in addition, the radiation emitters can all have different FWHM emission bandwidths, or at least some of the emitters can have the same bandwidths.

In general, each emitter emits radiation having a central emission wavelength between 600 nm and 1100 nm (e.g., between 650 nm and 1050 nm, between 700 nm and 1000 nm, between 750 nm and 1000 nm, between 800 nm and 1000 nm, between 800 nm and 1100 nm). Typically, for example, each emitter has a FWHM emission bandwidth of 3 nm or more (e.g., 5 nm or more, 10 nm or more, 15 nm or more, 20 nm or more, 30 nm or more, 40 nm or more, 50 nm or more, 60 nm or more, 80 nm or more, 100 nm or more, 150 nm or more, 200 nm or more).

Sensor 10 includes both short-distance sources 14*a-b* and long-distance sources 16*a-f*. Short-distance sources are positioned at a distance s from detector 12, measured along the x-direction as shown in FIG. 1A. Typically, for example, s is about 2.5 mm. In general, however, can be 0.5 mm or more (e.g., 1.0 mm or more, 1.5 mm or more, 2.0 mm or more, 2.5 mm or more, 3.0 mm or more, 4.0 mm or more, 5.0 mm or more) and/or 10.0 mm or less (e.g., 9.0 mm or less, 8.0 mm or less, 7.0 mm or less, 6.0 mm or less).

As shown in FIG. 1A, in certain embodiments, sensor 10 includes two short-distance sources 14*a-b*. The number of short-distance sources is typically selected to ensure that detector 12 is relatively uniformly illuminated with scattered radiation from a sample when short-distance sources are used to illuminate the sample. Accordingly, in general, sensor 10 can include one or more short-distance sources. For example, in some embodiments, sensor 10 can include from zero to four short-distance sources positioned on one side of detector 12. From zero to four short-distance sources can also be positioned on the other side of detector 12. Each of the sources can include one or more packages, as discussed previously, and each of the packages can include one or more radiation emitting elements.

In certain embodiments—for example, where sensor 10 has an extended length L—the number of short-distance sources on each side of detector 12 can be even greater (e.g., five or more, six or more, seven or more, eight or more, nine or more, ten or more).

Sensor 10 also includes a plurality of long-distance sources 16*a-f*. In some embodiments, as shown in FIG. 1A, sensor 10 includes six long-distance sources 16*a-f*. The depth to which incident radiation from a particular radiation source penetrates a sample and generates detected scattered radiation from a tissue of interest therein is generally related to a linear distance between the radiation source and the detector. Each of the long-distance sources of sensor 10 therefore generally corresponds to interrogation of the sample to a certain depth below the sample surface. Typically, an appropriate long-distance source is selected to illuminate muscle tissue 36 in sample 30 by selecting a long-distance source that produces radiation that can penetrate through overlying layers to sufficiently illuminate muscle tissue 36 below the surface of sample 30 so that reflected light from the muscle can be adequately measured by detector 12. Sensor 10 can, in general, include any number of long-distance sources to enable measurement of tissues at a variety of depths below the surface of a sample. In certain embodiments, for example, sensor 10 can include one or more long-distance sources (e.g., two or more long-distance sources, three or more long-distance sources, four or more long-distance sources, five or more long-distance sources, seven or more long-distance sources, nine or more long-distance sources, or even more long-distance sources). All of the long-distance sources can be positioned at different distances measured along the x-direction from detector 12, as shown in FIG. 1A, or at least some of the sources can be positioned at the same distance from detector 12.

Typically, a shortest distance between any of the long-distance sources and detector 12 is d, as shown in FIG. 1A. Each of the short-distance sources is positioned at a distance less than d from detector 12, and each of the long-distance sources is positioned at a distance of d or more from detector 12, the distances being measured in the x-direction. In some embodiments, d is 5 mm or more (e.g., 6 mm or more, 8 mm or more, 10 mm or more, 12 mm or more, 14 mm or more, 16 mm or more, 18 mm or more, 20 mm or more, 22.5 mm or more, 25 mm or more, 27.5 mm or more, 30.0 mm or more, 35.0 mm or more, 40 mm or more, 50 mm or more).

Referring again to FIG. 1A, in some embodiments, a spacing h between each of the long-distances sources is the same, so that each successive long-distance source is displaced from detector 12 by an additional distance increment h. In the embodiment shown in FIG. 1A, for example, the six long-distance sources 16*a-f* are positioned at distances of 25 mm, 30 mm, 35 mm, 40 mm, and 45 mm from detector 12, respectively, measured along the x-direction.

In certain embodiments, the spacings between each of the long-distance sources are not all the same. For example, sensor 10 can include a first group of long-distance sources and a second group of long-distance sources, where each member of the first and second groups is positioned relatively closely to other members of the same group, but relatively farther away from sources in the other group.

In general, the spacing h between any two long-distance radiation source elements can be 0.5 mm or more (e.g., 1.0 mm or more, 2.0 mm or more, 3.0 mm or more, 4.0 mm or more, 5.0 mm or more, 7.5 mm or more, 10.0 mm or more, 12.5 mm or more, 15.0 mm or more, 17.5 mm or more, 20.0 mm or more, 30.0 mm or more, 40.0 mm or more, 50.0 mm or more, 60.0 mm or more, 70.0 mm or more, 100 mm or more, 150 mm or more, or even more).

Typically, short-distance sources are spaced from detector 12 by a distance s, measured along the x-direction as shown in FIG. 1A. In general, the spacing s can be 0.5 mm or more (e.g., 1.0 mm or more, 2.0 mm or more, 3.0 mm or more, 4.0 mm or more, 6.0 mm or more, 8.0 mm or more, 10.0 mm or more, 15.0 mm or more, 20.0 mm or more, or even more). When multiple short-distance sources are implemented in sensor 10, the multiple short-distance sources can be evenly spaced along the x-direction, or the spacings between some or all short-distance sources can differ. In general, the spacing between any two short-distance sources can be 0.5 mm or more (e.g., 1.0 mm or more, 2.0 mm or more, 3.0 mm or more, 4.0 mm or more, 6.0 mm or more, 8.0 mm or more, 10.0 mm or more, 15.0 mm or more, 20.0 mm or more, or even more).

In some embodiments, circuit board 18 can be flexible and can deform when attached to the surface of a sample, assuming a shape that is at least partially complementary to a shape of the sample. In certain embodiments, for example, circuit board 18 can be a flex circuit board. In some embodiments, circuit board 18 can be formed of one or more deformable materials such as one or more flexible plastic materials.

In certain embodiments, circuit board 18 can be relatively rigid and resistant to deformation. Circuit board 18 can be formed of certain types of rigid plastic materials, for example, which remain relatively rigid to ensure that distances between various sensor radiation sources and detector 12 are not significantly distorted by deformation of circuit board 18.

In some embodiments, circuit board 18 can be formed so that deformation of the circuit board along one direction—the x-direction in FIG. 1A—does not readily occur during use. As a result, the relative distances between detector 12 and the short- and long-distance sources can be maintained, ensuring that accurate and reproducible correction of the measured spectra to reduce the effects of overlying skin and fat layers can be performed. In addition, however, circuit board 18 can deformed at its edges to conform to the shape of a sample (e.g., an arm or leg of a subject), so that sensor 10 can be comfortable and unobtrusively worn by the subject.

In some embodiments, circuit board 18 is formed of two different circuit board components. A first, relatively rigid component corresponds to a mounting member to which the various components of sensor 10, including processors, radiation sources, detectors, power sources, interfaces, and displays are attached. A second, relatively flexible component is attached to the first component and also contacts the sample. By using a two-part construction, sensor 10 ensures that distances between the various radiation sources and detector 12 remain relatively constant during use, but also assumes at least partially a shape complementary to a surface of the sample to which the sensor is attached.

Figure 6A:
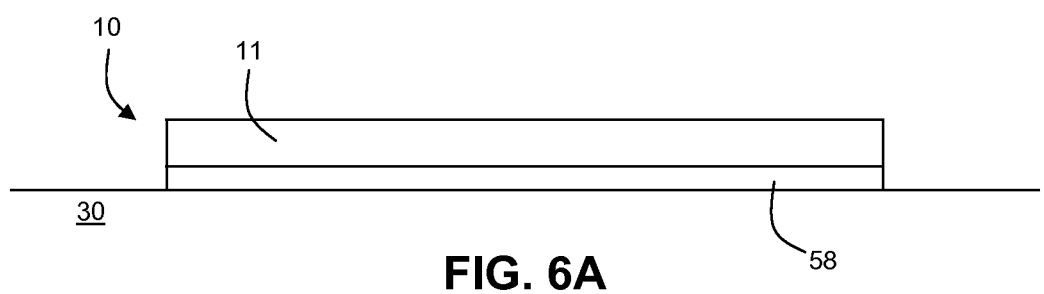
FIG. 6A is a schematic diagram showing attachment of a sensor to a sample with an adhesive pad.

In certain embodiments, sensor 10 can be attached to sample 30 via an adhesive element such as adhesive pad or layer. FIG. 6A shows a schematic diagram of a sensor 10 that is attached to sample 30 with an adhesive layer 58. Adhesive layer 58 is positioned between sensor 10 (e.g., a bottom surface of housing 11) and a surface of sample 30. In some embodiments, layer 58 can be formed by a paste or another similar substance that can be applied to the surface of a sample and/or to the bottom surface of sensor 10 to affix sensor 10 to the sample.

Figure 6B:
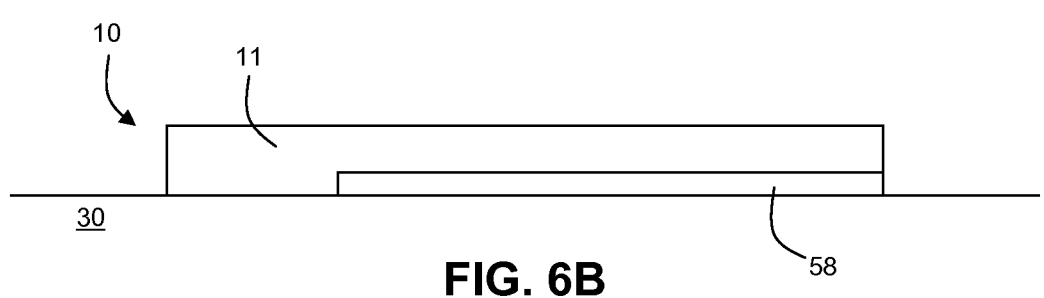
FIG. 6B is a schematic diagram showing attachment of a sensor to a sample with a disposable member on which radiation sources are mounted.

In some embodiments, adhesive layer 58 can be disposable, and can form a portion of a two-layer sensor 10. For example, as shown in FIG. 6B, sensor 10 can include a first non-disposable portion that includes circuit board 18 and components mounted thereon enclosed in housing 11, and a second disposable portion that includes adhesive layer 58 (and, possibly, other layers). Following use, the disposable portion of sensor 10 can be discarded and the non-disposable portion retained for future use. Adhesive layer 58 can be implemented as a flexible material on which some of the radiation sources (e.g., the long-distance sources) are mounted. Short-distance sources can be mounted on circuit board 18 and enclosed within housing 11. When layer 58 is disposed of following use, the short-distance sources are retained within housing 11. A new layer 58 can be attached to housing 11 prior to using sensor 10 to make additional measurements.

Adhesive layer 58, positioned between housing 11 and sample 30, is at least partially transmissive to near-infrared radiation. For example, when the sensor of FIG. 6 is in use, radiation generated by one or more radiation sources of sensor 10 passes through adhesive layer 58 and is incident on sample 30. Scattered radiation from sample 30 also passes through adhesive layer 58 before being incident on detector 12.

In certain embodiments, layer 58 can be implemented as a multilayer structure. For example, layer 58 can include two layers: a first layer that is relatively inflexible and that supports some or all of the components of sensor 10 (e.g., radiation sources, processors, detectors, and other circuitry), and a second layer that contacts the first layer and is also configured to contact the sample. The second layer can be an adhesive layer, and can be flexible so that the second layer deforms to match the surface of the sample when applied to the sample. Many different materials can be used to form the first and second layers. For example, the first layer can include one or more metals, plastics (e.g., high-density plastics), polymer materials, and paper- and/or wood-based materials (e.g., fiberboard). The second layer can include one or more plastic materials, polymer materials, rubber, latex, gels, and other types of flexible materials.

A variety of different disposable and non-disposable configurations are possible. In some embodiments, for example, both the first and second layers are disposable (e.g., all of sensor 10 is disposable). In certain embodiments, neither layer is disposable. Further still, in some embodiments, one of the layers (e.g., the second layer) is disposable, while the other layer (e.g., the first layer) is not. Typically, in a two-layer structure, at least portions of both the first and the second layers are at least partially transmissive to near-infrared radiation, as discussed above, or include a window positioned in the layers to allow near-infrared radiation to pass through the layers.

Figure 7:
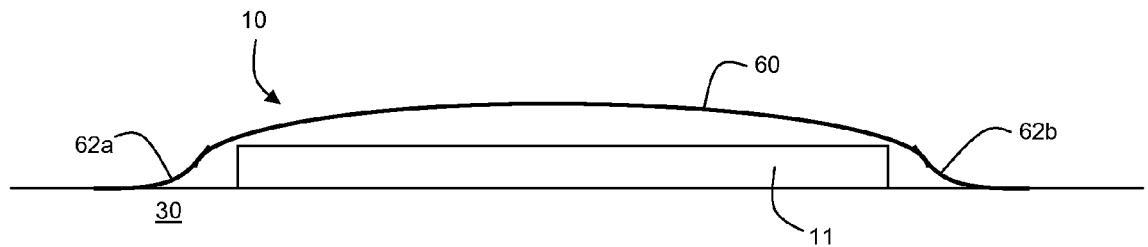
FIG. 7 is a schematic diagram showing a sensor that is secured to a sample with an adhesive patch.

In some embodiments, as shown in FIG. 7, sensor 10 can be attached to sample 30 with an adhesive patch 60. Adhesive patch 60 includes adhesive portions 62a and 62b which adhere to a surface of sample 30, maintaining contact between sensor 10 and the surface of sample 30 as a result. Adhesive patch 60 can be at least partially transmissive to wireless communication signals transmitted by communication interface 28.

In some embodiments, sensor 10 can be completely disposable. Following attachment of sensor 10 to sample 30, measurement of one or more absorbance spectra, and calculation of one or more properties of sample 30, sensor 10 can be detached from the sample and discarded.

In some embodiments, a portion of sensor 10 can be disposable. For example, referring to FIG. 1C, sensor 10 can include a first circuit board 18 that includes detector 12 and the short-distance sources, and a second circuit board 19 that includes the long-distance sources. Second circuit board 19 can be a disposable circuit board. Following use of sensor 10, second circuit board 19 (including the long-distance sources) can be detached from first circuit board 18 and discarded, while first circuit board 18 is retained for subsequent use. In certain embodiments, most or all of the electronic components can be positioned on the disposable portion of sensor 10. For example, sensor 10 can include a disposable circuit board, to which both short- and long-distance sources are attached, along with a processor (e.g., processor 20 and/or 22), electronic memory, a power source (e.g., a disposable battery), and/or other electronic components disclosed previously. Following use of sensor 10, the disposable circuit board and all of the attached electronic components can be discarded, and the remaining portion of sensor 10 can be retained for subsequent use.

Figure 8:
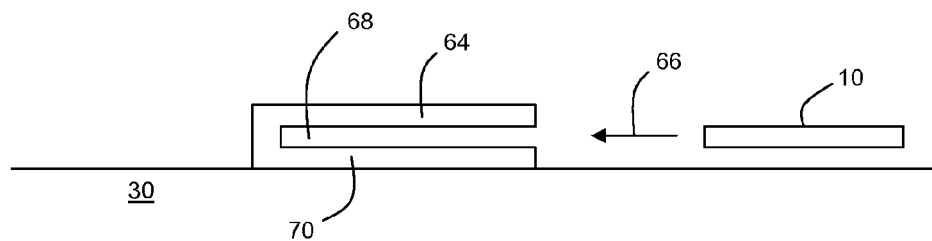
FIG. 8 is a schematic diagram showing a sleeve that is used to attach a sensor to a sample.

In certain embodiments, sensor 10 can be attached to a sample with a complementary sleeve. FIG. 8 shows a schematic view of a sleeve 64 that is attached to a surface of sample 30. For example, sleeve 64 can be attached to an arm or leg of a patient who is exercising or performing aerobic activity, or receiving medical treatment.

Sleeve 64 includes an internal pocket 68 that is dimensioned to accommodate a sensor. Sensor 10 can be attached to sample 30 by inserting sensor 10 into pocket 68 along the direction shown by arrow 66. Typically, sleeve 64 is formed from a flexible material such as a plastic material. At least a portion of sleeve 64 (e.g., lower portion 70) can be at least partially transmissive to radiation generated by one or more radiation sources of sensor 10 and/or to wireless communication signals generated by communication interface 28. During operation, incident radiation from the one or more sources passes through lower portion 70 of sleeve 64 and into sample 30. Scattered radiation from sample 30 passes through portion 70 before being incident on detector 12.

Sensor 10 includes power source 26. In some embodiments, for example, power source 26 can be a connector (e.g., a plug) that receives power from an external source, such as a hospital or treatment center power source and/or a conventional wall socket, which can include a transformer block. In certain embodiments, power source 26 can be a connector such as a conventional power connector or a USB connector that connects to an external processing device such as a computer. Sensor 10 can be configured to receive electrical power from the external processing device through the connector. Power source 26 can also generally include various types of electronic power conditioning devices such as transformers, resistors, capacitors, inductors, transistors, and other circuit elements.

In certain embodiments, power source 26 can be a self-contained power source such as a battery, a photo-voltaic cell, a fuel cell, or another type of stand-alone source. Suitable battery types for power source 26 include, for example, nickel metal hydride batteries, lithium ion batteries, and solid electrolyte (primary) batteries. In some embodiments, power source batteries can be rechargeable, and can be recharged when sensor 10 is not in use. In certain embodiments, power source batteries can be disposable batteries of various types.

In certain embodiments, power source 26 can include a connector that connects to a portable power source such as a battery that is worn by a patient (e.g., worn on an arm or leg of a patient, or attached via one or more straps to a patient). This arrangement may allow for the use of sensor 10 with a larger, higher-capacity battery than would otherwise be available if the battery was attached directly to circuit board 18.

In some embodiments, power source 26 can include a replaceable battery similar to, for example, a mobile phone battery. Sensor 10 can include a connector which mates with a portion of the replaceable battery to enable the battery to supply electrical current to components attached to circuit board 18. The connector can form a portion of a cradle which supports the replaceable battery. One replaceable battery can then be easily exchanged for another, for example, by removing the old battery and sliding the new battery into the cradle.

Figure 9:
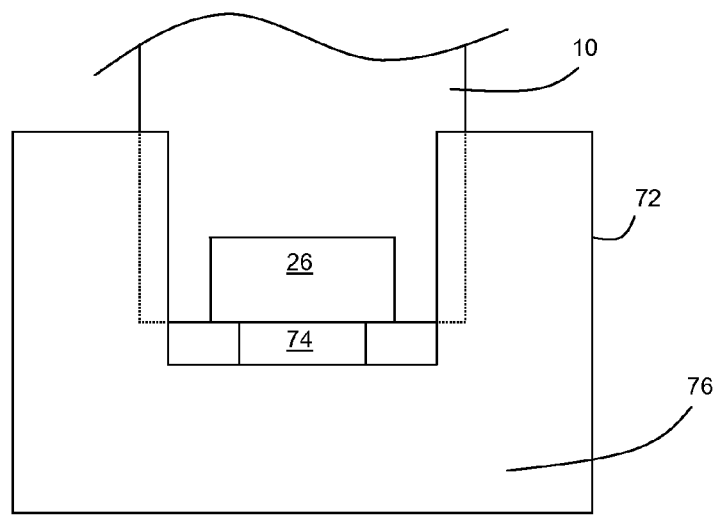
FIG. 9 is a schematic diagram showing an embodiment of a charging cradle for a sensor.

In certain embodiments, when power source 26 includes a rechargeable component such as a battery, a charging cradle can be configured to support sensor 10 while the rechargeable component is charged. FIG. 9 shows a schematic diagram of a charging cradle 72 that includes a support member 76 and a power connector 74. Support member 76 includes vertical grooves into which the edges of sensor 10 are accommodated, maintaining sensor 10 in a relatively fixed position with respect to charging cradle 72. Power connector 74 engages with a mating connector on power source 26 of sensor 10; power source 26 is typically a rechargeable battery, for example. Power is supplied through power connector 74 to power source 26 to recharge power source 26. Cradle 72 can include, for example, power-limiting circuits that sense when power source 26 is nearing a full-charge condition, and which then restrict the flow of power to power source 26 to prevent over-charging.

Sensor 10 includes electronic processor 20, and optionally includes one or more additional applications processors (e.g., applications processor 22). The processors generally coordinate all sensor functions, including directing radiation sources to produce incident radiation, directing detector 12 to receive and analyze scattered radiation, and performing a variety of mathematical operations on data received from detector 12. The processors are also generally responsible for delivering control signals to various sensor components, receiving status signals from sensor components, monitoring the delivery of operating power to sensor components and the supply of power from power source 26, sending data to display 24 to be displayed, and transmitting and receiving communications signals to external devices via communication interface 28. If sensor 10 includes one or more applications processors 22, some of these functions can be provided by the applications processors. In particular, the applications processors can be configured to perform mathematical operations on data received from detector 12 to derive one or more sample properties from the data, as discussed previously. In general, processor functions can be distributed among various processors as desired; the main criteria which generally govern the distribution of processor functions include maintaining relatively efficient sensor operation where possible without significant processor-related lags, and keeping power consumption relatively low (by keeping processor clock rates relatively low and avoiding the use of cooling devices, for example).

In general, the methods disclosed herein are performed by processor 20 and/or one or more applications processors 22. In particular, any of the configuration, control, or analysis steps can be performed automatically by one or more processors of sensor 10. Processor 20 and/or one or more applications processors 22 can be configured to measure absorbance spectra of sample 30, and to derive from the absorbance spectra one or more properties of sample 30, including oxygen tension, oxygen saturation, pH, hematocrit, hemoglobin concentration, anaerobic threshold, and oxygen consumption of the sample.

In certain embodiments, sensor 10 does not include a processor. For example, sensor 10 can include a connector through which control signals, configuration signals, data, and analysis results can be delivered to a processor in another device (e.g., another calculating device such as a computer, a personal digital assistant, a control unit, a mobile telephone, a remote control, or another such device).

In some embodiments, sensor 10 can include a display 24. Display 24 can generally be any type of display, such as a low-power liquid crystal or organic LED display, for example. Display 24 can receive data from processor 20 or any of applications processors 22, and can display the data to a subject wearing the sensor and/or to an operator monitoring the subject. The data received and displayed can include sample information, calibration information, values of various parameters calculated from absorbance spectra of the sample, and other types of data. The display can be integrated into housing 11 and/or can be located remote from housing 11 and configured to communicate with one or more processors of sensor 10 via communication interface 28 (e.g., which can include a signal cable and/or a wireless transmitter-receiver combination).

In certain embodiments, sensor 10 can be configured to display trend information using display 24. Previously-measured values of one or more parameters measured over a period of time (which can be user-selectable) can be displayed, for example, in graphical format, to show the evolution of the one or more parameters over time. Trend information for individual parameters can be displayed on different axes. Alternatively, or in addition, trend information for certain parameters can be displayed on a common axis (e.g., in different colors, and/or using different symbols) to show relationships between the parameters, for example. Sensor 10 can be configured to fit trend lines to measured data points for any of the parameters. Further, sensor 10 can present a warning to a system operator (e.g., an audible warning, a visual warning, or both) when trend lines for one or more parameters satisfy certain criteria (e.g., approach closer than a certain distance, intersect, diverge by more than a certain amount, change slope in certain directions, change curvature by more than a certain amount). Sensor 10 can present a warning to a system operator when values of one or more parameters satisfy certain criteria (e.g., reach pre-determined and/or user-selectable thresholds).

Sensor 10 also includes a communication interface 28. In general, sensor 10 can include a wide variety of different types of communication interfaces, and can include more than one type of communication interface. For example, in certain embodiments, communication interface 28 includes a serial communication interface and/or port such as a USB interface. In some embodiments, communication interface 28 includes a parallel communication interface, or a mixed serial/parallel communication interface.

In some embodiments, communication interface 28 can include a wireless communication interface, including either a wireless transmitter alone, or both a wireless transmitter and receiver. Wireless communication interfaces on sensor 10 can be configured to transmit and/or receive data at radio frequencies, infrared frequencies, microwave frequencies, and other frequencies.

Sensor 10 can be configured to transmit and receive data over both wireless and wired communication interfaces to a variety of external devices. For example, data can be transmitted to external processing devices such as computers, personal digital assistants, cellular telephones and/or smartphones, and other dedicated processing devices. Data can also be transmitted to storage units, including flash drives, and magnetic and/or optical storage devices. Storage devices can also be portable storage devices that can be worn by a subject, for example (e.g., around the waist of a subject), or embedded in a subject's clothing (e.g., a chip-based storage device embedded in a shoe of the subject). Further, data can be transmitted to devices over one or more networks, including private networks, public networks, local and/or wide area networks, mobile telephone and/or data networks, and the internet.

Data can also be transmitted to one or more display devices that can be used by medical personnel, athletic trainers, a subject wearing sensor 10, and other personnel to observe the analyzed data. Typically, data which is transmitted to display devices includes one or more parameters derived from absorbance spectra of a sample. Data which is transmitted to networks and/or storage devices can include one or more calculated parameters and can also include, for example, measured absorbance spectra and sensor calibration and/or configuration information.

Where a charging cradle for sensor 10 is provided, as shown in FIG. 9, the charging cradle can also include a communication interface for receiving data from sensor 10 (e.g., during charging of power source 26). The charging cradle's communication interface can be configured to transmit the received data to storage devices, display devices, and various networks. Use of a relatively low-power communication interface on sensor 10 for transmitting data to charging cradle 72 that includes a higher-power communication interface for transmitting the data to other devices can reduce the overall power consumption of sensor 10.

As discussed previously, sensor 10 typically includes a plurality of long-distance radiation sources, each of which corresponds to interrogation of tissues (e.g., muscle tissue 36) at a different depth below a surface of sample 30. Prior to use, sensor 10 is typically calibrated (e.g., by performing a standardization check routine) relative to a standard, and then attached to a sample (such as a portion of a subject's body) and activated for use. Sensor 10 is typically configured, in an initial measurement step, to select an appropriate long-distance radiation source for sample illumination.

Figure 10:
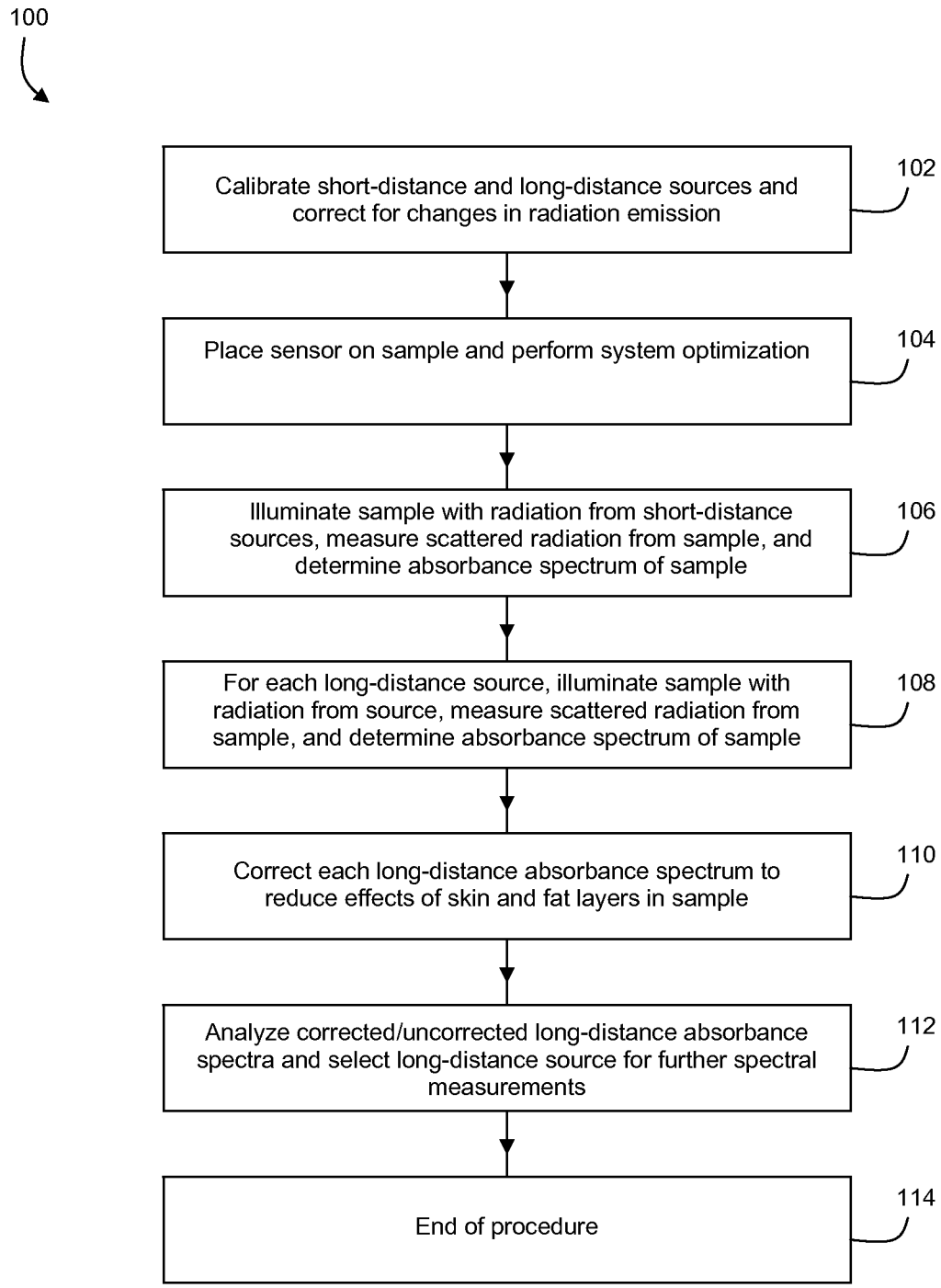
FIG. 10 is a flow chart that shows steps in a calibration check and source selection procedure for a sensor.

FIG. 10 is a flow chart 100 that shows various steps in a standardization or reference check and source selection procedure for sensor 10. In a first step 102, each of the short-distance and long-distance radiation sources on sensor 10 are calibrated to correct for changes in radiation emission properties over time. Calibration typically includes the steps of placing a reference standard against the bottom surface of sensor 10 (e.g., the surface that contacts sample 30 during use). Each short-distance and long-distance radiation source is then activated in turn for a selected duration, and radiation from each source is incident on the reference standard. The intensity of reflected radiation from the reference standard for each radiation source is measured by detector 12 and the measured intensity values are stored. The dark current signal of detector 12 (e.g., with no radiation incident on detector 12) is also measured and stored.

The measured reflected radiation intensity values are then compared to reference intensity values for each radiation source that are stored, for example, in applications processor 22. The reference intensity values can correspond to values that were measured at the time of manufacture of sensor 10. If the integrated radiation intensity and/or the wavelength-dependent intensity of any of the radiation sources have changed, correction factors can be calculated and stored for use during later processing of measured data derived from illumination of a sample with radiation from the sources with changed emission properties.

After standardizing the radiation sources, in step 104 the sensor is attached to a sample (e.g., an arm or leg of a human subject) and a system optimization routine is performed by electronic processor 20. Sensor 10 can generally be attached to a subject's body using any of the attachment devices discussed previously. System optimization ensures that at least a specified number of radiation intensity counts are measured by detector 12, but not higher than a maximum specified intensity. Typically, for example, system optimization is performed so that a substantial portion of the detector's dynamic range is used to measure scattered radiation signals.

System optimization can include adjustment of electronic amplification of measured signals by detector 12 (e.g., detector gain), adjustment of signal acquisition times (e.g., measurement integration times) on detector 12, adjustment of emission intensities of selected short- and/or long-distance radiation sources and/or of radiation emitters therein, and combinations of these various techniques. Scattered radiation spectra from sample 30 can be normalized based on detector electronic gain, signal acquisition times, and illumination times (e.g., duty cycles), as appropriate. If adequate scattered radiation intensity can be measured within a desired spectral band for a subject, electronic signal amplification by detector 12 may be particularly straightforward to implement.

Typically, some or all of the above adjustments can be performed by electronic processor 20 to place the sensor in a suitable operating configuration prior to collecting measurement data from a sample. Adjustments can be performed in alternating fashion, where one parameter is adjusted (e.g., detector gain), followed by adjustment of another parameter (e.g., one or more of the intensities of the radiation sources). Each of the parameters can be adjusted more than once by electronic processor 20 to achieve a suitable operating configuration for the sensor. As an example, to adjust the signal acquisition times for one or more of the radiation sources, electronic processor 20 can selectively illuminate the sample with light from one of the short- or long-distance sources for a predetermined time interval, and then measure scattering light using detector 12. By measuring the intensity of scattered radiation corresponding to the predetermined time interval, an appropriate signal acquisition time for the selected short- or long-distance source can be determined. In general, for any particular source, it is desirable to measure scattered light that nearly, but not completely, fills the dynamic range of detector 12. For example, if detector 12 has a dynamic range of up to 4000 intensity counts, electronic processor 20 can be configured to adjust the signal acquisition times for each of the sources so that measured scattered light corresponding to illumination of the sample with radiation from any one of the sources has a measured intensity or approximately 3500 counts.

Processor 20 determines a suitable signal acquisition time for each source by applying an appropriate scaling factor to the predetermined time interval, where the scaling factor is based on the intensity of scattered radiation during the predetermined time interval. As an example, for a selected radiation source, exposure of a sample for a predetermined time interval of 50 ms and measurement of scattered radiation from the sample during the time interval might yield a total radiation intensity of 700 counts. To reach an intensity of approximately 3500 counts for the selected radiation source, processor 20 calculates that a scaling factor of 3500/700=5 should be applied to the predetermined time interval. Accordingly, processor 20 determines that an appropriate signal acquisition time for the selected radiation source is 5×50 ms=250 ms. Processor 20 can repeat the determination of an appropriate signal acquisition time for some or all of the other short- and/or long-distance sources on the sensor. The predetermined time interval and/or the target scattered radiation intensity (e.g., 3500 counts) can be selected automatically by processor 20, or this information can be entered manually by a system operator.

For some samples, heating can occur, particularly when signal acquisition times become relatively long. In some embodiments, selection of the signal acquisition time for particular sources can be coupled with adjustment of the electronic gain of detector 12 to ensure that suitable scattered radiation intensities are measured without undue sample heating. In some embodiments, the sensor can include a manually- or automatically-determined maximum signal acquisition time (e.g., 1000 ms or 500 ms). If the signal acquisition time for a particular radiation source exceeds the maximum signal acquisition time, the electronic gain of detector 12 can be increased when detecting scattered radiation corresponding to illumination with radiation from the selected source. In particular, the electronic gain of detector 12 can be incrementally increased, and the procedure discussed above can be repeated for the selected radiation source to determine a new (e.g., lower) signal acquisition time at the higher gain setting. For any of the short- and/or long-distance sources, the process of incrementing the gain of detector 12 and re-determining the signal acquisition time can be repeated until a suitable acquisition time (e.g., lower than the maximum signal acquisition time) at a particular gain setting of detector 12 is determined.

In general, the maximum signal acquisition time can vary for different radiation sources, as radiation from particular sources might heat the sample to a greater extent than radiation from other sources. The maximum signal acquisition times, the electronic gain settings, and the determined signal acquisition times for each of the radiation sources can be stored in the sensor's on-board data storage unit, for example, or in an external storage device or medium.

In some embodiments, the sensor can include a temperature monitor that can be used to measure the temperature of a sample to prevent undue sample heating during measurements. As discussed above, processor 20 and/or processor 22 can include an internal temperature sensor that can be used to monitor the sample's temperature. The internal temperature sensor can include, for example, a circuit element with a resistance that changes in a reproducible way as the temperature of the circuit element changes. As the resistance of the circuit element changes, electrical signals that propagate through the circuit element also change. Processor 20 and/or processor 22 can detect such changes in the electrical signals, and can include software instructions that convert the changes in the electrical signals to a temperature measurement of the circuit element (and, e.g., of the sample when the sensor is attached to the sample).

Alternatively, as shown in FIG. 1A, a temperature sensor 15 can be mounted on the bottom surface of sensor 10. Temperature sensor 15 can be electronically coupled to processor 20, and can provide information about the temperature of a sample to processor 20. Processor 20 can use this temperature information to adjust the signal acquisition time, detector gain, and light source selection to ensure that the sample does not suffer undue heating during exposure to incident radiation.

In certain embodiments, the system optimization step can also include adjustment of the intensities of radiation produced by the packages and/or LEDs in each of the sources. For example, the output radiation intensities of individual LEDs and/or packages in a particular source can be adjusted to ensure that the incident radiation that the particular source provides to illuminate the sample has a particular spectral distribution. In some embodiments, the packages and/or LEDs can be adjusted to produce a spectral distribution of incident radiation that has nearly constant intensity across a particular range of spectral wavelengths. In certain embodiments, the packages and/or LEDs can be adjusted to produce a spectral distribution of incident radiation that is more intense in certain spectral regions than in others; for example, the intensity of the incident radiation in spectral regions corresponding to strong sample absorption can be adjusted to be larger than in non-absorbed spectral regions, so that scattered radiation in the strongly-absorbed regions is sufficiently strong to measure with detector 12. In some embodiments, the detection efficiency of detector 12 can vary as a function of wavelength. The intensity of the incident radiation can be adjusted to compensate for such variations in detection efficiency; for example, in spectral regions where the detection efficiency is low, the incident radiation intensity can be increased accordingly to increase measured scattered radiation signals in these regions.

In some embodiments, adjustment of the intensities of radiation produced by the packages and/or LEDs can also include activating or de-activating certain packages that emit incident radiation in certain spectral regions. For example, short-distance sources can be adjusted to provide additional incident radiation in certain wavelength regions (e.g., in wavelength regions that yield scattered radiation that is used to correct for intervening skin and fat layers) by activating packages and/or LEDs that emit in these wavelength regions. Alternatively, or in addition, the short-distance sources can be configured to de-activate packages and/or LEDs that emit radiation in wavelength regions that do not yield scattered radiation that is used to correct for intervening skin and fat layers.

In general, the emitted radiation intensity from packages and/or LEDs can be adjusted by varying control voltages applied to the packages and/or LEDs, and/or by varying the duty cycle of the packages and/or LEDs, as disclosed previously. In some embodiments, the various short- and long-distance sources can be adjusted so that both short- and long-distance sources produce incident radiation that has the same, or nearly the same, relative spectral intensity distribution. In certain embodiments, some or all of the short-distance sources, and/or some or all of the long-distance sources, can be adjusted to produce incident radiation having different relative spectral intensity distributions. Control parameters and desired spectral intensity values for each of the short- and long-distance sources can be stored in the sensor's on-board data storage unit, for example, or in an external storage device or medium.

The various adjustments that are part of the system optimization routine can generally be performed either before or after the selection of a suitable long-distance source. In FIG. 10, the system optimization routine occurs prior to selecting the long-distance source. However, in some embodiments, a suitable long-distance source can be selected first, and then various operating parameters of the system—including signal acquisition time, electronic detector gain, and the relative spectral profile of the emitted radiation—for both the short-distance source and any one or more of the long-distance sources (e.g., the selected long-distance source) can then be determined.

In optional step 106, the sample is then illuminated with emitted radiation from some or all of the short-distance sources, and scattered radiation from the sample is measured by detector 12. The wavelength-dependent scattered radiation intensity data is received by processor 20 (and/or processor 22), and the processor determines an absorbance (or reflectance) spectrum for the sample corresponding to short-distance illumination (absorbance and reflectance, as discussed above, are related by a simple mathematical transformation, and provide essentially the same information about the sample).

In the next step 108, the sample is then illuminated with emitted radiation from a selected one of the long-distance radiation sources, scattered radiation from the sample is measured by detector 12, and processor 20 determines an absorbance spectrum for the sample corresponding to the selected long-distance illumination. The procedure is repeated in turn for each of the long-distance radiation sources, so that a series of absorbance spectra are obtained, each corresponding to a different long-distance illumination of the sample.

In optional step 110, each of the long-distance illumination spectra is corrected to reduce the spectral effects of overlying skin and fat layers. As shown in FIG. 2 for example, sample 30 typically includes tissues of interest such as muscle tissue 36 and overlying layers of skin 32 and subcutaneous fat 34. The layers of skin and fat can produce spectral effects that are not related to the muscle tissue of interest, and which can reduce the accuracy of sample parameters calculated from the spectra. Accordingly, data from the spectra corresponding to short-distance illumination are combined with data from one of the long-distance illumination spectra to provide a corrected long-distance illumination spectrum in which spectral effects due to the overlying layers are reduced. The process is repeated for each of the long-distance illumination spectra to generate a set of corrected long-distance illumination spectra.

Correcting long-distance illumination spectral data typically includes orthogonalizing the long-distance data against spectral components derived from the short-distance illumination spectrum. Systems and methods for implementing such corrections are disclosed, for example, in U.S. Patent Application Publication No. US 2007/0038041, the entire contents of which are incorporated herein by reference.

In step 112, the corrected (or uncorrected, if steps 106 and 110 are omitted) long-distance illumination spectra are analyzed to select a particular long-distance source for subsequent spectral measurements of the sample. As discussed previously, each of the long-distance radiation sources effectively probes to a selected depth beneath the surface of the sample. Accordingly, the selection of a particular long-distance source can essentially correspond to selecting the long-distance source which most effectively illuminates the tissue of interest (e.g., muscle tissue 36).

Several methods can be implemented by processor 20 to select a suitable long-distance source. In some embodiments, for example, corrected and/or uncorrected long-distance illumination spectra are presented to a system operator, who manually selects a particular long-distance source based on the spectra. The operator's selection of the long-distance source can be based on various criteria including the shape of the different illumination spectra, for example.

In some embodiments, the selection of a suitable long-distance source can be highly or even completely automated. Processor 20 can be configured to select a particular long-distance source based on an analysis of the corrected and/or uncorrected illumination spectra corresponding to the various long-distance sources. In certain embodiments, for example, processor 20 can select a particular long-distance source by fitting the corrected and/or uncorrected illumination spectra to a Taylor series-based model for the primary chromophores in the sample, and then determining the error between the model and each of the illumination spectra. Processor 20 then selects the long-distance source that produces the smallest error. The Taylor series model can take a number of functional forms, depending in part upon the nature of the various chromophores in the sample. Suitable models that can be implemented are disclosed, for example, in U.S. Pat. No. 7,532,919, the entire contents of which are incorporated herein by reference. As an example, a Taylor series expansion model for a light attenuation spectrum $A_{model}(\lambda)$ as a function of the wavelength $\lambda$ of radiation scattered or emitted from a sample is:

$$A_{model}(\lambda) = \ln\left(\frac{I_0(\lambda)}{I(\lambda)}\right)$$
$$= (c_0 + c_1\lambda) + \ln(10) \cdot \langle L \rangle \cdot$$
$$[c_{Hb+Mb}\varepsilon_{Hb}(\lambda) + c_{HbO2+MbO2}\varepsilon_{HbO2}(\lambda) + c_{wat}\varepsilon_{wat}(\lambda)]$$

where $I_0(\lambda)$ is an intensity of incident radiation on the sample, $I(\lambda)$ is an intensity of reflected or scattered radiation from the sample, $c_0$ and $c_1$ are constants, $\langle L \rangle$ is a mean path length of the reflected or scattered light through the sample, $\varepsilon_{Hb}(\lambda)$ is a wavelength-dependent extinction coefficient for deoxygenated hemoglobin in the sample, $\varepsilon_{HbO2}(\lambda)$ is a wavelength-dependent extinction coefficient for oxygenated hemoglobin in the sample, $c_{wat}$ is a concentration of water in the sample, and $\varepsilon_{wat}(\lambda)$ is a wavelength-dependent extinction coefficient for water in the sample.

In general, Taylor series model fitting errors increase with increasing source-detector distance. Accordingly, if a long-distance source was selected based entirely on a minimum fitting error criterion, the long-distance source nearest detector 12 might have the highest a priori probability of being selected. To eliminate path-length related effects from the long-distance source selection algorithm, the illumination spectra can be normalized prior to fitting to fitting to the Taylor series-based model. A variety of different normalization methods can be implemented by processor 20. In some embodiments, for example, processor 20 normalizes the illumination spectra by dividing each absorbance value in a particular spectrum by the maximum absorbance value in the spectrum. Other normalization methods can also be implemented by processor 20, including normalization by signal acquisition time and normalization by the mean value in each particular spectrum.

Following normalization, the Taylor series model fitting errors calculated from the normalized illumination spectra are generally free from effects due to varying optical path lengths of the different sources and different magnitudes of the measured signals corresponding to the different long-distance sources. Instead, the Taylor series model fitting errors are accurate metrics for the suitability of the various illumination spectra for determining oxygen saturation in the sample. Selecting the long-distance source that produces the smallest Taylor series model fitting error based on the normalized illumination spectra is therefore analogous to selecting the long-distance source that most accurately produces a spectrum of a target (e.g., muscle tissue) in the sample.

In conjunction with selecting one of the long-distance sources based on the Taylor series model fitting error derived from the spectrum to which the long-distance source corresponds, the quality of the data measured by illuminating the sample with incident radiation from the source is checked against a minimum suitability criterion using a "3σ" method. To implement the 3σ method, processor 20 determines a value of the quantity σ, which corresponds to the standard deviation of Taylor series model fitting errors for all of the long-distance sources. Processor 20 also determines an average value μ of the Taylor series model fitting errors for all of the long-distance sources. The determination of μ and σ can be based on previously-measured spectra and their associated fitting errors, for example.

Processor 20 determines a root mean square (RMS) value of the Taylor series model fitting error for each spectrum (e.g., each spectrum corresponding to a particular long-distance source) by calculating a sum of squared differences between the Taylor series model fitting errors and the average value of the Taylor series model fitting errors over all measurement wavelengths, dividing the sum of squared differences by the number of measurement wavelengths, and taking the square root of the quotient. Processor 20 compares the RMS value of the Taylor series model fitting error for a particular spectrum to the average value μ of the Taylor series model fitting errors. If the RMS value lies within an error interval centered at the average value μ and having a width of 3σ on either side of the average value (e.g., within an interval (μ-3σ, μ+3σ), processor 20 concludes that, for at least a 99% level of confidence, sample spectra measured by illuminating the sample with radiation from the long-distance source corresponding to the particular spectrum being analyzed are of suitable quality to make accurate determinations of one or more quantities for the sample. The long-distance source corresponding to the particular spectrum being analyzed can then be used to collect data from the sample by measuring scattered radiation from the sample in response to illumination with radiation from the long-distance source.

If the RMS value of the Taylor series model fitting error for a particular spectrum does not fall within the above interval, however, processor 20 determines that the corresponding long-distance source cannot be used to collect data of sufficient quality from the sample. In this manner, processor 20 implements the 3σ method to establish a minimum suitability criterion for any particular long-distance source: the RMS value of the Taylor series model fitting error for the spectrum derived from illumination of the sample by the corresponding long-distance source must fall within the interval (μ-3σ, μ+3σ).

The 3σ method can be implemented at various points in the long-distance source selection process. In some embodiments, after the Taylor series model fitting errors are determined for each spectrum corresponding to a particular long-distance source, the spectrum can be checked to make sure it also satisfies the minimum suitability criterion; long-distance sources that do not satisfy the criterion can be removed from further consideration. After all spectra have been checked and only the spectra that satisfy the criterion have been retained, the long-distance source that corresponds to the smallest RMS Taylor series model fitting error can be selected for use.

In certain embodiments, the Taylor series model fitting errors can be determined for the spectra corresponding to each of the long-distance sources first. Processor 20 selects the spectrum with the smallest RMS Taylor series model fitting error, and checks the spectrum using the 3σ method to make sure the spectrum satisfies the minimum suitability criterion. If the criterion is satisfied, the corresponding long-distance source is selected for further use. If the criterion is not satisfied, processor 20 evaluates the spectrum with the next-smallest RMS Taylor series model fitting error, and repeats the minimum criterion check to determine whether the long-distance source corresponding to this spectrum is a suitable illumination source for further sample measurements. The entire process is further repeated until a long-distance source corresponding to the smallest RMS Taylor series model fitting error and that also satisfies the minimum suitability criterion is identified. This long-distance source is then used to provide incident radiation to the sample for measurement of sample information.

Other criteria can also be used, in addition or as alternatives, to select a suitable long-distance source. For example, in some embodiments, signal acquisition times for each of the long-distance sources can influence the selection of one of the long-distance sources. Generally, signal acquisition times have been observed to increase with increasing source-detector spacing. Accordingly, where several long-distance sources produce illumination spectra with comparable Taylor series model fitting errors, and where the sources each produce sufficiently high quality data to accurately obtain target (e.g., muscle tissue) spectra according to the 3σ method, processor 20 can be configured to select, for example, the long-distance source that is closest to the detector to reduce signal acquisition time.

In certain embodiments, other methods are used to select a suitable long-distance source. For example, the long-distance spectra can be analyzed to determine which spectrum corresponds most closely to an expected spectrum of the tissue of interest. The comparison can be based on the entire measured and expected spectra, or based on selected spectral features (such as absorption peaks at particular wavelengths, for example) within the spectra. Long-distance sources which correspond to probing depths that are too short will generally produce poorly resolved spectral features.

In general, any of the methods for selecting a suitable long-distance source can be used with or without correction of the measured long-distance spectra to account for spectral effects due to intervening layers of skin and fat. That is, in some embodiments, prior to comparing the long-distance spectra, the long-distance spectra can be corrected using information derived from one or more sample absorbance spectra measured based on sample illumination by short-distance sources. Such corrections can be used to reduce or eliminate the effects of skin and fat layers positioned between the sensor and a target of interest (e.g., muscle tissue) in the sample. However, in certain embodiments, the long-distance spectra can be compared without performing a correction for intervening skin and fat layers. The decision as to whether to perform the correction can be made by a system operator (e.g., as a user-selectable option, and/or in response to a prompt from the sensor), or the decision can be made automatically by the sensor based on properties of the long-distance spectra, for example.

Mathematical algorithms can be applied to calculate and/or estimate correlations between the measured and expected spectra, or between certain features of the measured and expected spectra. In some embodiments, the long-distance source that corresponds to the shortest probe depth that produces measured spectra having an acceptable correlation with expected spectra is selected for subsequent interrogation of the sample. If no long-distance source is found to be suitable, sensor 10 provides an alert to a system operator in the form of a visual and/or auditory signal, and a prompt to check and adjust the position of the sensor. Either result leads to the termination of the procedure at step 114.

In some embodiments, sensor 10 can be used for spatially-resolved spectroscopy (SRS), in which spectra based on at least three different long-distance radiation sources are analyzed to determine various sample properties. When sensor 10 operates in SRS mode, at least three different long-distance sources are selected for subsequent illumination based on correspondences between expected and measured spectra and/or spectral features of the sample for the long-distance sources. If at least three suitable long-distance sources cannot be found, sensor 10 provides a visual and/or auditory alert, and a prompt to check placement of the sensor.

In certain embodiments, where the sensor includes multiple short-distance sources, the sensor can be configured to select an appropriate short-distance source for sample illumination (e.g., to correct long-distance spectra for intervening layers of skin and fat). A variety of methods can be used to select a suitable short-distance source. In some embodiments, the selection of a short-distance source can be performed in conjunction with selection of a long-distance source. As discussed above, a plurality of long-distance spectra corresponding to different long-distance sources are acquired. Short-distance spectra corresponding to each of the short-distance sources are also acquired. Each long-distance spectrum is then corrected (e.g., orthogonalized) using each one of the short-distance spectra in turn. For each pair of long-distance and short-distance spectra, the corrected long-distance spectrum is fitted to a Taylor series-based model, and the model fitting error is determined. After corrected long-distance spectra from each of the pairs of long-distance and short-distance spectra have been fitted and the model fitting error determined, the corrected long-distance spectra are checked using the 3σ method discussed above, and combinations of short- and long-distance sources that do not yield spectra that satisfy the minimum suitability criterion corresponding to the 3σ method are eliminated from further consideration. Sensor 10 then selects the combination of short- and long-distance sources that yield spectra with the smallest fitting error, provided the spectra measured using this combination also satisfy the minimum criterion of the 3σ method.

In some embodiments, selection of a suitable short-distance source can be performed manually by a system operator. Sensor 10 can display a prompt requesting that the system operator select a suitable short-distance source, for example. Short-distance source selection can also be achieved through one or more configuration settings that the operator enters into sensor 10 (e.g., with or without prompting). Sensor 10 can display to the operator one or more sample absorbance spectra measured with the short-distance sensors to assist the system operator in selecting a suitable short-distance source.

The standardization routine discussed above in connection with FIG. 10 (e.g., step 102) is optional, and is not required prior to using sensor 10 to perform the measurements disclosed herein. In some embodiments, for example, sensor 10 is not standardized prior to use. Instead, sensor 10 can be used in an un-standardized configuration, or standardization information can be retrieved (e.g., from an external storage unit or an on-board storage unit such as a system memory) and used to configure sensor 10 prior to use. Sensor 10 can then, optionally, be configured to select a suitable long-distance source, as discussed above in connection with FIG. 10.

Figure 11:
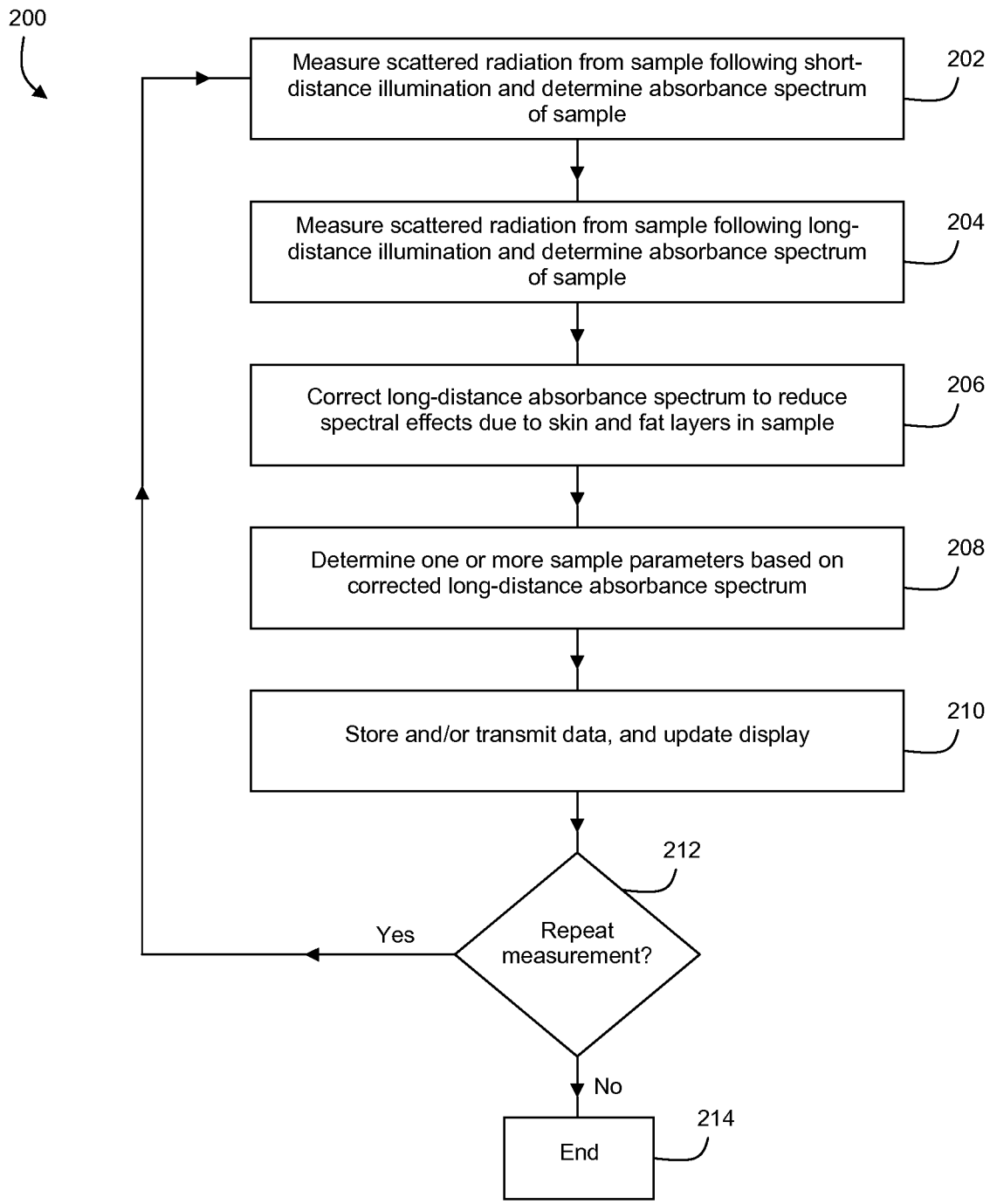
FIG. 11 is a flow chart that shows steps in a measurement procedure that uses a sensor.
Figures 12A, 12B, 12C, 12D:
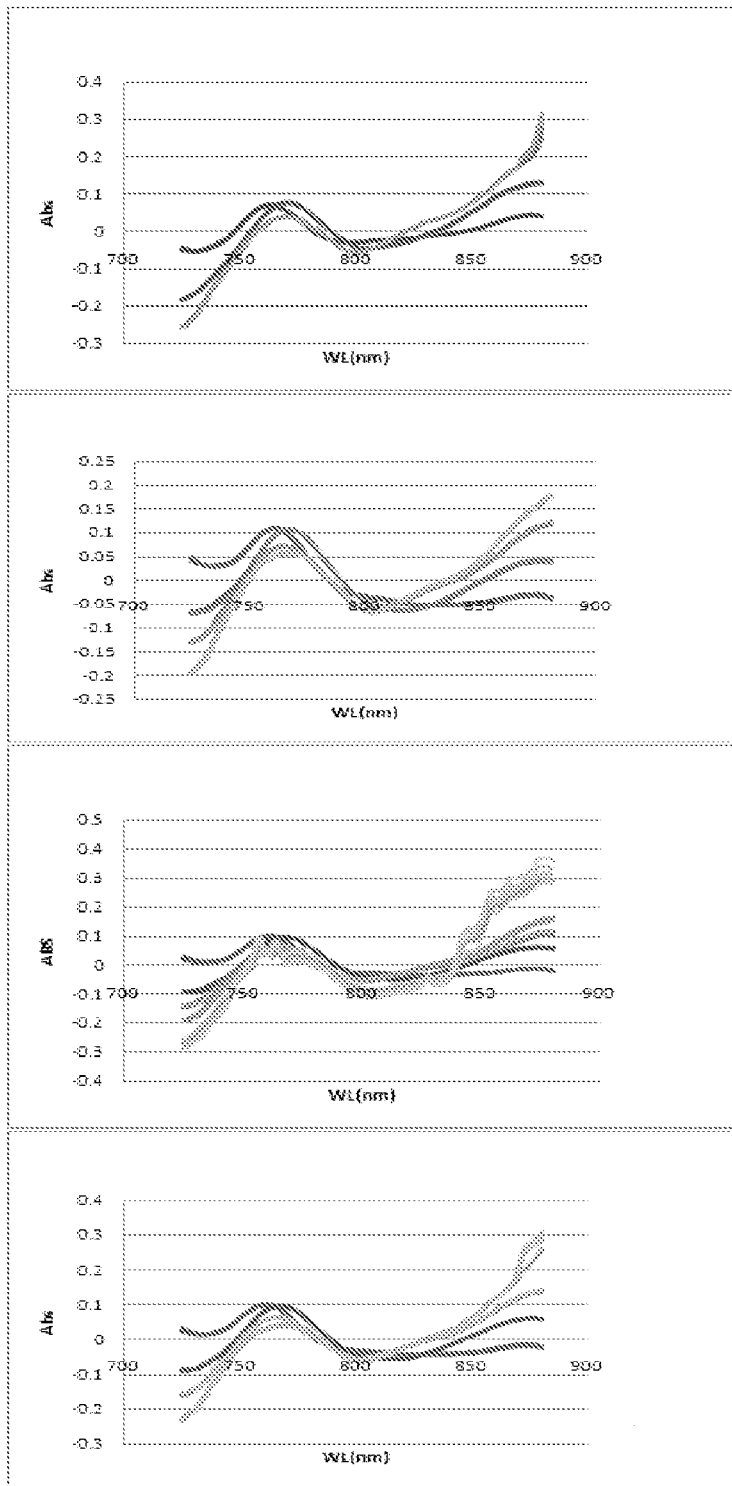
FIGS. 12A-D are plots of reflectance spectra for a human test subject measured at different positions on the subject's body.

Following selection of a suitable long-distance radiation source (or sources), measurement of spectral data from the sample and calculation of one or more parameters from the spectral data can begin. FIG. 11 shows a flow chart 200 that includes a series of measurement steps. In first step 202, the short-distance radiation sources are activated and a short-distance absorbance spectrum of the sample is determined, as discussed in connection with step 106 of FIG. 10. Then, in step 204, the selected long-distance radiation source is activated and a long-distance absorbance spectrum of the sample is determined in a manner similar to step 108 of FIG. 10. In step 206, the long-distance spectrum is corrected to reduce spectral effects due to skin and fat layers by orthogonalizing the long-distance spectral data against spectral components derived from the short-distance spectrum, in accordance with step 110 of FIG. 10.

In step 208, one or more sample parameters are calculated by processor 20 based on the corrected long-distance spectral data. As discussed previously, calculated parameters can include one or more of oxygen saturation, oxygen tension, pH, hematocrit, hemoglobin concentration, anaerobic threshold, water content, and oxygen consumption of the sample. The measured data and/or calculated parameters can be stored in one or more storage units and/or transmitted to one or more external devices or networks in step 210. If display 24 is present (or if another display is linked to sensor 10), the display can be updated with newly measured and/or calculated values. As discussed previously, trend information—including previously-measured values of the one or more parameters—can be displayed on display 24 for a user-selectable time window. Trend information can be updated on display 24 as additional values of the one or more parameters are measured by the sensor.

In decision step 212, processor 20 and/or 22 decides whether to continue monitoring the sample or to terminate data acquisition (e.g., in response to an interrupt signal initiated by a user). If measurement of sample data is to continue, flow control returns to step 202 and the measurement procedure repeats. If measurement is to terminate, the procedure ends at step 214.

Processor 20 can perform a series of additional automated functions during data acquisition. In some embodiments, for example, processor 20 is configured to determine whether measured spectral data for the sample either exceeds a maximum intensity threshold, or falls below a minimum intensity threshold. The thresholds can be entered manually by a system operator, determined automatically by processor 20, or retrieved by processor 20 from a sensor memory or storage unit, or from an external storage device or medium. To test whether the spectral data exceeds the maximum intensity threshold, the spectral data is analyzed before it is converted to an absorbance spectrum. Processor 20 compares the highest intensity value in the measured spectral data to the maximum intensity threshold. If the highest intensity value does not exceed the maximum intensity threshold, the spectral data is converted to an absorbance spectrum, which is then further analyzed by processor 20. However, if the highest intensity value exceeds the maximum intensity threshold, the spectral data is not converted into an absorbance spectrum and additional spectral data (e.g., another illumination spectrum) is acquired by directing incident radiation from the selected long-distance source to the sample and measuring scattered light from the sample.

Processor 20 then compares the highest intensity value in the additional spectral data to the maximum intensity threshold. If the highest intensity value in the additional spectral data does not exceed the maximum intensity threshold, the additional spectral data is converted to an absorbance spectrum, which is then further analyzed by processor 20. However, if the highest intensity value in the additional spectral data exceeds the maximum intensity threshold, the spectral data is not converted into an absorbance spectrum. Processor 20 then re-determines the signal acquisition time for the long-distance source, and can, in certain embodiments, re-determine the signal acquisition time for some or all of the short-distance sources. Typically, the signal acquisition time for the long-distance source will be reduced to further limit the accumulated intensity of the scattered radiation measured by detector 12.

To determine whether the scattered radiation signals measured by detector 12 are too small, processor 20 compares each of the measured spectral intensity values to the minimum intensity threshold. If none of the measured spectral intensity values is less than the minimum intensity threshold, processor 20 converts the spectral data to an absorbance spectrum for the sample, and further analyzes the absorbance spectrum. However, if one or more of the measured spectral intensity values is less than the minimum intensity threshold, the spectral data is not converted to an absorbance spectrum. Instead, processor 20 acquires additional spectral data (e.g., another illumination spectrum) by directing incident radiation from the selected long-distance source to the sample, and measuring scattered light from the sample via detector 12.

Processor 20 then compares the additional spectral data to the minimum intensity threshold. If none of the measured spectral intensity values in the additional spectral data is less than the minimum intensity threshold, processor 20 converts the additional spectral data to an absorbance spectrum for the sample, and further analyzes the absorbance spectrum. However, if one or more of the measured spectral intensity values in the additional spectral data is less than the minimum intensity threshold, the spectral data is not converted to an absorbance spectrum. Instead, processor 20 then re-determines the signal acquisition time for the long-distance source, and can, in certain embodiments, re-determine the signal acquisition time for some or all of the short-distance sources. Typically, the signal acquisition time for the long-distance source will be increased to increase the accumulated intensity of the scattered radiation measured by detector 12.

In some embodiments, adjustment of the detector's electronic gain can be used in place of, or in combination with, re-determination of the signal acquisition time for the short-distance sources and/or the selected long-distance source. For example, to reduce the intensity of radiation measured by detector 12, processor 20 can be configured to reduce the signal acquisition time of the selected long-distance radiation source, to reduce the electronic gain of detector 12 when scattered radiation from the sample is measured following illumination of the sample with incident radiation from the selected long-distance source, or both. Conversely, to increase the intensity of radiation measured by detector 12, processor 20 can be configured to increase the signal acquisition time of the selected long-distance radiation source, to increase the electronic gain of detector 12 when scattered radiation from the sample is measured following illumination of the sample with incident radiation from the selected long-distance source, or both.

In certain embodiments, selection of a different long-distance source can be used in place of, or in combination with, re-determination of the signal acquisition time for the short-distance sources and/or the selected long-distance source, and/or adjustment of the detector's electronic gain. For example, in addition to increasing the signal acquisition time and/or increasing electronic gain to increase the intensity of measured spectral data, processor 20 can be configured to select a new long-distance source to illuminate the sample. The selected long-distance source can be closer to detector 12 than the initial long-distance source. Alternatively, in addition to decreasing the signal acquisition time and/or decreasing electronic gain to reduce the intensity of measured spectral data, processor 20 can be configured to select a new long-distance source to illuminate the sample. The selected long-distance source can be further from detector 12 than the initial long-distance source.

Electronic gain adjustments and selection of different long-distance sources are particularly useful when the signal acquisition time for a selected long-distance source is already relatively long. Long signal acquisition times can lead to heating of the sample, yielding erroneous spectral data that leads to incorrect determination of values of various sample properties based on the spectral data. To avoid such errors, the signal acquisition time can be increased by relatively small amounts (or not at all), while other system parameters such as electronic gain and the selected long-distance source can be adjusted instead. Typically, gain adjustments are made first by processor 20, and if such adjustments are insufficient to yield spectral data within a desired measurement intensity range and/or without significantly heating the sample, processor 20 can select a different long-distance radiation source to illuminate the sample.

Adjustments of one or more of signal acquisition time, electronic gain, and the selected long-distance source can also be used to compensate for changes in the sample during measurement of spectral data. For example, where the sample is tissue in a human subject, significant changes in blood flow and other physiological parameters can occur when the subject is exercising. Such changes can affect spectral measurements by either increasing or reducing the amount of scattered light measured by detector 12. The sensors disclosed herein can compensate for such changes by adjusting parameters such as signal acquisition time, electronic gain, and selected long-distance source to compensate for the effects of the changes.

Any of the adjustments and analysis steps can be performed with the intervention of a system operator, or completely automatically by processor 20 with no operator intervention. In some embodiments, for example, processor 20 is configured to examine spectral data as it is acquired in real time or near-real time, and to adjust the various operating parameters of the sensor appropriately to yield measurement signals that fall within a desired range of signal intensities.

Figure 31:
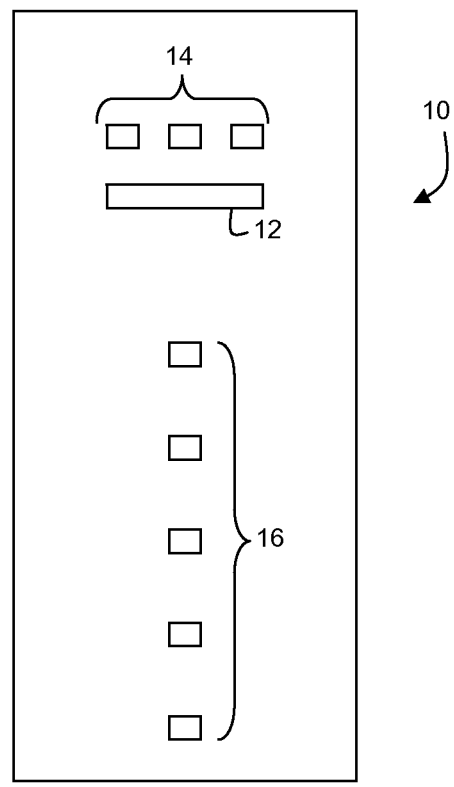
FIG. 31 is a schematic diagram of an embodiment of a sensor that includes short-distance and long-distance radiation sources on opposite sides of a detector.
Figure 32:
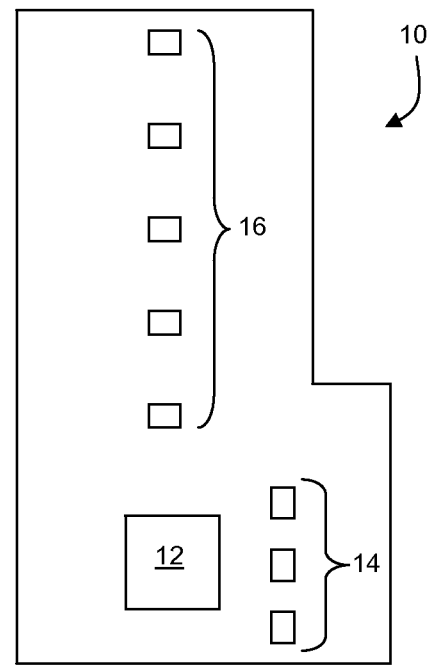
FIG. 32 is a schematic diagram of an embodiment of a sensor that includes short-distance and long-distance radiation sources spaced from a detector along different directions.
Figure 33:
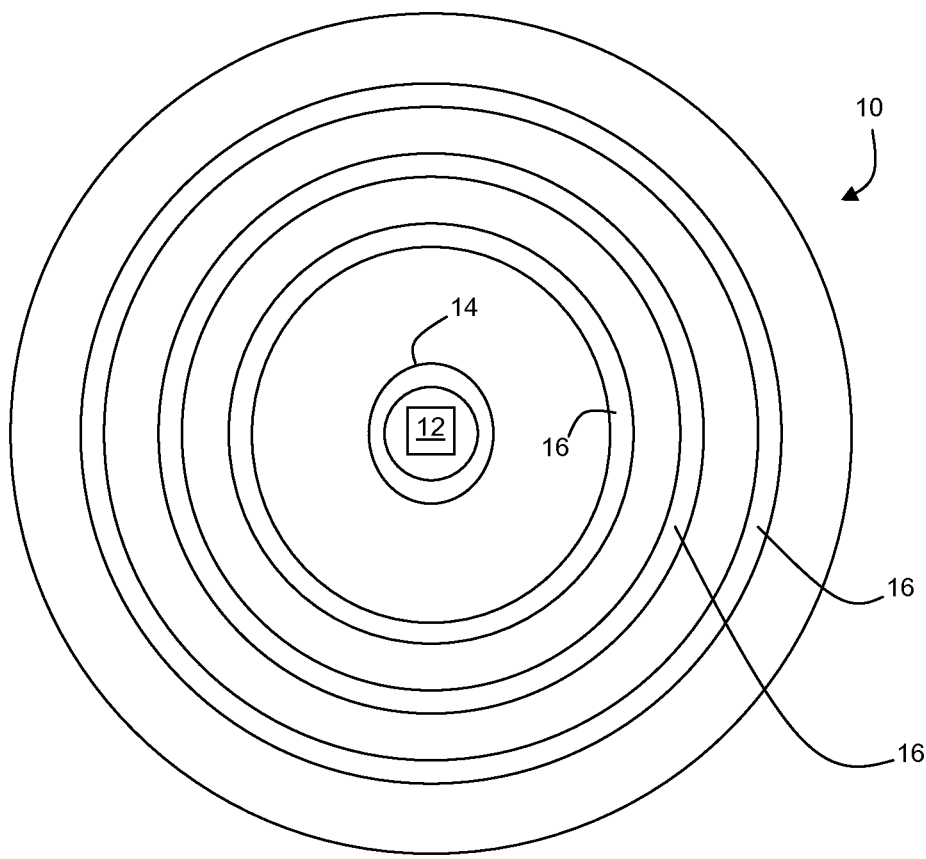
FIG. 33 is a schematic diagram of an embodiment of a sensor that includes annular radiation sources.

In some embodiments, sensor 10 can include radiation sources (e.g., short-distance and/or long-distance radiation sources) in arrangements that differ from the arrangement shown in FIG. 1A. For example, FIG. 31 shows a bottom view of a sensor 10 that includes a plurality of long-distance radiation sources 16 arranged on an opposite side of detector 12 from a plurality of short-distance radiation sources 14. FIG. 32 shows a bottom view of a sensor 10 that includes a plurality of short-distance radiation sources 14 spaced from detector 12 along an x-direction of the sensor, and a plurality of long-distance radiation sources 16 spaced from detector 12 along a y-direction of the sensor. FIG. 33 shows a bottom view of a sensor 10 having an approximately circular shape, and including an annular short-distance radiation source 14 and a plurality of annular long-distance radiation sources 16.

In general, embodiments of sensor 10 can include any number of short-distance sources and any number of long-distance sources. The various sources can have different shapes, including circular or arc-shapes, square, rectangular, and/or other regular or irregular shapes. The radiation sources can generally be distributed in any manner relative to one another, provided the distribution of radiation sources is consistent with the functionality of sensor 10 disclosed herein.

Figure 34:
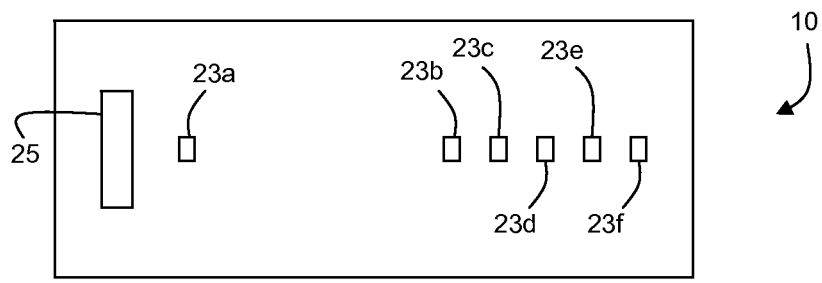
FIG. 34 is a schematic diagram of an embodiment of a sensor that includes one radiation source and multiple detectors.

In certain embodiments, sensor 10 can include multiple detectors. For example, embodiments of sensor 10 can include a single radiation source and multiple detectors, or multiple radiation sources and multiple detectors. FIG. 34 shows a bottom view of a sensor 10 that includes a single radiation source 25 and a plurality of detectors 23a-f. Radiation source 25 can generally have any of the properties disclosed herein in connection with sources 14a-c and 16a-e, for example. Each of detectors 23a-f can typically have any of the properties disclosed herein in connection with detector 12, for example.

Detector 23a corresponds to a short source-detector spacing, while each of detectors 23b-f corresponds to a long source-detector spacing. Scattered radiation detected by detectors 23b-f corresponds to different probe depths beneath a sample surface, as discussed previously. Accordingly, operation of sensor 10 in FIG. 34 is generally similar to operation of sensor 10 in FIG. 1A, for example. One of the long-distance detectors 23b-f is selected to detect scattered radiation from a tissue of interest within the sample according to an procedure similar to the procedure of FIG. 10. Spectra corresponding to long-distance illumination of the sample—measured by detectors 23b-f—are corrected to reduce spectral effects of skin and fat layers by orthogonalization against spectral components derived from short-distance spectral data measured by detector 23a. The other properties and features of sensor 10 in FIG. 34 are generally similar to properties and features of the other sensors disclosed herein.

The number and positions of detectors in FIG. 34 can generally be selected as desired. Any number of detectors can be positioned on the bottom surface of sensor 10, in analogous fashion to the placement of radiation sources in the embodiments shown in FIGS. 31-33. Detectors 23a-f can generally have a wide variety of shapes, including circular, annular, rectangular, square, and other regular and/or irregular shapes. The numbers, positions, and shapes of detectors 23a-f are chosen to be consistent with the functionality of sensor 10 disclosed herein.

Figure 35:
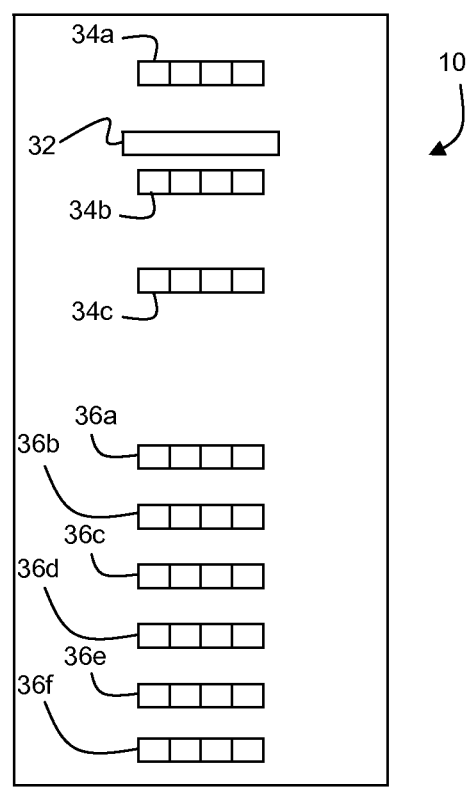
FIG. 35 is a schematic diagram of an embodiment of a sensor that includes multiple short-distance sources.

In some embodiments, sensor 10 can include multiple short-distance sources. Some of the short-distance sources can be spaced differently from the detector relative to other short-distance sources. FIG. 35 shows an exemplary embodiment of a sensor 10 that includes a plurality of short-distance sources 34a-c, and a plurality of long-distance sources 36a-f. Short-distance sources 34a-c are each spaced differently relative to detector 32. For example, in some embodiments, the spacings s of sources 34a-c with respect to detector 32 are 6 mm, 3 mm, and 9 mm, respectively. In general, sensor 10 can include any number of short-distance sensors, spaced from detector 32 in any manner to provide suitable short-distance incident radiation for measuring sample spectra and/or correcting measured long-distance spectra.

Applications

The sensors disclosed herein can be used in a variety of different applications for monitoring both human and animal subjects. Due to their relatively low profile, small size and weight, and self-contained nature, the sensors can be comfortably worn without imposing burdensome movement restrictions on subjects.

In some embodiments, the sensors disclosed herein can be used to monitor a subject performing exercise, such as an athlete undergoing a training regimen. By measuring relevant muscle tissue properties such as anaerobic threshold, oxygen consumption, and muscle temperature, the progress of the regimen can be followed and evaluated. During training, the sensor can be worn by the athlete and near real-time measurement results can be transmitted wirelessly to a monitoring station, where a coach, trainer, doctor, or other person can monitor the athlete's progress and condition.

In similar fashion, the sensors can be used to monitor subjects undergoing physical rehabilitation following an injury, or stress testing in an evaluation center. The sensors can provide data relating to the effectiveness of a rehabilitation program, and can also provide for monitoring of the subject's condition during periods of physical exertion. The sensors can transmit data wirelessly or via one or more wires that are connected to display and/or data storage units, for example. Display units can be built into various pieces of exercise equipment such as treadmills and exercise bicycles, and the sensors can transmit data to some or all of these devices as monitoring of the subject occurs.

In certain embodiments, the sensors can be used to monitor the condition of individuals engaged in dangerous and/or stressful activities. For example, the sensors can be used to monitor soldiers and/or astronauts. Hemorrhage is a major cause of soldier death. To help soldiers survive major injury, seriously injured soldiers should be quickly identified and appropriate resuscitation techniques applied. Significant blood loss leads to shock, which in turn produces inadequate organ perfusion and tissue oxygenation. Resuscitation from shock corrects the mismatch between available oxygen and oxygen demands of critical organs. Accordingly, rapid response to hemorrhage—including resuscitation from shock—within the first hour can prevent cardiovascular collapse and death. Traditional methods for assessing shock—including the measurement of parameters such as blood pressure, heart rate, urine output, and systemic measures of oxygen transport such as oxygen delivery and consumption, blood lactate, arterial pH, and base excess—may provide uncertain markers as to the onset and/or endpoint of shock and response to resuscitation.

Measurements of the partial pressure of oxygen and/or oxygen saturation in peripheral muscle tissue are related to changes in central blood volume, as markers of the hemodynamic compensatory responses that shunt blood away from the skeletal muscles and internal organs (e.g., liver, stomach, intestines, kidney) to the heart and brain, preserving blood pressure. As such, these quantities can provide an indication of internal bleeding prior to the onset of shock (drop in blood pressure) and provide a more accurate and early indication of adequate resuscitation during hemorrhage. The sensors disclosed herein can be used to provide real-time or near real-time measures of the partial pressure of oxygen and/or oxygen saturation in muscle tissue, and can therefore be used for early identification of soldiers most at risk of developing hemorrhagic shock. If a reduction in muscle oxygenation is not rapidly reversed, the patient's muscle pH decreases. Resuscitation to restore normal muscle oxygen without restoring normal levels of muscle pH can lead to poor patient outcomes. As such, the sensors disclosed herein permit continuous monitoring of muscle oxygen saturation/partial pressure, and/or pH, and data transmitted from sensors to control centers can be used, e.g., to alert support personnel to the need for medical attention when injuries are sustained. The sensors disclosed herein can, in some embodiments, be incorporated into clothing worn by soldiers and/or astronauts, making monitoring of these individuals even more unobtrusive. When resuscitation occurs, the sensors can be used to monitor muscle oxygen saturation/partial pressure and/or pH to direct the resuscitation therapy, in some cases by providing input into electronic controllers on therapeutic devices, thereby improving patient outcomes. Therapeutic devices that can receive input information and/or control signals from the sensors disclosed herein include, for example, infusion pumps (e.g., to deliver one or more drugs and/or fluids such as blood or saline solution), ventilators, and other devices configured to deliver fluids to a patient and/or monitor a patient's condition.

In some embodiments, the sensors disclosed herein can be used to monitor critically and/or chronically ill patients in treatment facilities such as hospitals (e.g., in operating rooms, emergency rooms, and intensive care units), during patient transport (e.g., in air and ground ambulances), and in the field. The sensors can also be used for patient monitoring in doctors' offices, clinics, and in patients' homes. Data can be transmitted from the sensors to monitoring stations so that doctors, nurses, and other patient care personnel can monitor the condition of patients and take appropriate actions in the event of emergency conditions or other critical events. Data can be transmitted directly from an ambulance to a receiving hospital in advance of a patient's arrival, so that hospital staff can be prepared to treat the patient immediately upon arrival.

In some applications, patients with chronic diseases such as congestive heart failure can use the sensors disclosed herein at home, continuously or intermittently, to alert a physician when their physical condition worsens to the point where medical intervention is suggested and/or necessary.

The sensors disclosed herein are particularly well suited to applications involving monitoring and treatment of patients with traumatic injuries, sepsis, and patients undergoing surgery. One factor common to each of these conditions is that deaths and complications are frequently a result of poor blood flow to key organs such as the intestines, liver, stomach and kidney, a situation which is typically referred to as poor tissue perfusion. If poor tissue perfusion is recognized early, it can be treated by delivering appropriate volumes of fluid and, if necessary, medications to improve blood flow. If poor tissue perfusion continues untreated, however, it can result in tissue acidosis (low tissue pH), which leads to cell injury and tissue death. This is one of the causes of sepsis and multiple organ dysfunction, and can result in long hospital stays, expensive medical treatment, and high mortality rates.

The sensors disclosed herein can determine, based on measurements of scattered radiation from a subject's tissue, muscle oxygen levels, which provide a surrogate measurement of internal organ oxygenation. This can lead to early identification of poor tissue perfusion. The sensors can also determine muscle pH and muscle oxygen saturation, which must typically be maintained above threshold levels during patient care. The output from these sensors can be connected to other equipment which delivers fluids, drugs or other therapies aimed at improving tissue perfusion and restoring appropriate levels of tissue oxygen and pH. The output from these sensors can be used to control such treatment equipment so that muscle oxygen, pH and hematocrit remain at pre-defined levels. Other properties determined by the sensors disclosed herein can also be evaluated and used to assess managed care programs for both acutely and chronically afflicted patients.

Hardware and Software Implementation

The method steps and procedures described herein can be implemented in hardware or in software, or in a combination of both. In particular, processor 20 (and/or other processors of sensor 10 such as processor 22) can include software and/or hardware instructions to perform any of the methods discussed above. The methods can be implemented in computer programs using standard programming techniques following the method steps and figures disclosed herein. Program code is applied to input data to perform the functions described herein. The output information is applied to one or more output devices such as a printer, or a display device, or a web page on a computer monitor with access to a website, e.g., for remote monitoring.

Each program is preferably implemented in a high level procedural or object oriented programming language to communicate with a processor. However, the programs can be implemented in assembly or machine language, if desired. In any case, the language can be a compiled or interpreted language. Each computer program can be stored on a storage medium or device (e.g., an electronic memory) readable by the processor, for configuring and operating the processor to perform the procedures described herein.

EXAMPLES

The invention is further described in the following examples, which are not intended to limit the scope of the invention described in the claims.

Example 1

To assess the magnitude and distribution of Taylor series model fitting errors, near infrared spectral reflectance measurements were obtained from six adult subjects on different parts of the body, while the adults were in the supine position. Multiple measurement locations on each subject were selected so that the intervening fat layer between the subject's skin and the muscle tissue of interest and the locations spanned a range of thicknesses from 5 mm to 20 mm. Fat thickness measurements were determined quantitatively using an ultrasound scanner (SonoSite, Bothell, Wash.). At each location on each subject, five or six duplicate measurements were performed. The duplicate spectra were normalized and then fitted to a Taylor series model, and Taylor series model fitting errors were determined as the root mean-square error (e.g., the square root of the quotient of sum of squared errors divided by the number of individual wavelength points in each spectrum) between the measured spectra and the Taylor series model. After all measurements and errors were determined, an average fitting error and a standard deviation of the fitting errors were determined for each location from the duplicate measurements.

Exemplary spectra for one of the subjects are shown in FIGS. 12A-D. The spectra correspond to measurements performed on the subject's calf (FIG. 12A, fat thickness 9.4 mm), shoulder (FIG. 12B, fat thickness 9.4 mm), high thigh (FIG. 12C, fat thickness 13.1 mm), and normal thigh (FIG. 12D, fat thickness 9.6 mm) at different source-detector separations (L1=30 mm, L2=35 mm, L3=40 mm, L4=45 mm, L5=50 mm). Despite the differences in fat thickness and measurement location, all of the spectra have similar shapes, with maximum absorption near 760 nm; there are minimal differences as a function of the various source-detector spacings. The spectra corresponding to the largest fat thickness (FIG. 12C) appear to show more variance than the spectra corresponding to smaller fat thicknesses.

Figure 13A:
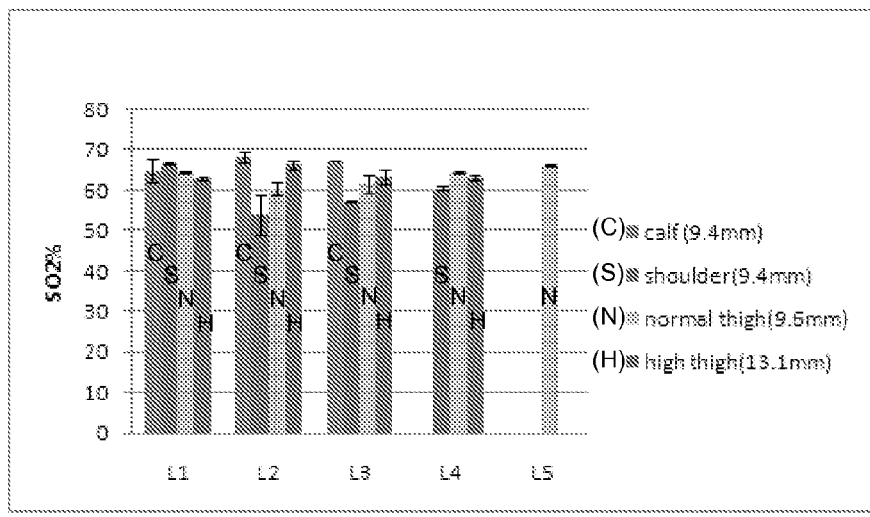
FIG. 13A is a bar chart comparing calculated values of oxygen saturation for a test subject based on spectral reflectance measurements performed at different locations on the subject's body, and at different source-detector spacings.
Figure 13B:
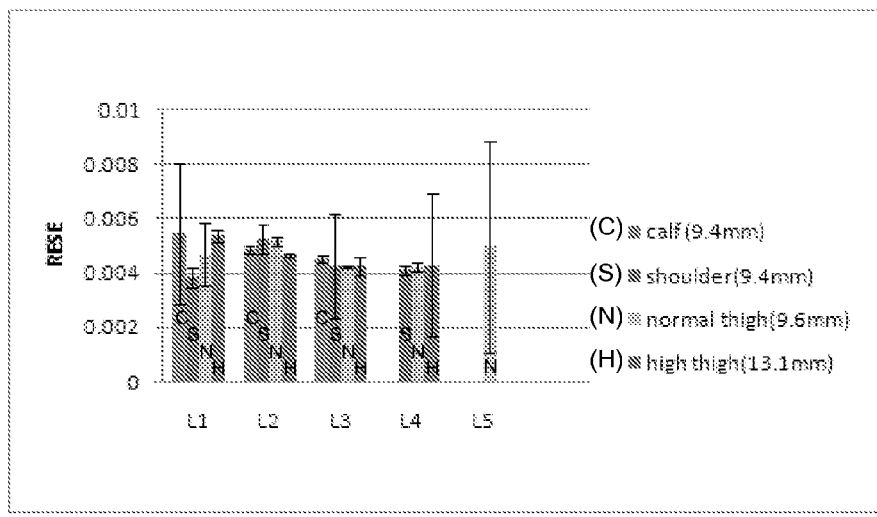
FIG. 13B is a bar chart showing Taylor series model fitting errors associated with the values of oxygen saturation shown in FIG. 13A.

Measurements of oxygen saturation derived from the spectra shown in FIGS. 12A-D, and fitting errors associated with the oxygen saturation measurements, are shown in FIGS. 13A and 13B, respectively. In general, the oxygen saturation measurements determined for various locations and fat thicknesses on the subject are similar in magnitude in FIG. 13A. This suggests that Taylor series model fitting is a reliable way to determine which long-distance source is selected for sample measurements. In general, Taylor series model fitting errors (as well as oxygen saturation measurements) are independent of fat thickness, provided that incident radiation penetrates through the skin/fat layer into the muscle and short-distance correction (e.g., orthogonalization) adequately reduces or removes spectral contributions from the skin and fat. In this example, the observation that the different fat thicknesses do not significantly change the calculated oxygen saturation values suggests that light penetration is adequate, and skin and fat correction is sufficient.

Figure 14A:
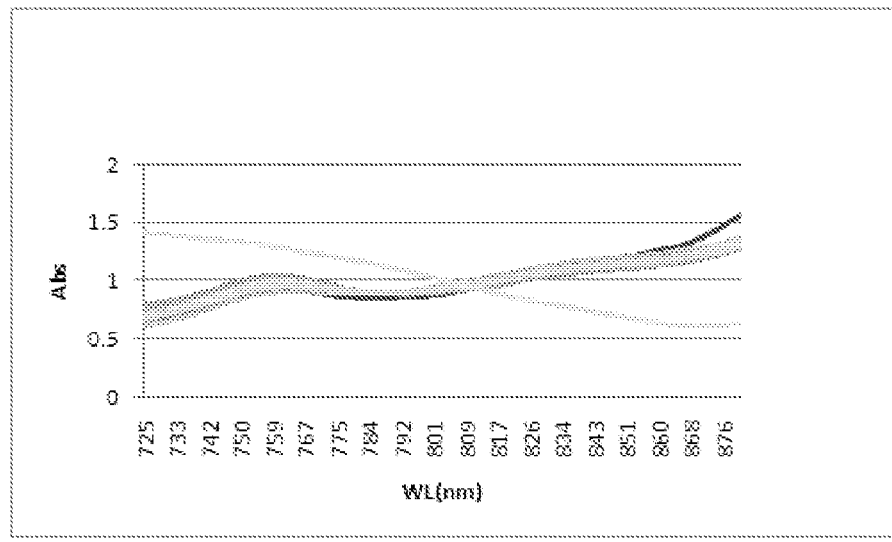
FIG. 14A is a plot showing a temporal sequence of reflectance spectra measured for a test subject.

In addition, spectra that would yield erroneous measurements of oxygen saturation can be identified and removed from further consideration relatively easily by an electronic processor configured to determine the Taylor series model fitting errors. To examine the feasibility of removing abnormal spectra from a measured data set, near infrared spectral reflectance spectra from 34 different adult human subjects were obtained during periods of exercise using a fiber optic probe coupled to a compact spectrometer (Ocean Optics USB2000, available from Ocean Optics, Dunedin, Fla.) at a source-detector spacing of 30 mm. FIG. 14A shows a plurality of spectra measured for one of the 34 subjects. Each of the measured spectra was normalized, fitted to a Taylor series model, and the Taylor series fitting error was calculated.

Figure 14B:
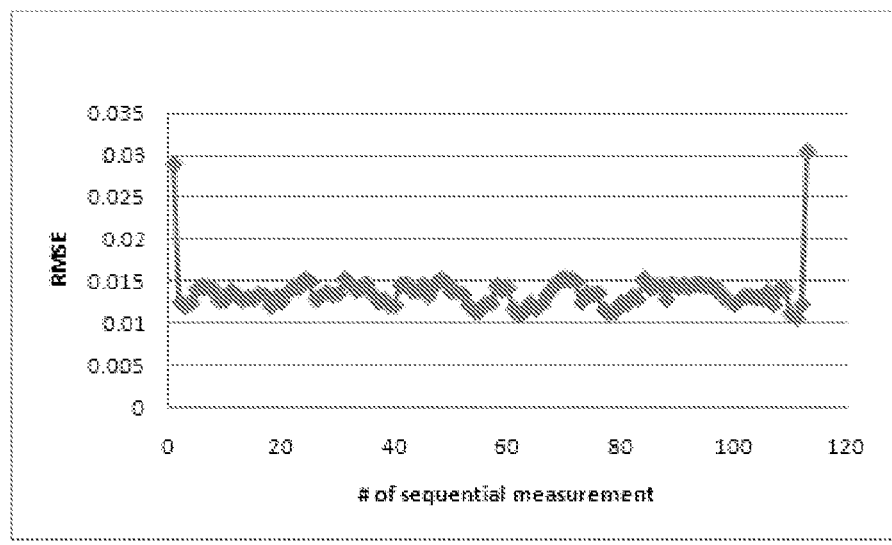
FIG. 14B is a plot showing Taylor series model fitting errors associated with the temporal sequence of spectra shown in FIG. 14A.

The Taylor series fitting errors for each of the spectra are shown in FIG. 14B. From the error plot, it is evident that among the spectra collected for the subject, two (the first and the last spectra recorded) were abnormal; if these spectra were used to determine oxygen saturation, the results would likely be erroneous. The unusually large values of the computed Taylor series fitting error for these two spectra therefore serve as an accurate predictor of abnormal spectra. An electronic processor can implement the Taylor series fitting procedure disclosed above and then, by a process such as thresholding or comparing to a predetermined or previous signal level, can readily identify and remove spectra from the measured data set that are likely to yield calculated parameter values that are erroneous.

Example 2

Figure 15:
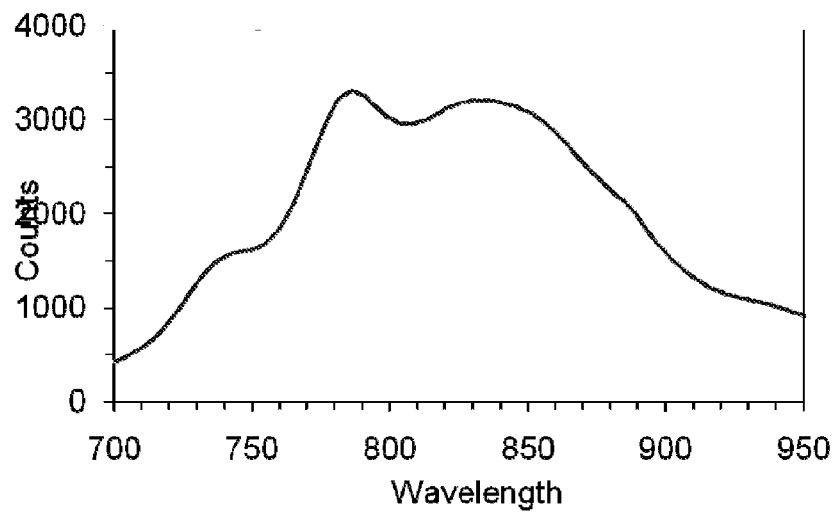
FIG. 15 is a measured spectrum of emitted radiation from a plurality of LEDs where each LED receives the same percentage driving current from a power source.

To examine the synthesis of an incident radiation spectrum by activating multiple individual LEDs, a study was conducted with two different sets of LEDs. The first set of LEDs included diodes configured to emit at the following peak wavelengths: 735, 810, 850, 850, 890, and 940 nm. The second set of LEDs included diodes configured to emit at the following wavelengths: 735, 780, 810, 850, 890, and 940 nm. For each of the sets of LEDs, the driving current applied to each of the LEDs in the set was an adjustable fraction of the maximum driving current for each of the LEDs. In this study, the fraction was adjusted to be equal for each of the individual LEDs in a set. The spectrum for each set, which included emission from each of the LEDs, was measured using a 30 mm source-detector spacing to detect reflected light from a 99% SPECTRALON® reflectance standard. FIG. 15 shows the measured spectrum of the second set of LEDs. The spectrum shown in FIG. 15 suggests that a relatively smooth incident radiation spectrum can be obtained by simultaneously activating multiple LEDs in a particular wavelength region of interest. For near infrared spectral measurements of blood, the most important wavelength is approximately 760 nm, the wavelength of maximum absorption of deoxyhemoglobin. The spectral intensity in the vicinity of 760 nm in FIG. 15 shows a moderate decrease, however. Further, the LED that emits at 940 nm does not appear to contribute significant intensity to the measured incident radiation. Accordingly, a different distribution of individual LED sources might yield a composite spectrum better suited for measuring near infrared reflectance spectra of blood, particularly one in which the 940 nm LED is replaced with a LED having a peak emission wavelength closer to 760 nm. Depending upon the particular applications of the sensor, different distributions of LEDs can be selected for use to improve the quality of measured signals in the near-infrared region of the spectrum.

Example 3

The spectral emission from a set of LEDs is a convolution of the individual emission spectra of the LEDs and the spectral response of the detector. Even when each of the LEDs contributes approximately equally to the overall emission spectrum, as shown in FIG. 15, measured emitted radiation in certain portions of the spectrum can be weaker in intensity than in other parts of the spectrum due to the detector's spectral response function, for example. By way of illustration, in FIG. 15, the radiation intensity between about 700 nm and 780 nm is weaker than the radiation intensity between 780 nm and 860 nm.

Figure 16:
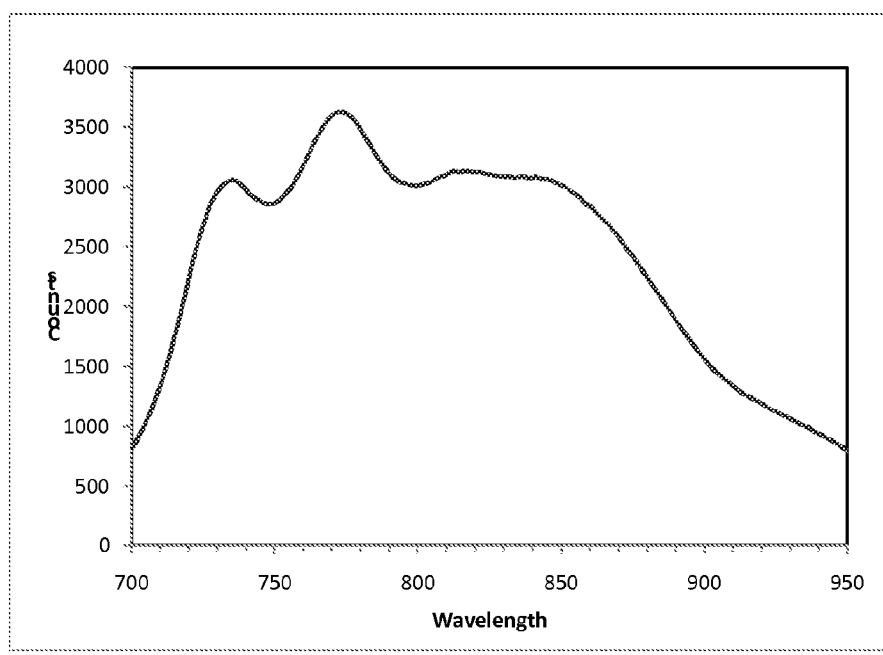
FIG. 16 is a measured spectrum of emitted radiation from a plurality of LEDs where some of the LEDs receive different percentage driving currents from a power source.

To adjust the spectral intensity profile of the combined output of several LEDs, however, different driving voltages can be applied to different LEDs to adjust the relative amount of radiation emitted in different parts of the spectrum. Alternatively, or in addition, the duty cycle of each of the individual LEDs can be adjusted, as discussed previously. In Example 2, the LEDs of the first and second sets were adjusted so that each LED received the same percentage of its maximum drive current as the other LEDs in the same set. In this example, however, the driving currents supplied to individual LEDs in the second set (or, alternatively or in addition, the duty cycles of the LEDs in the second set) were adjusted to increase spectral intensity between 700 nm and 780 nm in the measured emission spectrum for the diode set. Individual diodes in the set were adjusted with the following driving currents (expressed as a percentage of maximum driving current for each LED): 735 nm, 35%; 780 nm, 15%; 810 nm, 15%; 850 nm, 15%; 890 nm, 15%; and 940 nm, 15%. The adjusted LEDs yielded a composite emitted radiation spectrum as shown in FIG. 16. In FIG. 16, the amount of spectral intensity from 700-780 nm relative to the spectral intensity at 760 nm has increased relative to the composite spectrum in FIG. 15. Accordingly, by adjusting the driving currents applied to the LEDs, the duty cycle of the LEDs, or both, the output from each LED can be controlled, affording control over the complete spectral profile of the incident radiation, and permitting compensation for certain hardware and/or intrinsic measurement limitations such as a spectrally-varying detector response.

Example 4

In general, by providing increasing amounts of incident radiation, the one or more sources on the sensors disclosed herein measure stronger reflectance signals, thereby leading to more accurate determinations of parameters based on the detected signals. However, LEDs generate heat during operation, and providing increasing amounts of incident radiation using long-distance sources can lead to heating of a patient's skin, for example, which can make the determination of parameters based on measured radiation signals prone to error. In establishing operating conditions that lead to the provision of sufficient quantities of incident radiation to yield measured reflectance spectra of sufficient quality to accurately determine values of parameters such as oxygen saturation, care should be taken to avoid excessive heating of the patient's skin.

In a series of experiments, the effect of sample heating was investigated by exposing a sample to incident radiation from a set of LEDs while adjusting the overall intensity of the radiation produced by the set. Intensity adjustments were performed by controlling the percentage of maximum operating current (e.g., from 0 to 100%) applied to the LEDs, and by controlling the exposure time (e.g., the amount of time during which the LEDs produce incident radiation and the detector measures reflectance spectra from the sample). The amount of incident radiation produced by the LEDs could also have been controlled by adjusting the duty cycle of the LEDs, or by changing fixed resistors in the driving circuits for each of the LEDs.

Initially, operating conditions were identified that resulted in uniform intensity illumination from all LEDs with exposure times less than 5000 ms. The driving currents supplied to each of the LEDs in this configuration, as a percentage of the maximum current for each LED, were as follows: 735 nm, 35%; 780 nm, 15%; 810 nm, 15%; 850 nm, 15%; 890 nm, 15%; 940 nm, 15%.

Then, a temperature study was performed to determine a maximum allowable exposure time for the sample, and an appropriate duty cycle to ensure that the sample temperature did not exceed 40° C. Temperature studies were initially performed on silicone phantom samples. The determined operating conditions for the LEDs were then confirmed by further experiments on a human test subject to evaluate the effects of temperature on blood flow in skin and muscle. In all experiments, two microthermocouples were used. The first thermocouple was attached to a glass window covering the plurality of long-distance sources on the sensor; this thermocouple yielded a measurement of LED temperature. The second thermocouple was attached to the phantom or test subject in a position near, but not directly under, the sensor. The second thermocouple yielded a measurement of the sample temperature.

Figure 17:
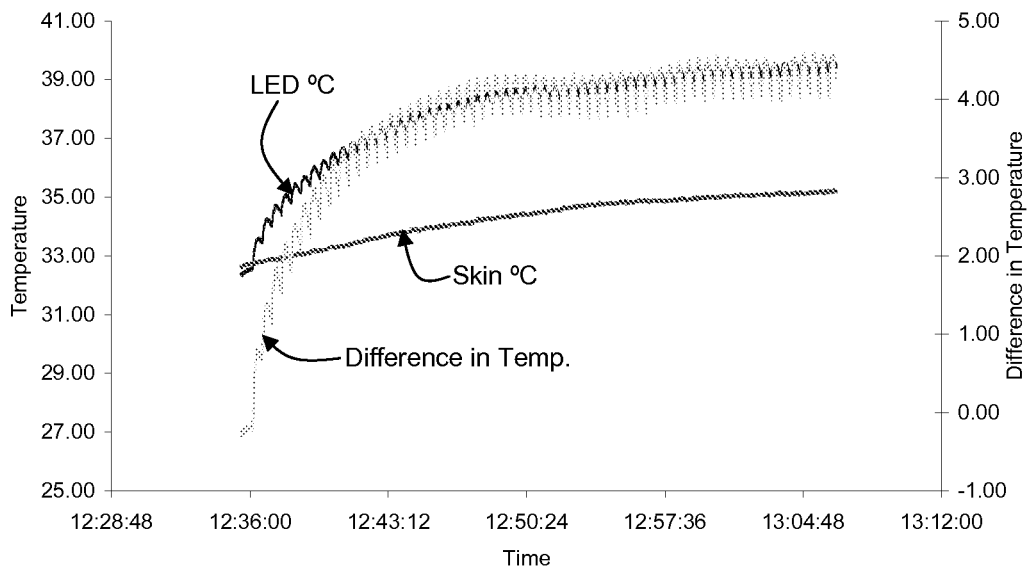
FIG. 17 is a plot showing sample temperature as a function of time during measurement of reflectance spectra from the sample.

During the study, the goal was to adjust the operating conditions of the LEDs while maintaining the temperature readings from both thermocouples below 40° C. Temperature measurements were collected for 30 minutes. FIG. 17 shows a plot of temperature measurement data from each of the thermocouples as well as the calculated difference between the two, as a function of time, for the human test subject. From the silicone phantom studies, it was determined that the exposure time should be limited to a maximum of approximately 4000 ms, and a 30 s delay should be implemented between successive measurements. This protocol was evaluated on the human test subject and produced a skin temperature increase of 4.5° C., but the subject's skin temperature remained below 40° C. The oscillations that were observed in the temperature measurements resulted from successive cycles of 4000 ms exposure of the sample followed by a 26 s cooling period. The temperature relaxation during the cooling period is relatively small in comparison to the overall temperature increase during the sequence of measurements.

Example 5

In some cases, maximum exposure times of 4000 ms may be too small to acquire spectral data of sufficient quality to extract measurements of parameters such as oxygen saturation. To overcome this difficulty, it may be possible to increase the detector's electronic gain to enhance detection of relatively weak reflectance signals from samples. This increased sensitivity can be achieved without increasing sample exposure time, thereby preventing additional sample heating. Increasing the detector gain can be particularly useful, for example, for subjects with relatively dark skin and/or thin layers of fat between the skin surface and the tissue of interest.

A study was performed to investigate the effect of different gain settings on spectral reflectance measurements. Three different detector gain settings were used (nominally, 1.35×, 1.68×, and 2.0×). Measurements were performed on a silicone phantom sample, and on a 99% SPECTRALON® reflectance standard. Measurements were repeated six times, collecting reflectance spectra corresponding to each of six different long-distance sources each time. To ensure that the detector did not saturate, the electronic gain was adjusted to the nominal 2.0× setting and the incident radiation intensity was adjusted to yield a detector reflectance signal of about 3500 counts. Measurements at each of the three gain levels were normalized to measurements without electronic gain.

Figure 18:
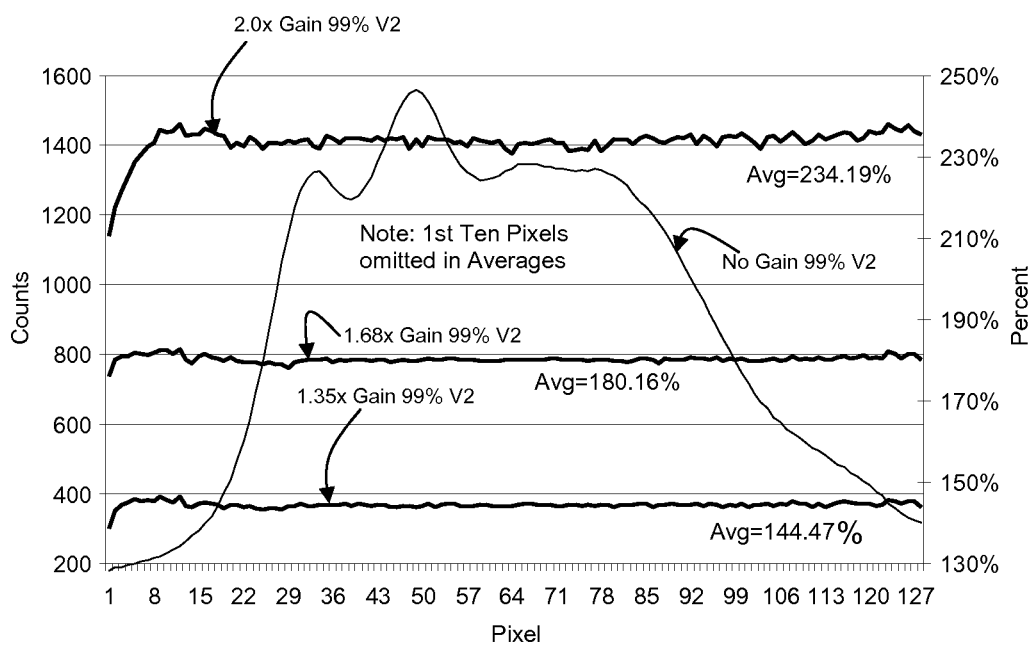
FIG. 18 is a plot showing average gain levels determined for a sensor.

FIG. 18 shows measurement results for the 99% SPECTRALON® reflectance standard illuminated at a source-detector spacing of 30 mm. Results were similar at the other source-detector spacings for the SPECTRALON® standard, and for the phantom sample. FIG. 18 shows the reflectance spectrum with no gain, and at each of the three different gain levels (normalized to remove most of the spectral envelope shape). The resulting gain spectra exhibit very little wavelength dependence (e.g., in FIG. 18, pixel position on the ordinate axis correlates with wavelength). Some variation is visible among the results for the different gain levels in the first eight pixels; accordingly, these pixels are not included in the calculated average gains. Pixels 15-120 were used to determine the gain averages shown in FIG. 18.

Based on the calculated gain averages, it appears that for the particular sensor used in these measurements, a nominal gain setting of 1.35× actually yields a gain of 1.44×. Similarly, a nominal gain setting of 1.68× yields an actual gain of 1.80×, and a nominal gain setting of 2.0× yields an actual gain of 2.34×. The foregoing method can be used to investigate the wavelength dependence of detector electronic gain and calibrate the various gain settings for other sensors.

Example 6

Prior to use, the sensors disclosed herein are typically calibrated to provide accurate wavelength-specific measurements. The sensors determine reflectance and/or absorbance spectra by calculating a ratio of reflected light intensity from a sample to measured light intensity reflected from a reflectance standard. To assess calibration stability of the sensors disclosed herein, a study was performed to standardize an exemplary sensor against a 99% SPECTRALON® reflectance standard (available from Labsphere, North Sutton, N.H.). Radiation reflected from the 99% reflectance standard provided an approximate measure of radiation emitted from the sources of the sensor. The sensor's calibration was compared to the calibration of a fiber optic-based probe that was performed in the same study. For both the sensor and the fiber optic probe, experiments were also performed to measure radiation reflected from 50% and 2% SPECTRALON® reflectance standards as well (also available from Labsphere).

To calibrate the fiber optic probe, the probe was positioned a fixed distance above each reflectance standard, a radiation source was activated to produce incident light, and the probe was used to measure incident light reflected from the reflectance standard. The height of the probe above the reflectance standard was selected to yield spectral reflectance measurements that were as insensitive as possible to small variations in probe height. In general, different heights achieve this condition for long- and short-distance sources. In previous experiments, suitable heights for the fiber optic probe were determined to be 11 mm for short-distance illumination, and 75 mm for long-distance illumination. These heights were used in this study without further investigation.

The exemplary sensor was calibrated in a similar manner against the 99%, 50%, and 2% reflectance standards. For the sensor, a suitable height above the reflectance standards for short-distance illumination was determined to be 16 mm, and for long-distance illumination, a suitable height was determined to be 65 mm. The study was repeated for all pairs of short and long distance sources on the sensor, under the additional constraint that the selected heights were those that yielded measured data that were the most insensitive to differences in the long-distance source-detector spacing.

By standardizing the fiber optic probe against known reflectance standards, calibration equations developed for similar probes could be transferred to the probe in this study as described, for example, in Soyemi et al., "Standardization method for correcting spectral differences across multiple units of a portable near infrared-based medical monitor," Proc. SPIE 5702: 135-142 (2005), and in U.S. Patent Application Publication No. US 2007/0112258, the entire contents of each of which are incorporated herein by reference. The calibration process permits compensation for variations among different probes resulting from manufacturing-induced variability in optical components, for example.

Figure 19A:
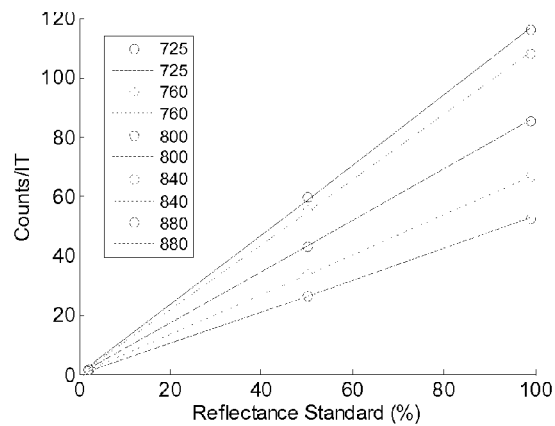
FIGS. 19A-B are plots showing measured light intensity as a function of nominal reflectance standard for a fiber optic probe and a sensor using a long source-detector distance.
Figure 19B:
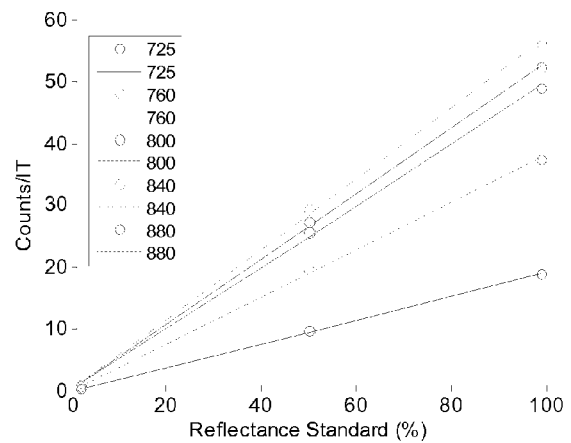

To examine whether calibration equations developed for other systems (e.g., fiber optic probes and/or other sensors of the type disclosed herein) could be transferred to the sensor in this study, the linearity of the measured response of the sensor, for both short- and long-distance illumination of the sample, was investigated for the different reflectance standards at five different wavelengths (725 nm, 760 nm, 800 nm, 840 nm, and 880 nm). FIGS. 19A and 19B show intensity measurements from the different reflectance standards for the fiber optic probe and the sensor, respectively, at each of the five different wavelengths. FIGS. 19A and 19B correspond to a source-detector spacing of 30 mm. As shown in these figures, the measured intensity response of both the fiber optic probe and the sensor scales approximately linearly with the nominal reflectance of the standards. Accordingly, calibration equations can be successfully transferred to both the fiber optic probe and the sensor without significant errors due to nonlinear detector response.

Figure 20A:
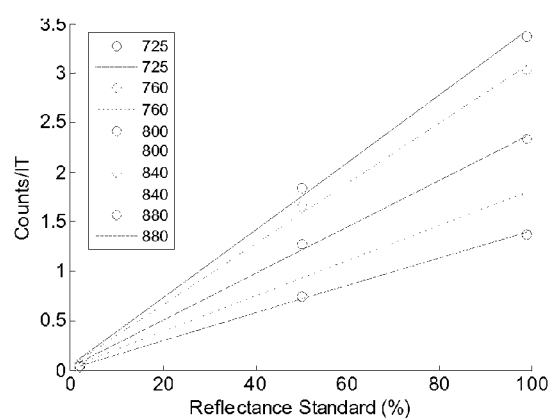
FIGS. 20A-B are plots showing measured light intensity as a function of nominal reflectance standard for a fiber optic probe and a sensor using a short source-detector distance.
Figure 20B:
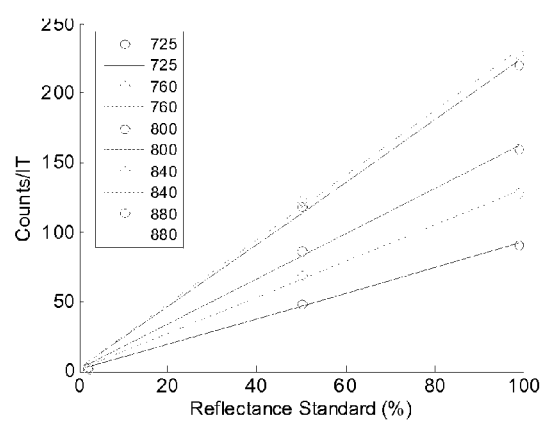

FIGS. 20A and 20B show intensity measurements from the different reflectance standards at a source-detector spacing of 3 mm for the fiber optic probe and the sensor, respectively. The measured intensity response of both the fiber optic probe and the sensor scales approximately linearly with the nominal reflectance of the standards, so that calibration equations can be successfully transferred to both the probe and the sensor for short-distance illumination as well.

Sensors are typically wavelength-calibrated to map specific detector pixels to particular wavelengths of radiation. Various methods can be used to calibrate the sensors disclosed herein for wavelength-dependent measurements. A study was performed to evaluate different wavelength calibration methods. The calibration methods were each referenced to a single spectral peak in the reflectance spectrum of a test subject. The test subject was subjected to vascular occlusion for 10 minutes, followed by a one minute period of exercise. Most hemoglobin in the subject's blood was converted to deoxyhemoglobin via this procedure; deoxyhemoglobin has a characteristic absorption peak at 760 nm.

Two different radiation sources were used to provide incident radiation for wavelength calibration. The first source included six near infrared LEDs. The second source included three near infrared laser diodes. The laser diodes typically had narrower spectral emission peaks than the LEDs. The actual wavelengths of the emission peaks of the individual LEDs and laser diodes were measured using a calibrated spectrometer (Ocean Optics USB2000, available from Ocean Optics, Dunedin, Fla.). The selected radiation source in a particular experiment was used to either illuminate the sensor directly, or to illuminate a 99% reflectance standard spaced from the sensor by a distance of 65 mm. For both types of illumination, the radiation source was positioned in the same horizontal plane as the sensor's detector, and spaced from the detector by 30 mm. The sensor was used to measure either the direct illumination or the reflected radiation from the standard.

Figure 21:
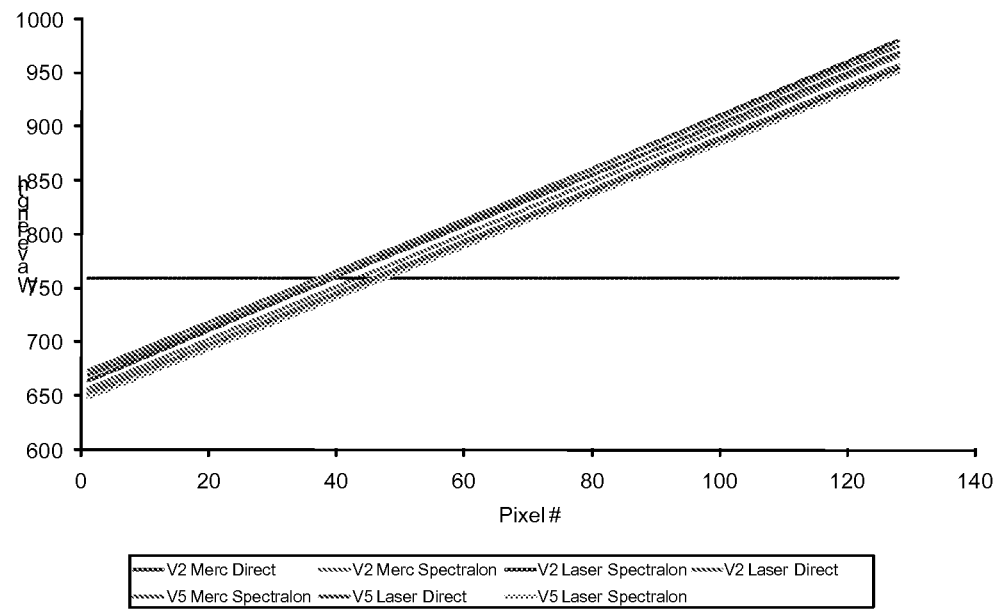
FIG. 21 is a plot showing wavelength calibration curves measured using different sensor calibration methods.

FIG. 21 shows wavelength calibration results for different combinations of radiation sources and illumination geometries for two different sensors ("V2" and "V5"). For each sensor, direct illumination leads to detection of the 760 nm peak at a slightly different pixel position than illumination with light reflected from the reflectance standard. When these spectral results were compared with wavelength calibration measurements recorded from a human tissue sample, it was observed that detection of radiation generated by LEDs and reflected from the reflectance standard produced a calibration that most reliably reproduced the position of the dexoyhemoglobin peak at 760 nm in the human tissue sample. Without wishing to be bound by theory, it is believed that this calibration method produced the most accurate results, because it most closely approximates experimental conditions when real tissue samples are illuminated and their spectra measured. Accordingly, LED-based illumination and detection of reflected light from a 99% reflectance standard was the method selected for use to calibrate the sensors disclosed herein for wavelength.

Figure 22:
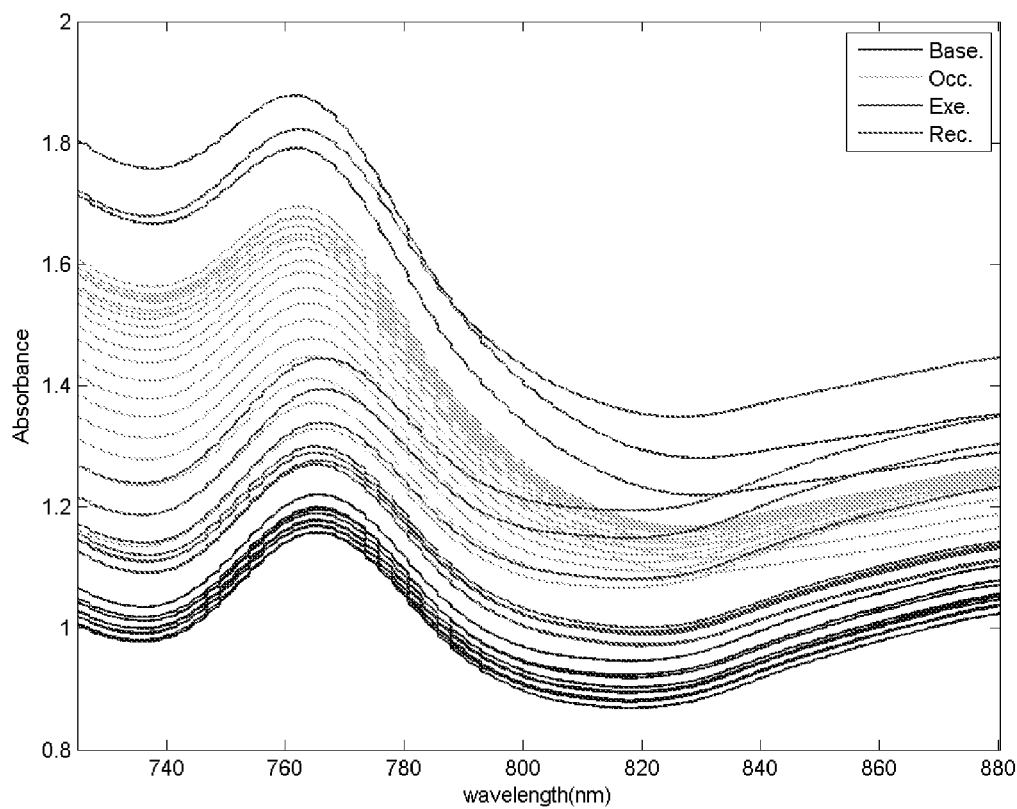
FIG. 22 is a plot showing a series of reflectance spectra obtained over time during an arterial occlusion test protocol.

During the course of the study, the main peak—attributed to deoxyhemoglobin above—shifted to slightly different wavelengths. For example, the peak appeared closest to 760 nm near the end of occlusion and during exercise, and shifted to wavelengths further away from 760 nm during recovery. Exemplary reflectance spectra demonstrating this effect are shown in FIG. 22. Each of the spectra shown in FIG. 22 includes an admixture of the pure spectra of both deoxyhemoglobin and oxyhemoglobin in a proportion defined by the oxygen saturation parameter. The deoxyhemoglobin peak at 760 nm has a molar extinction coefficient of 1.67 $mM^{-1} cm^{-1}$. Between 800 nm and 900 nm, deoxyhemoglobin has an extinction coefficient of approximately 0.8 $mM^{-1} cm^{-1}$, while oxyhemoglobin absorbance increases from about 0.8 $mM^{-1} cm^{-1}$ at 800 nm to about 1.34 $mM^{-1} cm^{-1}$ at 900 nm. As the concentration of oxyhemoglobin increases during recovery, absorption at wavelengths larger than 760 nm begins to increase relative to absorption at wavelengths less than 760 nm, and so the overall spectral peak shifts to longer wavelengths. FIG. 23 shows oxygen saturation calculated from the reflectance spectra shown in FIG. 22 and plotted as a function of time. During occlusion, as oxygen saturation falls and the proportion of deoxyhemoglobin in the subject's blood increases, the deoxyhemoglobin peak shifts closer to 760 nm. During recovery, as oxygen saturation increases and the proportion of oxyhemoglobin in the subject's blood increases, the deoxyhemoglobin peak shifts further away from 760 nm.

Example 7

The various source-detector spacings provided by the sensors disclosed herein permit non-invasive interrogation of tissues that include overlying fat layers of various thicknesses. A study was performed to determine the penetration depth of radiation from various sources on the sensors. Two-layer phantoms were prepared using methods described in, for example, Yang et al., "Simultaneous correction of skin color and fat thickness for tissue spectroscopy using a two-distance fiber optic probe and orthogonalization techniques," Optics Letters, 30: 2269-2271 (2005), the entire contents of which are incorporated by reference. In the phantoms, fat was simulated with agar containing a known amount of intralipid so that the reduced scattering coefficient ($\mu''_s$) is similar to that of fat. The fat layers were poured into molds of known thickness to produce fat layers 2, 4, 6, 8, 10, and 20 mm thick, so that fat thicknesses between 2 mm and 20 mm in increments of 2 mm could be obtained by combining no more than 2 phantoms. Skin layers 1 mm thick were molded to produce medium- and dark-toned skin phantoms with reduced scattering coefficients adjusted to match the reduced scattering coefficient of real skin by adding melanin to the phantoms (0.15 mg/mL and 0.25 mg/mL for medium- and dark-toned skin, respectively). A skin layer was placed on a fat layer (consisting of one or two of the fat phantoms), and the layers were placed on a black, highly absorbing support material. Reflectance spectra were measured for each phantom using both a fiber optic probe and one of the sensors disclosed herein. Spectra recorded using the sensor were measured using a variety of different signal acquisition times. To determine depth penetration of the incident radiation, the intensity of the reflected radiation was measured as a function of fat thickness. In theory, an S-shaped curve, as shown in FIG. 24, is expected to describe the relationship between reflected radiation intensity and fat thickness. In particular, if radiation penetrates completely through the skin and fat layers, it is absorbed by the black support material; the measured reflectance signal is therefore relatively small. However, when radiation only partially penetrates into the skin and fat layers, a larger fraction of the incident radiation is reflected and reaches the detector; thus, the measured reflectance signal increases. The measured reflectance signal reaches a maximum when nearly all of the incident radiation fails to penetrate the skin and fat layers and is reflected (e.g., the plateau in intensity at large thickness values in FIG. 24).

Figure 25A:
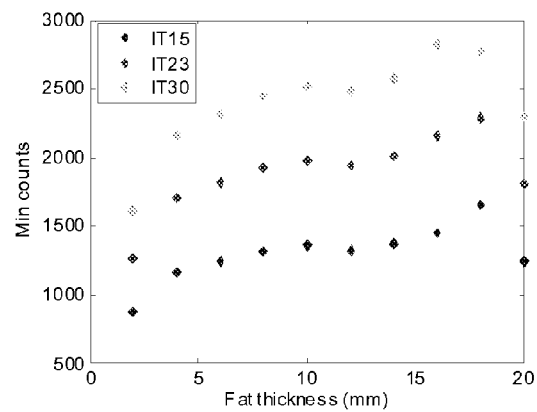
FIGS. 25A-B are plots showing sensor-measured reflected radiation intensity as a function of fat thickness for medium- and dark-toned tissue phantoms, respectively, using a short source-detector spacing.
Figure 25B:
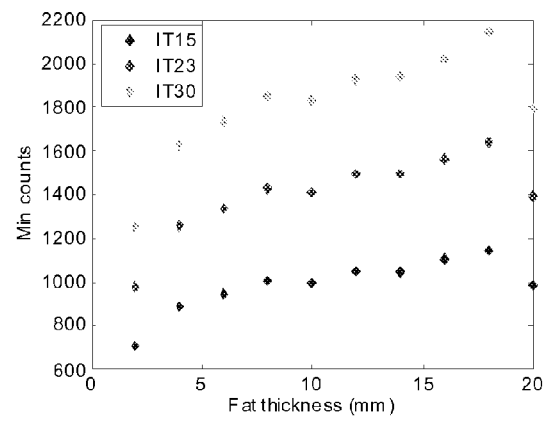

FIGS. 25A and 25B show reflected radiation intensity measured as a function of fat thickness for phantoms with medium-toned (FIG. 25A) and dark-toned (FIG. 25B) skin, respectively. In these figures, the lower plateau region at small fat thicknesses is missing, indicating that none of the incident radiation penetrates to the absorbing support material. This situation is desirable; if the short-distance spectra included contributions from radiation absorption by the tissue of interest, these contributions would be removed from the corrected data that represents only the target of interest, yielding erroneous data. The spectra in FIGS. 25A-B appear to level off between fat thicknesses of 6 mm and 8 mm, indicating that short-distance illumination (at the particular selected short distance) can be used to reduce the effects of overlying skin and fat layers of thicknesses up to 6-8 mm.

Figure 27:
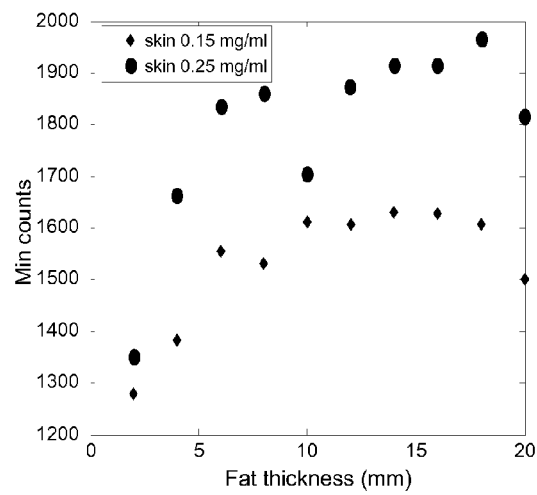
FIG. 27 is a plot showing fiber optic probe-measured reflected radiation intensity as a function of fat thickness for medium- and dark-toned tissue phantoms using a short source-detector spacing.

FIG. 27 shows reflected radiation intensity as a function of fat thickness for the same phantoms as in FIGS. 25A and 25B, but measured with a fiber optic probe. The fiber optic results also indicate that for the same short-distance illumination as in FIGS. 25A-B, the incident radiation penetrates to a depth of 6-8 mm.

Figure 26A:
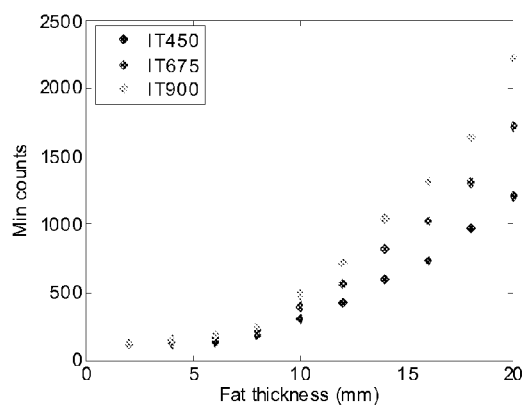
FIGS. 26A-B are plots showing sensor-measured reflected radiation intensity as a function of fat thickness for medium- and dark-toned tissue phantoms, respectively, using a long source-detector spacing.
Figure 26B:
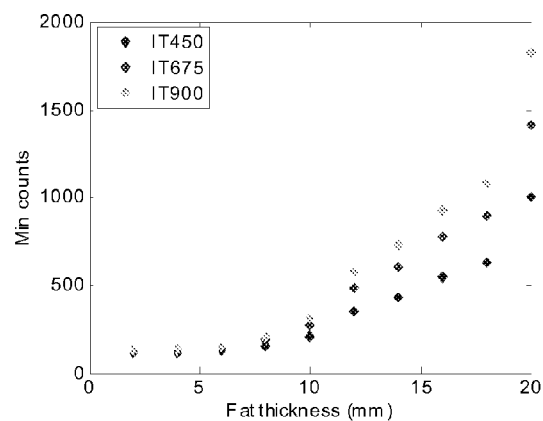
Figure 28:
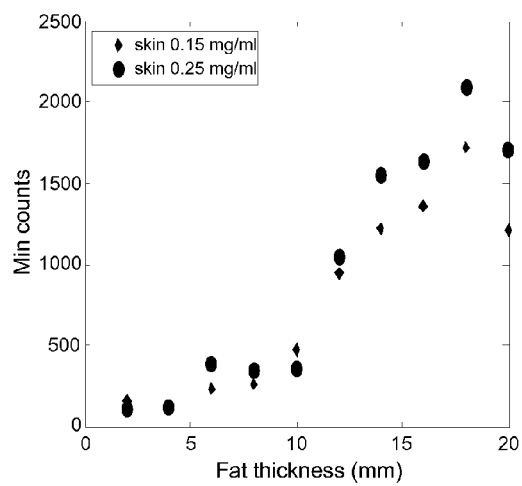
FIG. 28 is a plot showing fiber optic probe-measured reflected radiation intensity as a function of fat thickness for medium- and dark-toned tissue phantoms using a long source-detector spacing.

Long-distance illumination experiments were also performed on the tissue phantoms. Both the fiber optic probe and the sensor were used to obtain reflectance spectra at a source-detector spacing of 30 mm. FIGS. 26A and 26B show reflected radiation intensity as a function of fat thickness for long-distance illumination, measured with the sensor, for medium-toned and dark-toned skin phantoms. FIG. 28 shows measurement results under similar conditions obtained using the fiber optic probe. The data in FIGS. 26A-B and 28 show that the long-distance incident radiation penetrates fat thicknesses of at least 8-10 mm, and still provides a significant amount of signal from the underlying target. Even for thicker fat layers, the measured intensities of the reflected radiation have not reached an upper plateau, indicating the further information about tissues underlying the fat layer may be obtained.

The target concentration dependence was also investigated in a series of measurements. Three-layer phantoms including layers of muscle, fat, and skin were fabricated according to the methods described in, for example, Yang et al., "Removal of analyte-irrelevant variation in near infrared tissue spectra," Applied Spectroscopy, 60: 1070-1077 (2006), the entire contents of which are incorporated herein by reference. The absorber in the muscle layer was India ink, and the scattering coefficient of the muscle layer was adjusting by adding 20% intralipid. Three different concentrations of melanin were used in the skin layers to produce light, medium, and dark skin tones. New fat and skin layers were fabricated each time new muscle layers were fabricated. All phantoms were refrigerated overnight and sealed to avoid moisture loss. The composition of the various muscle, fat, and skin layers are shown in Tables 1, 2, and 3, respectively.

TABLE 1

| Phantom | Reduced Scattering Coefficient (cm$^{-1}$) | Ink Conc. | Ink Used (mL of 10% sol'n) | Intralipid 20% (mL) | Water (mL) | Agar (g) |
|---|---|---|---|---|---|---|
| 1 | 7.0 | 0.00550% | 0.330 | 21 | 578.67 | 6 |
| 2 | 7.0 | 0.00600% | 0.360 | 21 | 578.64 | 6 |
| 3 | 5.0 | 0.00550% | 0.330 | 15 | 584.67 | 6 |
| 4 | 5.0 | 0.00600% | 0.360 | 15 | 584.64 | 6 |
| 5 | 7.0 | 0.00650% | 0.390 | 21 | 578.61 | 6 |
| 6 | 7.0 | 0.00700% | 0.420 | 21 | 578.58 | 6 |
| 7 | 5.0 | 0.00650% | 0.390 | 15 | 584.61 | 6 |
| 8 | 5.0 | 0.00700% | 0.420 | 15 | 584.58 | 6 |
| 9 | 7.0 | 0.00750% | 0.450 | 21 | 578.55 | 6 |
| 10 | 5.0 | 0.00750% | 0.450 | 15 | 584.55 | 6 |

TABLE 2

| Phantom | Reduced Scattering Coefficient (cm-1) | Intralipid 20% (mL) | Water (mL) | Agar (g) |
|---|---|---|---|---|
| Fat (3, 5, 7 mm) | 12 | 48 | 752.0 | 8 |

TABLE 3

| Phantom | Melanin Final Concentration (mg/mL) | Melanin (mL of 1 mg/mL stock solutionn) | Intralipid 20% (mL) | Water (mL) | Agar (g) |
|---|---|---|---|---|---|
| 1 | 0.05 | 5 | 7.5 | 87.5 | 2 |
| 2 | 0.15 | 15 | 7.5 | 77.5 | 2 |
| 3 | 0.25 | 25 | 7.5 | 67.5 | 2 |

Phantoms consisting of materials representing muscle only, and of materials representing muscle, fat, and skin, were measured in parallel using both a fiber optic probe and an exemplary one of the sensors disclosed herein. A neutral density filter was attached to the short-distance source of the sensor to reduce the intensity of incident radiation produced by the short-distance source. The output radiation intensities of each of the selected short- and long-distance sources for the sensor were adjusted by controlling the driving currents applied to each of the LEDs in each source. Driving currents applied to the short-distance source LEDs, expressed as a percentage of maximum driving current for each LED, were as follows: 735 nm, 17%; 780 nm, 5%; 810 nm, 2%; 850 nm, 2%; 890 nm, 2%; and 940 nm, 2%. Driving currents applied to the long-distance source LEDs, expressed as a percentage of maximum driving current for each LED, were as follows: 735 nm, 35%; 780 nm, 15%; 810 nm, 15%; 850 nm, 15%; 890 nm, 15%; and 940 nm, 15%.

Before undertaking measurements with the sensor and the fiber optic probe, both the short- and long-distance sources of the sensor and the probe were calibrated against 99%, 50%, and 2% SPECTRALON® reflectance standards as discussed above. The measurement acquisition times were selected to achieve as many intensity counts as possible on the sensor's detector as possible. All reference and sample spectra were normalized according to the acquisition times prior to performing further calculations based on the spectra.

Following measurement and normalization of spectra from the three-layer phantoms using both the fiber optic probe and the sensor, the spectra were analyzed using partial least squares (PLS) methods to predict the ink concentration in each measured phantom. The total number of spectra in each set was 90. The long-distance spectra were orthogonalized using the short-distance spectra according to the method of Andersson (see, for example, Yang et al., "Simultaneous correction of skin color and fat thickness for tissue spectroscopy using a two-distance fiber optic probe and orthogonalization technique," Optics Letters 30: 2269-2271 (2005), and U.S. Pat. No. 7,532,919, the entire contents of each of which are incorporated by reference). Next, the orthogonalized spectra were processed by PCALC as necessary, and the PLS model with cross validation was calculated. All spectra and concentrations were mean centered. The cross validation method included leaving random groups of 20% of all sample spectra out at each pass until all spectra had been predicted. Cross validation of all spectra was repeated for 20 iterations and averaged results were reported. The model calculations were repeated four times to obtain averaged correlation coefficient ($R^2$) and root mean-square error of cross-validation (RMSECV) values.

Residual plots of the sample spectra were examined for spectral outlier candidates using Q residuals, Hotelling $T^2$ residuals, Y Studentized residuals, and Leverage plots. Q residuals were used to identify lack of fit between spectra and the PLS model. Y Studentized residuals were used to identify spectra with large differences between measured and predicted concentrations. Hotelling $T^2$ residuals and Leverage plots were used to identify differences between an individual spectrum and the other spectra. Samples with residuals much larger than the residuals of the rest of the samples were taken to be indicative of measurement error.

The foregoing analysis was repeated for spectra with different pre-processing, and spectra measured with two different instruments (e.g., two different sensors). To determine whether RMSECV differences between instruments was statistically significant, a formal statistical analysis of the concentration residuals was performed for the orthogonalized set of spectra (Andersson orthogonalization) after PCALC. The method used was a two-way fixed effects ANOVA test of the concentration residuals for each sample spectrum organized in two groups from each spectrometer. The residuals were calculated as the square of differences between the mean value for a particular sample and instrument and measured values for the sample and instrument. Outlier samples from the two sets were removed from both sets before analysis to ensure equal sample numbers (83) in each group.

Results from the PLS analysis for spectra measured with the fiber optic probe are shown in Table 4. Applying PCALC preprocessing generally appears to improve concentration prediction, as measured by the $R^2$ and RMSECV values. Orthogonalization appeared to contribute more to the improvement of results than PCALC preprocessing. For this set of phantoms, orthogonalization removed or reduced spectral interference from skin and fat layers, while PCALC reduces spectral variations arising from the muscle layer that arise from variations in the reduced scattering coefficient. The phantoms investigated included only two different reduced scattering coefficients, and the values of the different coefficients were still relatively close.

TABLE 4

| Model | PLS Factors | $R^2$ | 10 x RMSECV (%) |
|---|---|---|---|
| Spectral orthogonalization | 7 | 0.639 | 4.33 |
| Spectral orthogonalization with preprocessing | 6 | 0.652 | 4.24 |

TABLE 4-continued

| Model | PLS Factors | $R^2$ | 10 x RMSECV (%) |
|---|---|---|---|
| Long distance absorbance spectra | 9 | 0.590 | 4.63 |
| Long distance absorbance spectra with preprocessing | 8 | 0.596 | 4.62 |

In the investigated phantoms, strong absorption of incident radiation by the India ink limits the concentration range that can be investigated. As a result, the concentration differences between different phantoms in the study were relatively small (e.g., concentrations of 0.0055, 0.0060, 0.0065, 0.0070, and 0.0075% were used). Spectral variations due to such small concentration differences can be comparable in magnitude to variations due to other factors such as scattering of incident radiation in the muscle and fat layers. In addition, India ink does not have well defined spectral absorption peaks in the near infrared region; accordingly, the spectral contribution of the India ink is convolved with the scattering contribution from Intralipid. Similar problems do not arise for human test subjects, which have well-defined absorption peaks, and in which concentration-induced changes in hemoglobin spectra are readily identified.

TABLE 5

| Model | PLS Factors | $R^2$ | 10 x RMSECV (%) |
|---|---|---|---|
| Spectral orthogonalization | 9 | 0.5797 | 0.4775 |
| Spectral orthogonalization with preprocessing | 9 | 0.6214 | 0.4425 |
|  | 8 | 0.6208 | 0.4427 |
|  | 9 | 0.6227 | 0.4423 |
| Long distance absorbance spectra | 6 | 0.4841 | 0.525 |
| Long distance absorbance spectra with preprocessing | 6 | 0.5071 | 0.502 |
|  | 6 | 0.5006 | 0.505 |

Table 5 shows the results from the PLS analysis for spectra measured with the sensor. As in Table 4, the data in Table 5 show that PCALC preprocessing of spectra provides improved prediction results, as does spectral orthogonalization, for spectra measured with the sensor. ANOVA results for significance level $\alpha=0.05$ showed a p-value of 0.769, indicating that differences between RMSECV for similar (but different) sensors is not statistically significant.

To examine differences between the performance of the fiber optic probe and the sensor on human test subjects, a group of test subjects was subjected to an identical test protocol on two separate occasions. Upon an initial visit to the research laboratory, each subject underwent a test protocol that included cuff occlusion at 90 mm over systolic blood pressure, followed by 1 minute of handgrip exercise with occlusion. Reflectance spectra were measured using the fiber optic probe. During the second visit to the laboratory (at least 48 hours later), each subject underwent the same protocol, and reflectance spectra were measured with the sensor.

The sensor was calibrated each day against three different reflectance standards, as discussed above. The sensor was attached to each subject's flexor digitorum profundus with medical grade adhesive. Spectra were measured every 30 seconds and muscle oxygen saturation was calculated throughout the entire protocol using methods described in, for example, Yang et al., "Quantitative measurement of muscle oxygen saturation without influence from skin and fat using continuous-wave near infrared spectroscopy," Optics Express 15: 13715-13730 (2007), the entire contents of which are incorporated herein by reference). To compare the results from different subjects, four time points in the study were identified and muscle oxygen saturation values for all of the subjects at each of the time points were averaged. The identified time points were as follows: baseline (final 3 minutes before occlusion); occlusion (final 3 minutes before hand grip exercise); exercise (1 minute hand grip exercise and occlusion); and recovery (first 3 minutes after occlusion released). Values of muscle oxygen saturation determined by the fiber optic probe and by the sensor at each time point were compared using a paired t-test with $p<0.05$ considered significant.

Figure 29:
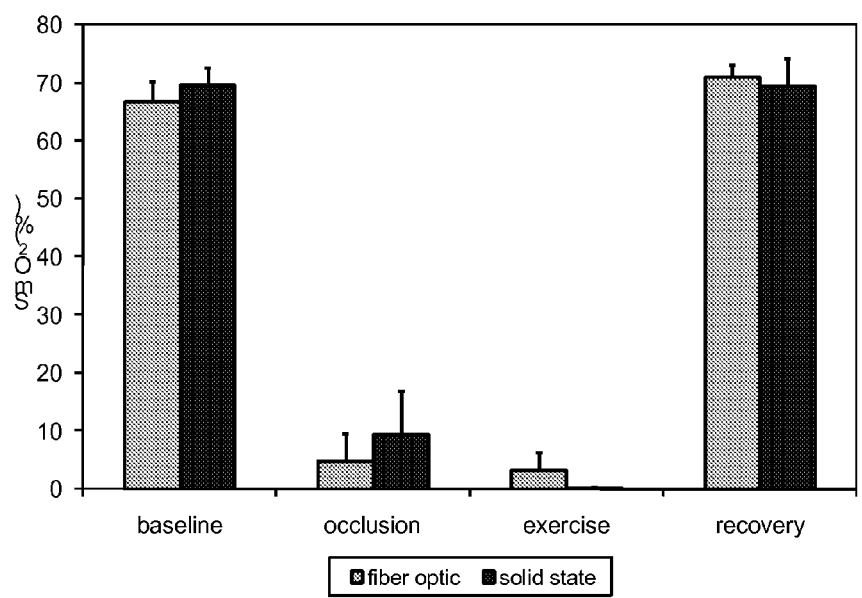
FIG. 29 is a bar chart showing calculated values of muscle oxygen saturation at different points during a test protocol for a fiber optic probe and a sensor.

The muscle oxygen saturation results for the fiber optic probe and the sensor are shown in Table 6, and in FIG. 29. At all stages of the test protocol, the measurement results obtained from the fiber optic probe and the sensor are similar, indicating that the sensor is a suitable replacement for the fiber optic probe in various applications.

TABLE 6

| Measurement Device | Protocol Stage Baseline | Occlusion | Exercise | Recovery |
|---|---|---|---|---|
| fiber optic probe | 66.63 ± 8.9 | 4.78 ± 10.69 | 3.20 ± 7.15 | 70.90 ± 5.50 |
| sensor | 69.52 ± 7.8 | 9.36 ± 16.88 | 0.14 ± 0.31 | 69.50 ± 11.58 |

The measured spectra were also used to investigate the feasibility of using the sensor to determine muscle pH. Typically, the method for calculating muscle pH depends more strongly on the optical system used to obtain reflectance spectra than the method used to calculate muscle oxygen saturation. Muscle pH is calculated from the measured spectra using a partial least squares model which was developed for the fiber optic probe (see, for example, Soller et al., "Non-invasive determination of exercise-induced hydrogen ion threshold through direct optical measurement," Journal of Applied Physiology 104: 837-844 (2008), the entire contents of which are incorporated herein by reference). Small differences in spectra measured with the fiber optic probe and the sensor were significant enough that the PLS model equations developed for the probe could not be directly applied to the spectra collected with the sensor.

To investigate the feasibility of developing muscle pH models directly for spectra measured with the sensor, pH values determined using the fiber optic probe were used as "known" pH values for PLS model development, relative to spectra measured using the sensor at corresponding time points in the test protocol. Spectra measured using the sensor were orthogonalized and outliers were removed. The model accuracy was evaluated with "random subsets" cross-validation with 5 data splits and 20 iterations. A model was developed for each separate test subject.

TABLE 7

| Subject | Number of Factors | $R^2$ | RMSECV | Number of Analysis Points |
|---|---|---|---|---|
| 1 | 1 | 0.913 | 0.026 | 41 |
| 3 | 2 | 0.964 | 0.060 | 41 |
| 4 | 1 | 0.989 | 0.035 | 41 |
| 5 | 3 | 0.982 | 0.046 | 42 |
| 6 | 3 | 0.983 | 0.029 | 41 |
| 7 | 2 | 0.952 | 0.080 | 41 |

Figure 30:
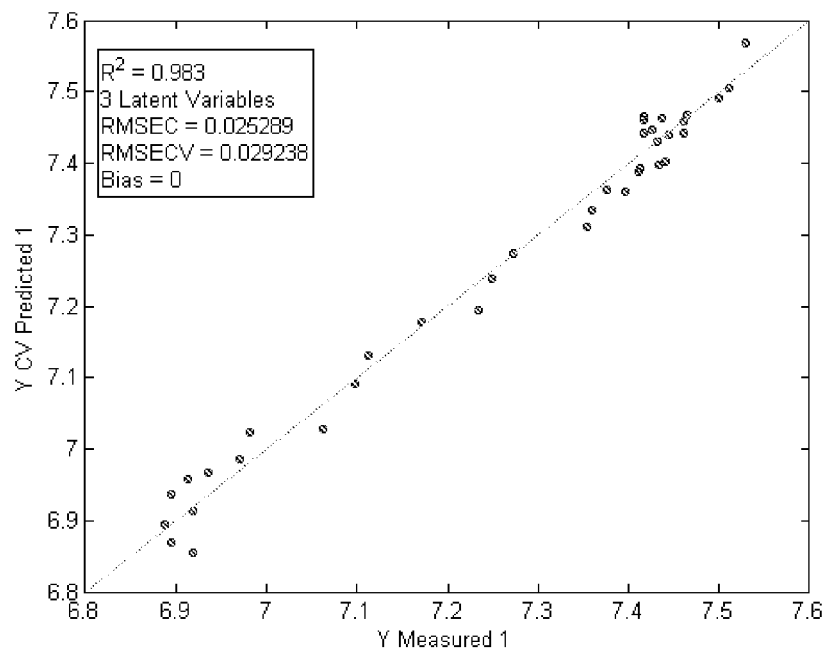
FIG. 30 is a plot showing a correspondence between known values of muscle pH in a test subject and values of muscle pH derived from reflectance spectra measured with a sensor.

Accuracy metrics for each of six test subjects are shown in Table 7. The $R^2$ values for each model provide an indication of the model's trending capability, and the RMSECV values provide estimates of each model's accuracy. FIG. 30 shows the correspondence between known and calculated muscle pH values for one of the test subjects. In general, among the test subjects, $R^2$ values are high and RMSECV values are low compared to the range of measured pH (6.9-7.5). These results are comparable to data obtained using pH measurement electrodes in rabbit muscle during vascular occlusion (see, for example, Zhang et al., "Partial least-squares modeling of near-infrared reflectance data for noninvasive in vivo determination of deep-tissue pH," Applied Spectroscopy 52: 400-406 (1998), the entire contents of which are incorporated by reference herein). The rabbit spectra were obtained directly from muscle tissue, while in this study, the muscle spectra were obtained by illuminating the muscle tissue through layers of skin and fat, and correcting the measured spectra to reduce or eliminate contributions from the skin and fat layers prior to model development. This further suggests that the sensors disclosed herein can be used to obtain accurate estimates of a wide variety of physiological parameters, including parameters that are relatively sensitive to the optical arrangement used to measure the reflectance spectra.

Other Embodiments

A number of embodiments have been described. Nevertheless, it will be understood that various modifications may be made without departing from the spirit and scope of the disclosure. Accordingly, other embodiments are within the scope of the following claims.

What is claimed is:

1. A sensor, comprising:
  a circuit board comprising an electronic processor;
  a plurality of radiation sources, each source being mounted directly to the circuit board; and
  a spectral detector attached to the circuit board, the spectral detector being configured to analyze radiation derived from one or more of the plurality of radiation sources,
  wherein the plurality of radiation sources comprises a short-distance source positioned at a distance of 9 mm or less from the detector, and at least two long-distance sources each positioned at different distances at least 10 mm from the detector; and
  wherein during operation of the sensor, the electronic processor is configured to:
    select one of the at least two long-distance sources by:
      (i) exposing a subject to incident radiation produced by one of the long-distance sources;
      (ii) measuring reflected or transmitted radiation from the subject using the spectral detector;
      (iii) repeating (i) and (ii) for each of the long-distance sources to generate spectral information corresponding to each of the long-distance sources;
      (iv) comparing the spectral information for each of the long-distance sources to expected peak information to determine which ones of the long-distance sources are suitable for illumination of the subject; and
      (v) selecting one of the suitable long-distance sources from (iv) based on acquisition times associated with the spectral information corresponding to each of the suitable long-distance sources;
    expose the subject to incident radiation from the short-distance source and from the selected long-distance source and use the spectral detector to measure radiation from the subject corresponding to illumination by the short-distance source and the selected long-distance source; and
    analyze the measured radiation to determine one or more properties of the subject.

2. The sensor of claim 1, wherein the electronic processor is configured to selectively adjust at least one of (i) a duty cycle of, and (ii) an electrical drive current supplied to, one or more of the plurality of radiation sources to produce incident radiation having a selected spectral shape.

3. The sensor of claim 1, wherein the plurality of radiation sources comprises at least two short-distance sources and at least three long-distance sources.

4. The sensor of claim 1, wherein the electronic processor is further configured to:
  calculate an absorbance spectrum for the subject corresponding to illumination of the subject by the short-distance source;
  calculate an absorbance spectrum for the subject corresponding to illumination of the subject by the selected long-distance source; and
  correct the absorbance spectrum corresponding to illumination by the long-distance source to reduce spectral effects due to layers of skin and fat in the subject using information derived from the absorbance spectrum corresponding to illumination by the short-distance source.

5. The sensor of claim 1, further comprising a display unit, wherein the display unit is positioned on a surface of the sensor opposite to a surface through which the incident radiation is emitted by the plurality of radiation sources, and wherein the display unit is configured to display values of at least some of the one or more properties of the subject and previously measured values of the one or more properties of the subject.

6. The sensor of claim 1, further comprising a communication interface comprising a wireless transmitter and receiver configured to transmit data to and from the sensor, wherein the sensor is configured to transmit the data over a network.

7. The sensor of claim 1, wherein the one or more properties comprise at least one of oxygen saturation, oxygen tension, pH, hematocrit, hemoglobin concentration, anaerobic threshold, water content, and oxygen consumption of the subject.

8. The sensor of claim 1, wherein the electronic processor is configured to maintain a non-zero measured detector signal intensity within a predetermined range of signal intensities during measurement of the radiation from the subject.

9. The sensor of claim 8, wherein the electronic processor is configured to maintain the detector signal intensity within a predetermined range by adjusting at least one of an electronic gain of the detector and a signal acquisition time to control the signal intensity.

10. The sensor of claim 8, wherein the electronic processor is configured to maintain the detector signal intensity within a predetermined range by selecting a different one of the plurality of radiation sources to direct incident radiation to the subject.

11. The sensor of claim 1, wherein the electronic processor is configured to provide information about the one or more properties of the subject to a therapeutic device to control the therapeutic device.

12. A sensor, comprising:
  a flexible mounting member comprising an adhesive surface configured to attach directly to a sample and to assume a shape corresponding to at least a portion of the sample when it attaches to the sample;
  a rigid mounting member connected to the flexible mounting member; and a plurality of radiation sources, a spectral detector, and an electronic processor mounted to the rigid mounting member, wherein the plurality of radiation sources comprises a short-distance source positioned at a distance of 9 mm or less from the detector, and at least two long-distance sources positioned at a different distances at least 10 mm from the detector; and wherein during operation of the sensor, the electronic processor is configured to:

select one of the at least two long-distance sources by:
(i) exposing the sample to incident radiation produced by one of the long-distance sources;
(ii) measuring reflected or transmitted radiation from the sample using the spectral detector;
(iii) repeating (i) and (ii) for each of the long-distance sources to generate spectral information corresponding to each of the long-distance sources;
(iv) comparing the spectral information for each of the long-distance sources to expected peak information to determine which ones of the long-distance sources are suitable for illumination of the sample; and
(v) selecting one of the suitable long-distance sources from (iv) based on acquisition times associated with the spectral information corresponding to each of the suitable long-distance sources;

expose the sample to incident radiation from the short-distance source and from the selected long-distance source and use the spectral detector to measure radiation from the sample corresponding to illumination by the short-distance source and the selected long-distance source; and analyze the measured radiation to determine one or more properties of the sample.

13. The sensor of claim 12, wherein the flexible mounting member is disposable and at least partially transmissive to near-infrared radiation and forms a window through which incident radiation produced by the radiation sources passes to reach the sample.

14. The sensor of claim 12, wherein the one or more properties comprise at least one of oxygen tension, oxygen saturation, pH, hematocrit, hemoglobin concentration, anaerobic threshold, water content, and oxygen consumption of the sample.

15. A method for measuring one or more sample properties, the method comprising:

selecting one of a plurality of long-distance radiation sources of a sensor, wherein each of the long-distance sources is positioned at a different distance at least 10 mm from a detector of the sensor, wherein the selecting comprises:

(i) exposing the sample to incident radiation produced by one of the long-distance sources;
(ii) measuring reflected or transmitted radiation from the sample;
(iii) repeating (i) and (ii) for each of the long-distance sources to generate spectral information corresponding to each of the long-distance sources;
(iv) comparing the spectral information for each of the long-distance sources to expected peak information to determine which ones of the long-distance sources are suitable for illumination of the sample; and
(v) selecting one of the suitable long-distance sources from (iv) based on acquisition times associated with the spectral information corresponding to each of the suitable long-distance sources;

exposing the sample to incident radiation from a short-distance source positioned at a distance of 9 mm or less from the detector and from the selected long-distance source, and measuring radiation from the sample corresponding to illumination by the short-distance source and the selected long-distance source; and analyzing the measured radiation to determine one or more sample properties.

16. The method of claim 15, further comprising:
calculating an absorbance spectrum for the sample corresponding to illumination of the sample by the short-distance source;
calculating an absorbance spectrum for the sample corresponding to illumination of the sample by the selected long-distance source; and
correcting the absorbance spectrum corresponding to illumination by the long-distance source to reduce spectral effects due to skin and fat layers in the sample using information derived from the absorbance spectrum corresponding to illumination by the short-distance source.

17. The method of claim 15, further comprising, during measurement of radiation from the sample, maintaining an intensity of a detected radiation signal greater than zero and within a predetermined range of signal intensities.

18. The method of claim 17, wherein maintaining the signal intensity within a predetermined range comprises adjusting at least one of an electronic gain of a detector and a signal acquisition time during which the radiation is measured to control the signal intensity.

19. The method of claim 17, wherein maintaining the signal intensity within a predetermined range comprises using a different radiation source to direct radiation to the sample.

20. The method of claim 15, wherein the one or more sample properties comprise at least one of oxygen saturation, oxygen tension, pH, hematocrit, hemoglobin concentration, anaerobic threshold, water content, and oxygen consumption of the sample.

* * * * *